US 10,780,218 B2

(12) United States Patent
Novakovic et al.

(10) Patent No.: US 10,780,218 B2
(45) Date of Patent: Sep. 22, 2020

(54) INTRAOCULAR IMPLANT DELIVERY APPARATUS AND METHODS OF USE THEREOF

(71) Applicant: Allergan, Inc., Irvine, CA (US)

(72) Inventors: Zoran Novakovic, Irvine, CA (US); Rahul Bhagat, Irvine, CA (US); Shawn R. Davis, Temecula, CA (US); David Mucientes, Long Beach, CA (US); Michael R. Robinson, Irvine, CA (US); Vaclav Vojan, Plzen (CZ); Michael Strehl, Pfreimd (DE); Ina Michaelis, Schwandorf (DE); Maximilian Vogl, Mantel (DE); Jessica Kreher, Schwandorf (DE)

(73) Assignee: Allergan, Inc., Irvine, CA (US)

( * ) Notice: Subject to any disclaimer, the term of this patent is extended or adjusted under 35 U.S.C. 154(b) by 214 days.

(21) Appl. No.: 14/632,783

(22) Filed: Feb. 26, 2015

(65) Prior Publication Data
US 2015/0238687 A1 Aug. 27, 2015

Related U.S. Application Data

(60) Provisional application No. 61/944,840, filed on Feb. 26, 2014.

(51) Int. Cl.
*A61M 5/158* (2006.01)
*A61F 9/00* (2006.01)
*A61F 9/007* (2006.01)

(52) U.S. Cl.
CPC ........... *A61M 5/158* (2013.01); *A61F 9/0008* (2013.01); *A61F 9/00781* (2013.01)

(58) Field of Classification Search
CPC .... A61M 5/158; A61M 31/007; A61M 31/00; A61M 2210/0612; A61M 37/0069;
(Continued)

(56) References Cited

U.S. PATENT DOCUMENTS

| 1,347,622 A | 7/1920 | Deininger |
| 2,632,444 A | 3/1953 | Kas |

(Continued)

FOREIGN PATENT DOCUMENTS

| WO | WO2000-49975 | 8/2000 |
| WO | WO2003-015504 | 2/2003 |

(Continued)

OTHER PUBLICATIONS

CAS RN 155206-00-1 May 20, 1994.
(Continued)

*Primary Examiner* — Kevin C Sirmons
*Assistant Examiner* — Alexandra Lalonde
(74) *Attorney, Agent, or Firm* — Morgan, Lewis & Bockius LLP

(57) ABSTRACT

Apparatus and methods for introducing a solid or semi-solid intraocular drug-containing implant into the anterior chamber of an eye are described. The drug-containing implant can be a rod-shaped biodegradable implant that may provide for the extended release of the drug and may be effective for treating a medical condition of the eye. The apparatus is ergonomically designed in the shape or style of a pen with tactile surfaces for easy gripping, a needle-rotation knob to permit orientation of the needle bevel in relation to the eye, and a spring-actuated mechanism for consistent deployment of the implant.

14 Claims, 30 Drawing Sheets

(58) Field of Classification Search
CPC .... A61F 9/0008; A61F 2/167; A61F 9/00781; A61F 9/0017; A61F 9/0026; A61K 9/0024; A61D 7/00; A61B 17/0469; A61B 17/062; A61B 18/1442; A61B 2017/2929; A61B 17/2929

See application file for complete search history.

(56) References Cited

U.S. PATENT DOCUMENTS

| | | |
|---|---|---|
| 2,659,369 A | 11/1953 | Lipman |
| 2,761,446 A | 9/1956 | Reed |
| 2,850,013 A | 9/1958 | Cordis |
| 2,883,984 A | 4/1959 | Candido, Jr. et al. |
| 2,907,327 A | 10/1959 | White |
| 3,016,895 A | 1/1962 | Sein |
| 3,402,712 A | 9/1968 | Eisenhand |
| 3,538,916 A | 11/1970 | Wiles et al. |
| 3,712,301 A | 1/1973 | Sarnoff |
| 3,744,493 A | 7/1973 | Booher et al. |
| 3,774,607 A | 11/1973 | Schmitz |
| 4,077,406 A | 3/1978 | Sandhage et al. |
| 4,105,030 A | 8/1978 | Kercso |
| 4,154,239 A | 5/1979 | Turley |
| 4,400,170 A | 8/1983 | McNaughton et al. |
| 4,403,610 A | 9/1983 | Lodge et al. |
| 4,451,254 A | 5/1984 | Dinius et al. |
| 4,659,326 A | 4/1987 | Johnson et al. |
| 4,673,387 A | 6/1987 | Phillips et al. |
| 4,787,384 A | 11/1988 | Campbell et al. |
| 4,900,304 A | 2/1990 | Fujioka et al. |
| 4,915,686 A | 4/1990 | Frederick |
| 4,950,234 A | 8/1990 | Fujioka et al. |
| 5,106,370 A | 4/1992 | Stewart |
| 5,135,493 A | 8/1992 | Peschke |
| 5,250,026 A | 10/1993 | Ehrlich et al. |
| 5,273,532 A | 12/1993 | Niezink et al. |
| 5,279,554 A | 1/1994 | Turley |
| 5,284,479 A | 2/1994 | de Jong |
| 5,288,291 A | 2/1994 | Teoh |
| 5,300,079 A | 4/1994 | Niezink et al. |
| 5,304,119 A | 4/1994 | Balaban et al. |
| 5,395,319 A | 3/1995 | Hirsch et al. |
| 5,478,316 A | 12/1995 | Bitdinger et al. |
| 5,484,403 A | 1/1996 | Yoakum et al. |
| 5,520,660 A | 5/1996 | Loos et al. |
| 5,522,792 A | 6/1996 | Bassett et al. |
| 5,810,769 A | 9/1998 | Schlegel et al. |
| 5,817,054 A | 10/1998 | Grimm |
| 5,827,293 A | 10/1998 | Elliott |
| 5,874,098 A | 2/1999 | Stevens et al. |
| 5,997,500 A | 12/1999 | Cook et al. |
| 6,159,218 A | 12/2000 | Aramant et al. |
| 6,190,350 B1 | 2/2001 | Davis et al. |
| 6,228,054 B1* | 5/2001 | Dysarz ............ A61M 5/3234 604/110 |
| 6,258,056 B1 | 7/2001 | Turley et al. |
| 6,270,508 B1* | 8/2001 | Klieman ............ A61B 17/062 606/147 |
| 6,273,894 B1 | 8/2001 | Dykes |
| 6,290,980 B1 | 9/2001 | Hansen |
| 6,299,603 B1 | 10/2001 | Hecker et al. |
| 6,402,677 B1 | 6/2002 | Jacobs |
| 6,402,716 B1 | 6/2002 | Ryoo et al. |
| 6,527,780 B1 | 3/2003 | Wallace et al. |
| 6,899,717 B2 | 5/2005 | Lathrop et al. |
| 7,090,681 B2 | 8/2006 | Weber et al. |
| 7,147,644 B2 | 12/2006 | Weber et al. |
| 7,468,065 B2 | 12/2008 | Weber et al. |
| D592,746 S | 5/2009 | Highley et al. |
| 7,740,619 B2 | 6/2010 | Pinedjian et al. |
| 7,753,916 B2 | 7/2010 | Weber et al. |
| 7,799,336 B2 | 9/2010 | Hughes et al. |
| 7,806,866 B2 | 10/2010 | Hommann et al. |
| 7,855,176 B1 | 12/2010 | Altman et al. |
| 7,862,543 B2 | 1/2011 | Potter et al. |
| 8,105,271 B2 | 1/2012 | Matusch |
| 8,287,494 B2 | 10/2012 | Ma |
| 8,721,702 B2* | 5/2014 | Romoda ............ A61F 9/0008 604/8 |
| 2001/0008961 A1 | 7/2001 | Hecker et al. |
| 2002/0022881 A1 | 2/2002 | Figueroa et al. |
| 2002/0049411 A1 | 4/2002 | Lamoureux et al. |
| 2002/0111603 A1 | 8/2002 | Cheikh |
| 2002/0188247 A1 | 12/2002 | Peery |
| 2002/0193743 A1 | 12/2002 | Kneer |
| 2003/0004491 A1 | 1/2003 | Tenhuisen et al. |
| 2003/0013934 A1 | 1/2003 | Schmidt |
| 2003/0018233 A1 | 1/2003 | Miller |
| 2003/0040699 A1 | 2/2003 | Talling et al. |
| 2003/0050595 A1 | 3/2003 | Campbell |
| 2003/0093084 A1 | 5/2003 | Nissan et al. |
| 2003/0135153 A1 | 7/2003 | Hagemeier |
| 2003/0233101 A1 | 12/2003 | Lubock et al. |
| 2004/0022832 A1 | 2/2004 | Bachman et al. |
| 2004/0054374 A1 | 3/2004 | Weber |
| 2004/0122312 A1 | 6/2004 | Chesbrough et al. |
| 2004/0124105 A1 | 7/2004 | Seiler et al. |
| 2004/0137059 A1* | 7/2004 | Nivaggioli ............ A61K 9/0051 424/468 |
| 2004/0199140 A1 | 10/2004 | Rue et al. |
| 2004/0215133 A1 | 10/2004 | Weber et al. |
| 2004/0236343 A1 | 11/2004 | Taylor et al. |
| 2004/0243141 A1 | 12/2004 | Brown et al. |
| 2005/0101967 A1 | 5/2005 | Weber |
| 2005/0154399 A1 | 7/2005 | Weber et al. |
| 2005/0203542 A1 | 9/2005 | Weber et al. |
| 2005/0244464 A1 | 11/2005 | Hughes |
| 2006/0211982 A1 | 9/2006 | Prestrelski et al. |
| 2006/0241650 A1* | 10/2006 | Weber ............ A61F 2/167 606/107 |
| 2007/0016226 A1 | 1/2007 | Campbell et al. |
| 2007/0060887 A1 | 3/2007 | Marsh et al. |
| 2007/0078291 A1 | 4/2007 | Terwilliger et al. |
| 2007/0167918 A1 | 7/2007 | Reed et al. |
| 2008/0033351 A1 | 2/2008 | Trogden |
| 2008/0042849 A1 | 2/2008 | Saito et al. |
| 2008/0097335 A1 | 4/2008 | Trogden et al. |
| 2008/0112510 A1 | 5/2008 | Nakao et al. |
| 2008/0145403 A1 | 6/2008 | Spada |
| 2008/0221510 A1 | 9/2008 | Van Der Graaf et al. |
| 2009/0012463 A1 | 1/2009 | Beelen et al. |
| 2009/0142727 A1 | 6/2009 | Lawter et al. |
| 2009/0156987 A1 | 6/2009 | McLean et al. |
| 2009/0209804 A1 | 8/2009 | Seiler et al. |
| 2009/0281520 A1* | 11/2009 | Highley ............ A61F 9/0017 604/506 |
| 2009/0292293 A1 | 11/2009 | Bogaert et al. |
| 2010/0010452 A1 | 1/2010 | Paques et al. |
| 2010/0042041 A1 | 2/2010 | Tune et al. |
| 2010/0057093 A1 | 3/2010 | Ide et al. |
| 2010/0185205 A1 | 7/2010 | Novakovic et al. |
| 2010/0298807 A1 | 11/2010 | Jansen et al. |
| 2011/0060279 A1 | 3/2011 | Altman et al. |
| 2011/0066112 A1 | 3/2011 | Altman et al. |
| 2011/0098675 A1 | 4/2011 | Schmalz |
| 2011/0152755 A1 | 6/2011 | Schmalz |
| 2012/0078224 A1 | 3/2012 | Lerner et al. |
| 2012/0083784 A1* | 4/2012 | Davison ............ A61B 18/1445 606/48 |
| 2012/0123324 A1 | 5/2012 | Schmalz |
| 2012/0165722 A1 | 6/2012 | Horvath et al. |
| 2012/0165933 A1* | 6/2012 | Haffner ............ A61F 9/0017 623/6.64 |
| 2012/0232017 A1 | 9/2012 | Altman et al. |
| 2012/0265149 A1 | 10/2012 | Lerner et al. |
| 2013/0158561 A1 | 6/2013 | Bhagat et al. |
| 2013/0253528 A1 | 9/2013 | Haffner et al. |

FOREIGN PATENT DOCUMENTS

| | | |
|---|---|---|
| WO | 2004-026106 | 4/2004 |
| WO | 2004-073784 | 9/2004 |

(56) References Cited

FOREIGN PATENT DOCUMENTS

| WO | 2006-071554 | 7/2006 |
| WO | WO2011-120608 | 10/2011 |
| WO | WO2011-128015 | 10/2011 |

OTHER PUBLICATIONS

Coleman, Anne et al, A 3-Month Randomized Controlled Trial of Bimatoprost (LUMIGAN) Versus Combined Timolol and Dorzolamide (Cosopt) in Patients with Glaucoma or Ocular Hypertension, Ophthalmology, 2003, 2362-8, 110-12.
Patil, A. Jayaprakash, et al., Bimatoprost—a review, Expert Opinion Pharacother, 2009, 2759-2768, vol. 10, No. 16, Informa UK Ltd., GB.
Schuster, Victor et al, Synthetic Modification of Prostaglandin F2α Indicates Different Structural Determinants of Binding to the Prostaglandin F Receptor Versus the Prostaglandin Transporter, Molecular Pharmacology, 2000, 1511-1516, 58.
Woodward, David et al, Bimatoprost: A Novel Antiglaucoma Agent, Cardiovascular Drug Reviews, 2004, 103-120, 22(2).
Woodward, David et al, Identification of an antagonist that selectively blocks the activity of prostamides (prostaglandin-ethanolamides) in the feline iris, British Journal of Pharmacology, 2007, 342-352, 150.
Woodward, David et al, Prostamides (Prostaglandin-ethanolamides) and Their Pharmacology, British Journal of Pharmacology, 2008, 410-419, 153.
Yu, Ming, et al., Synthesis of Prostaglandin E2 Ethanolamide from Anandamide by Cyclooxygenase-2, The Journal of Biological Chemistry, Aug. 22, 1997, 21181-21186, vol. 272, No. 34, US.
International Search Report and Written Opinion, International Application No. PCT/US2015/017779, dated May 15, 2015.

\* cited by examiner

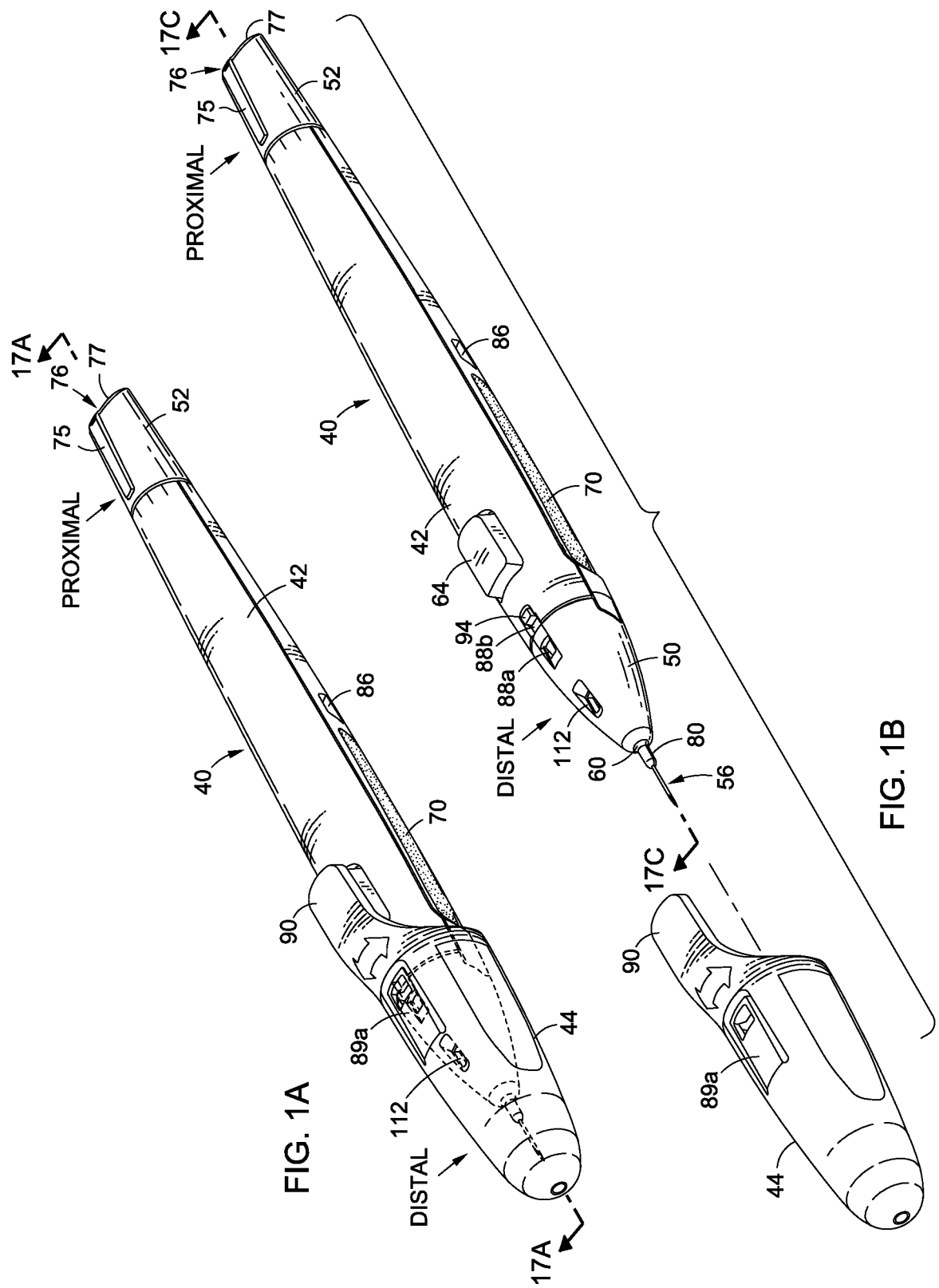

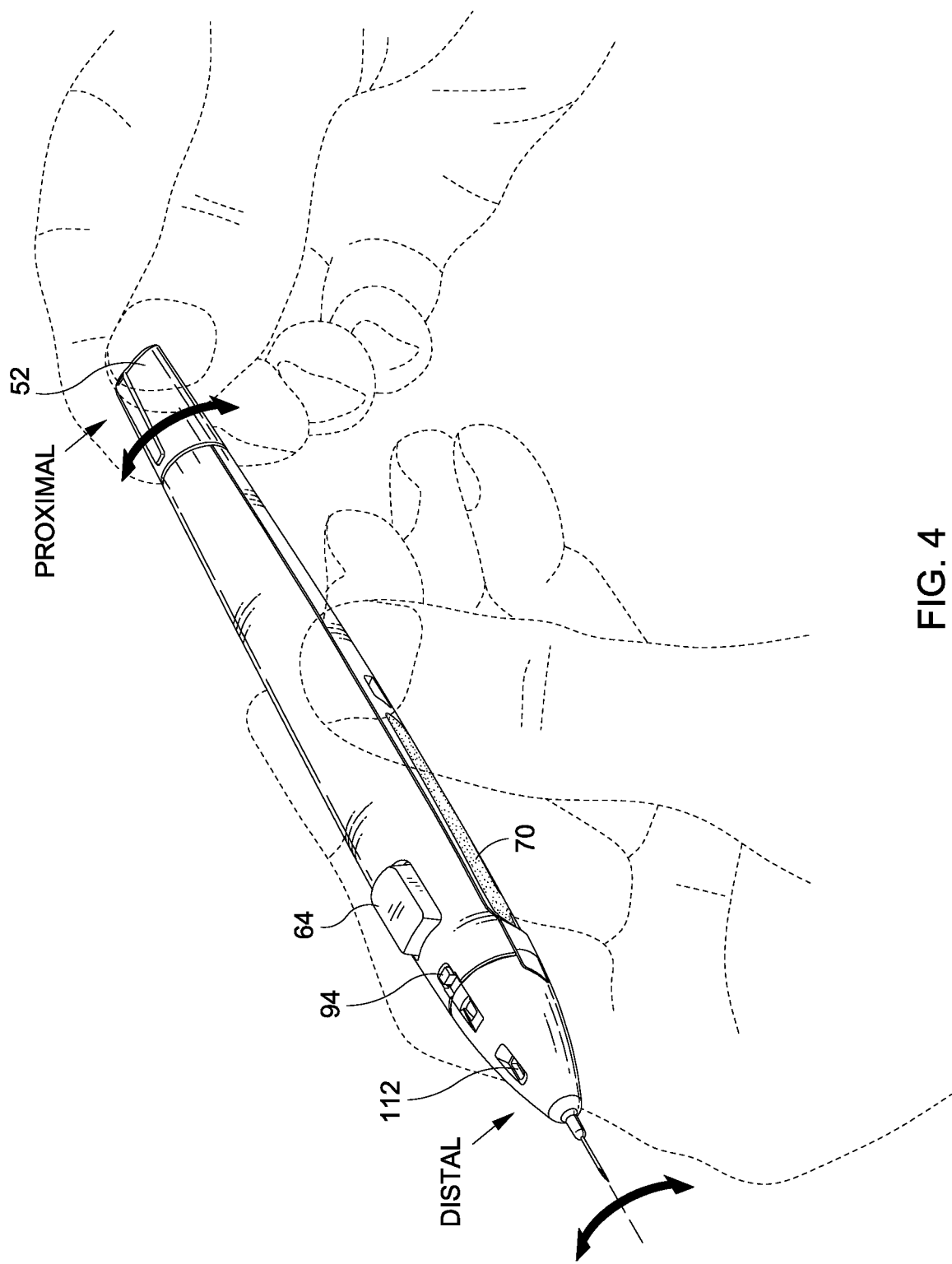

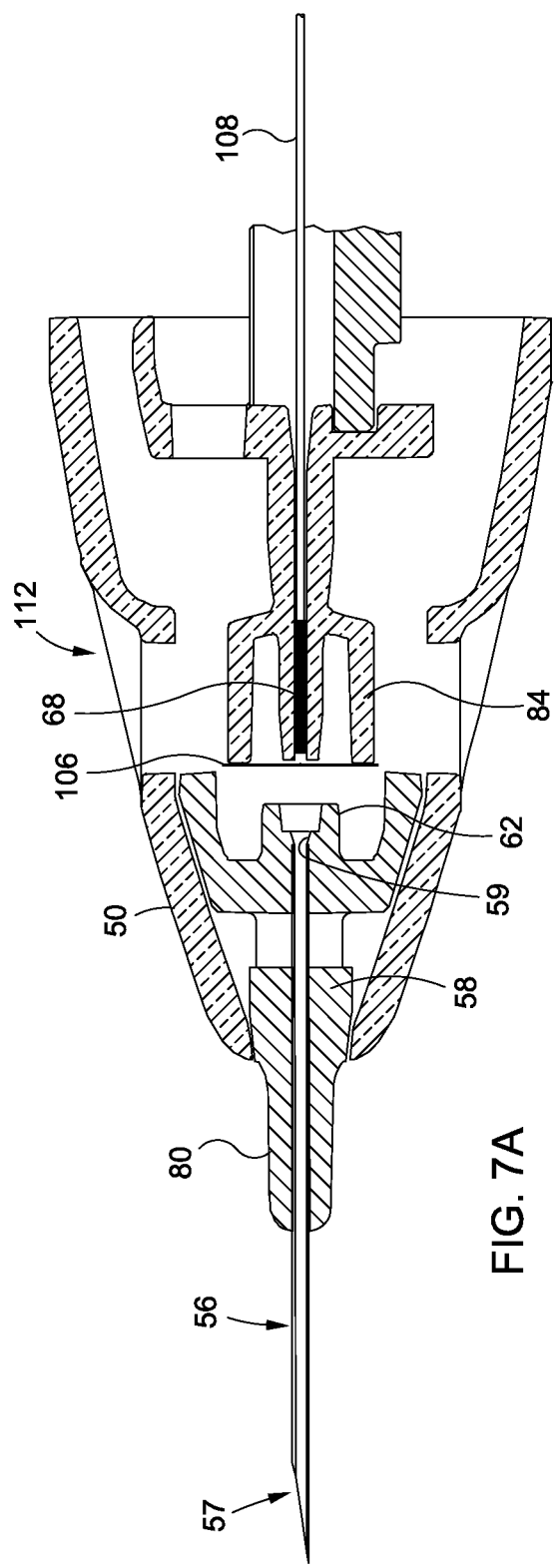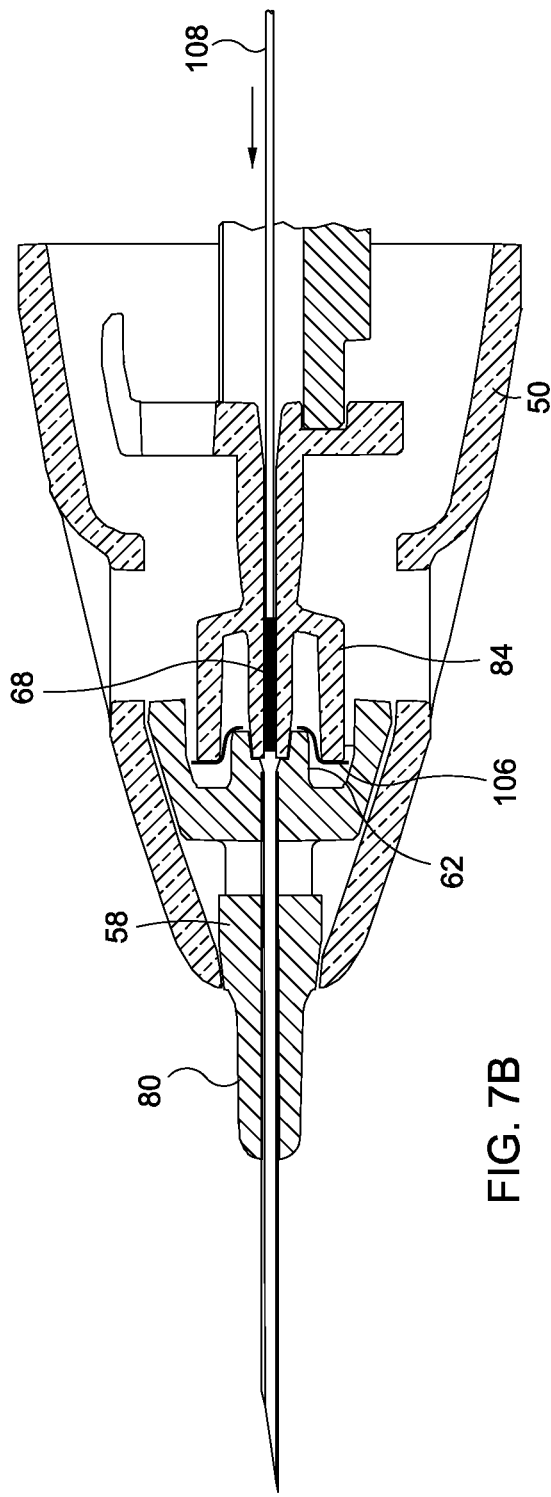
FIG. 7A
FIG. 7B

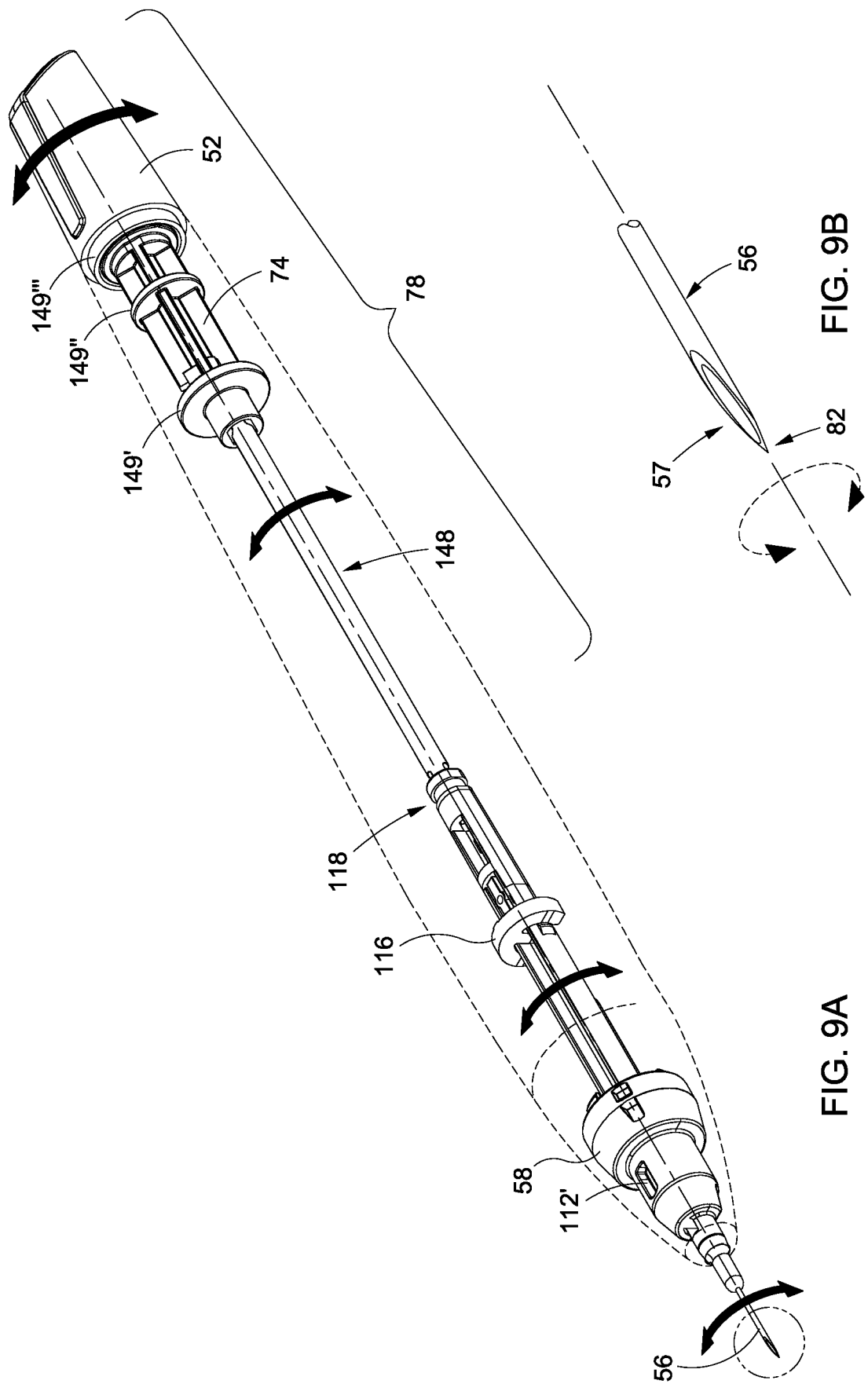

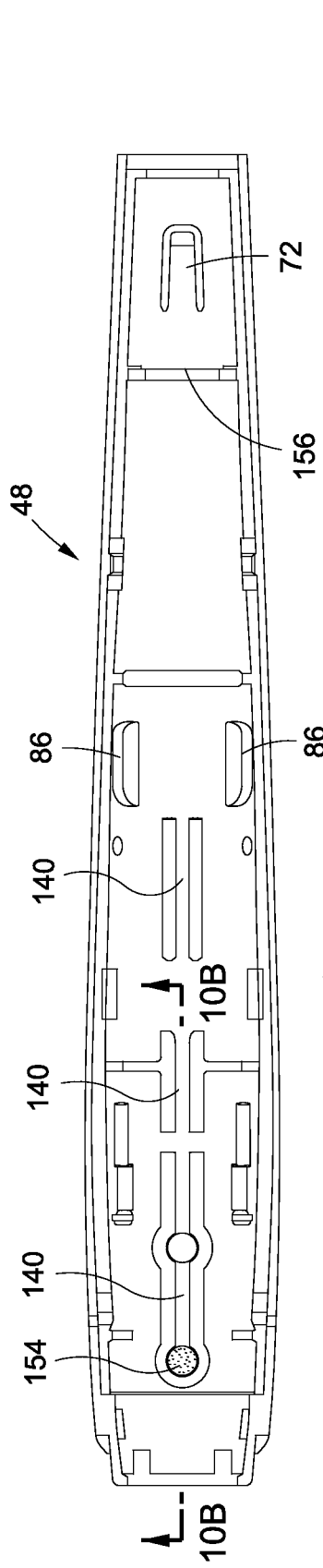
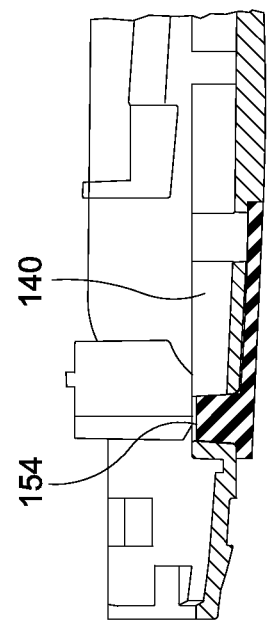
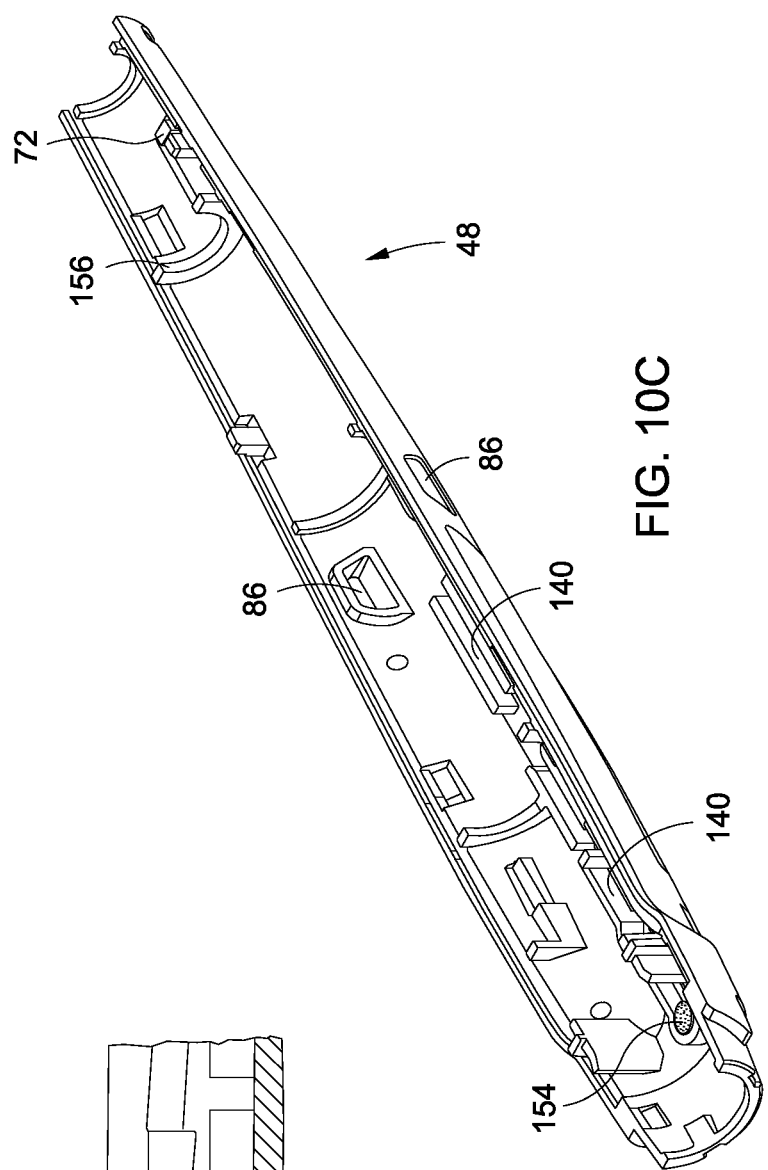

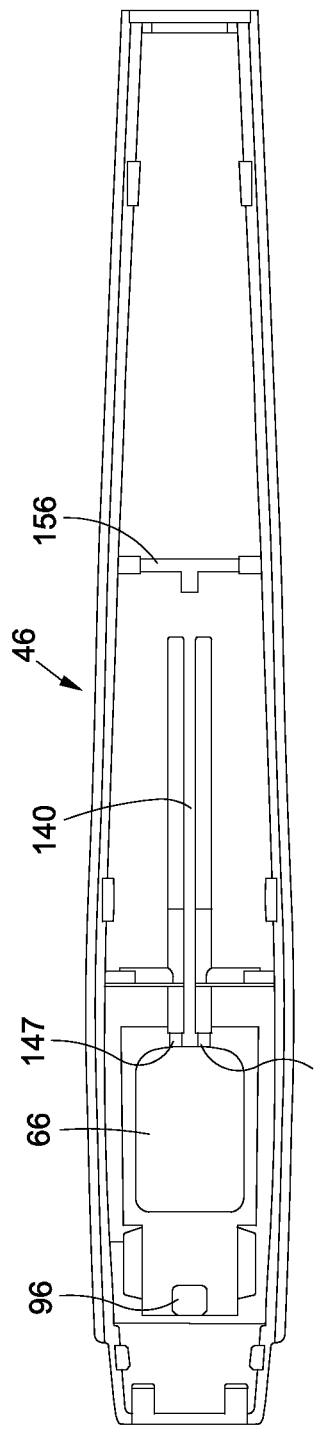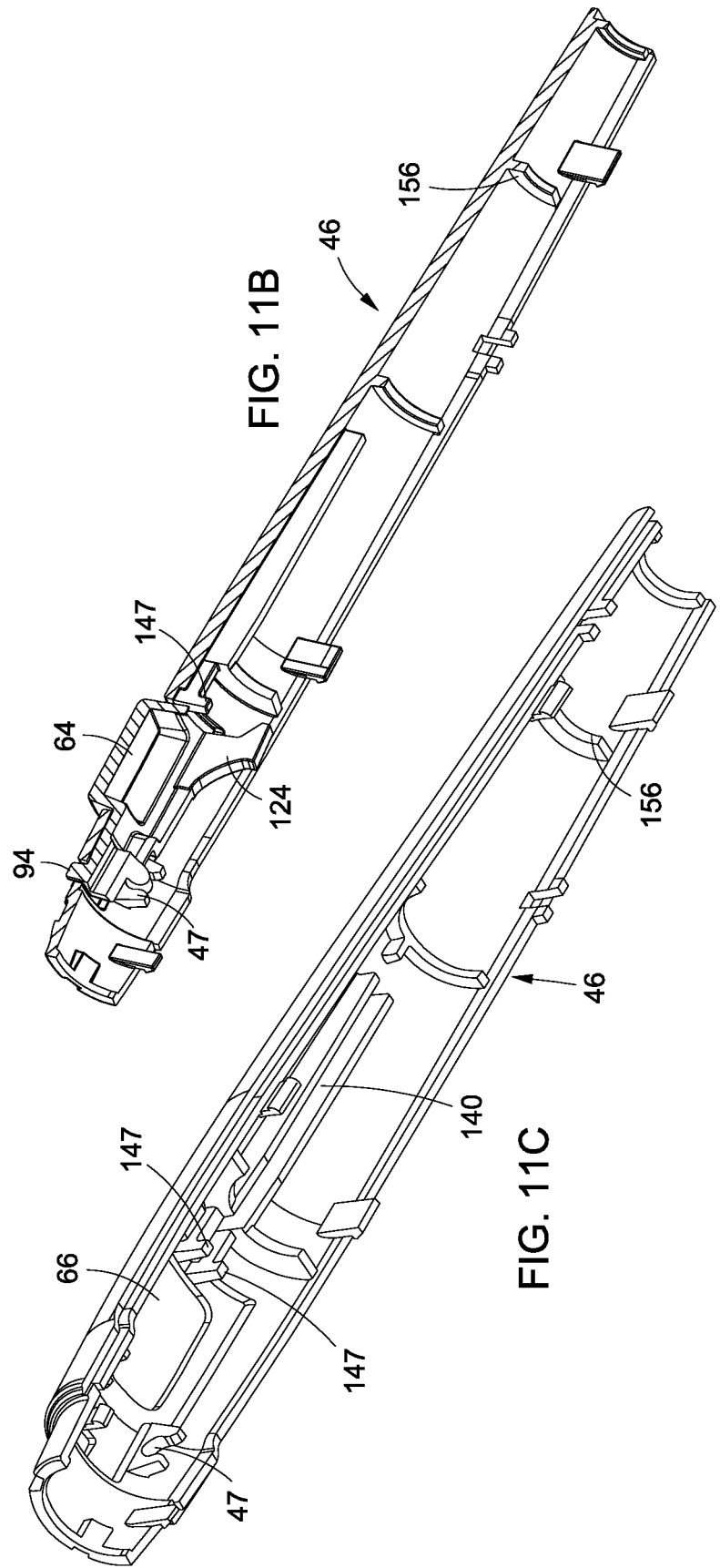

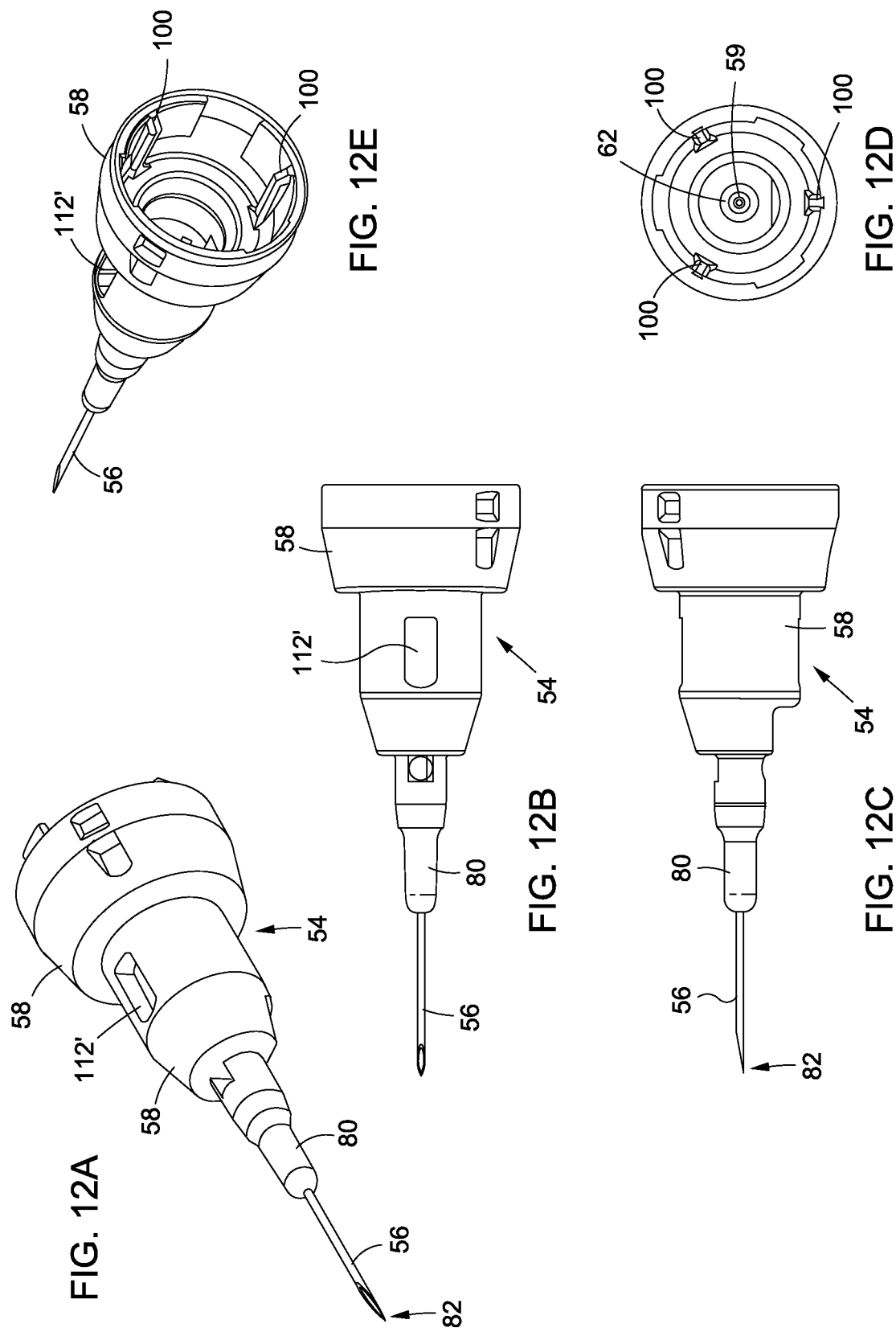

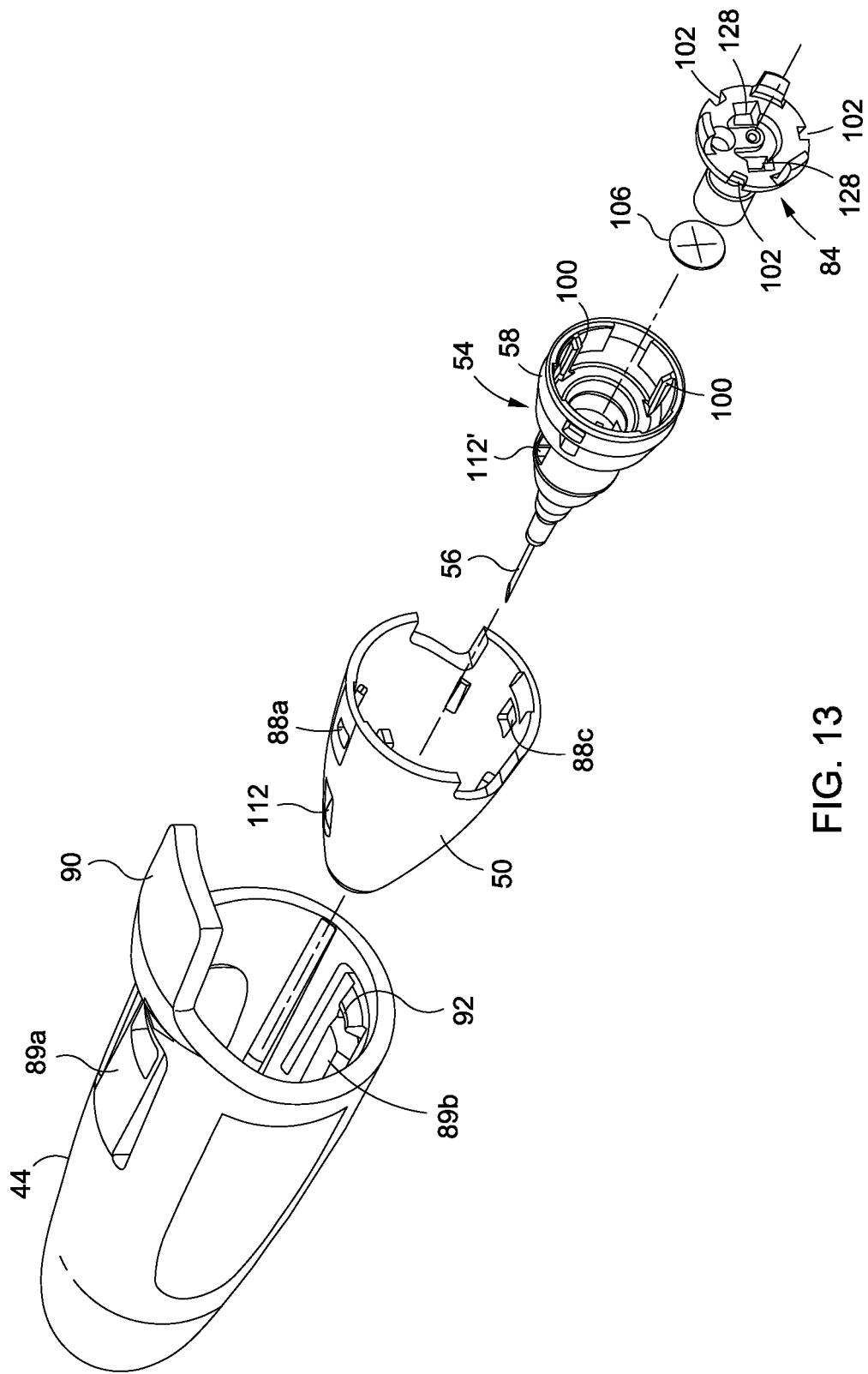

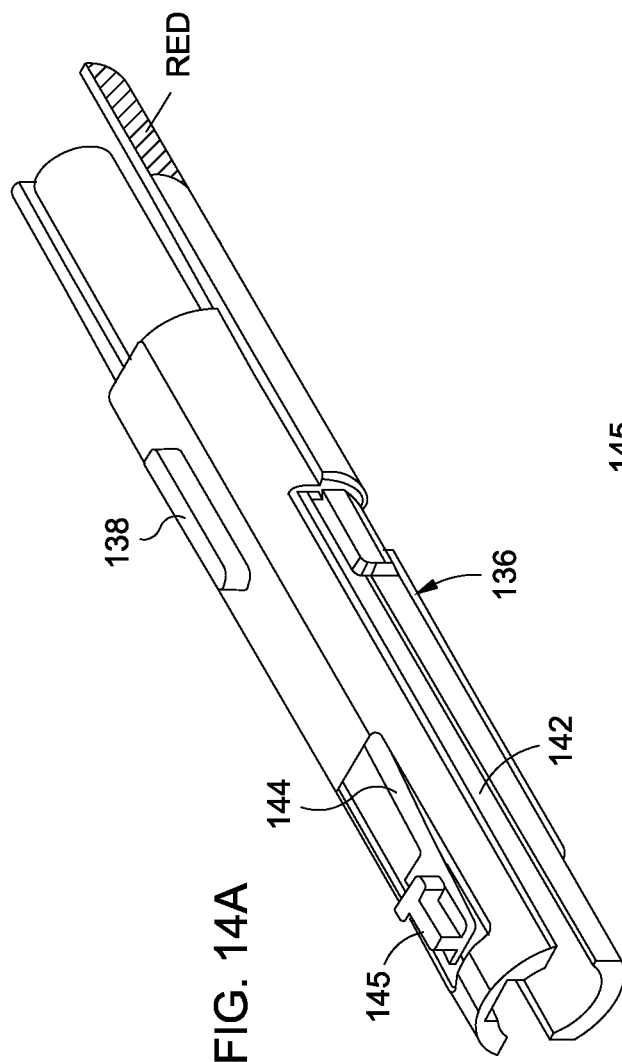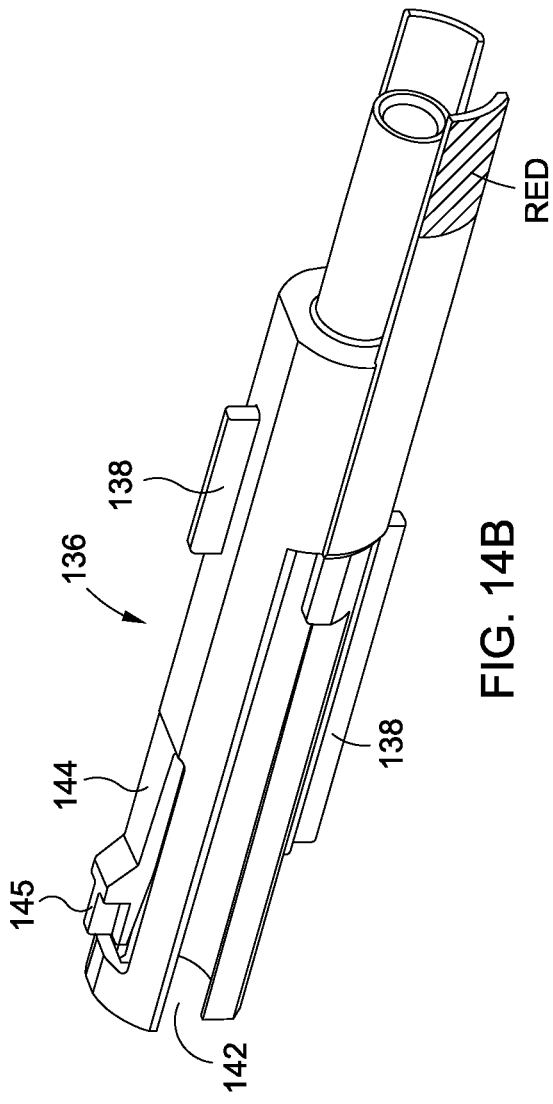

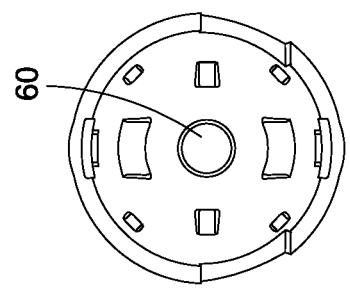
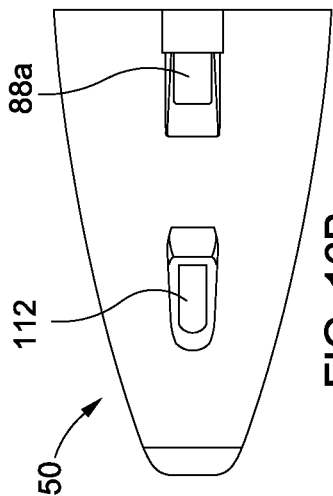
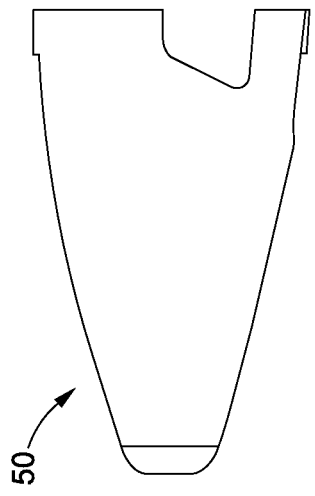
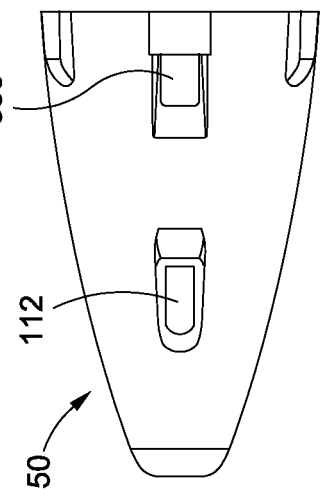
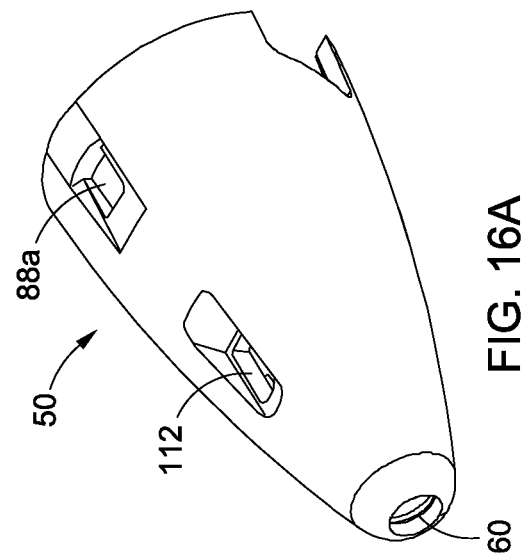

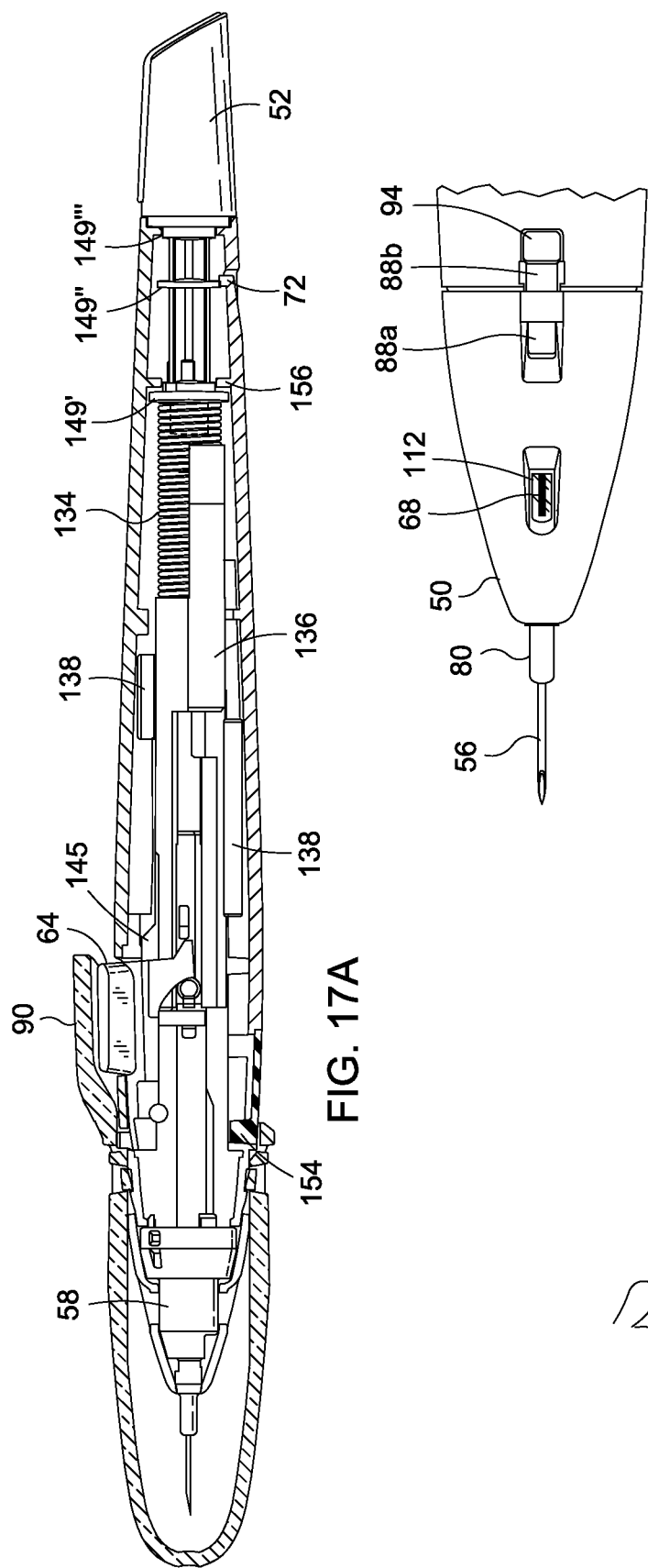
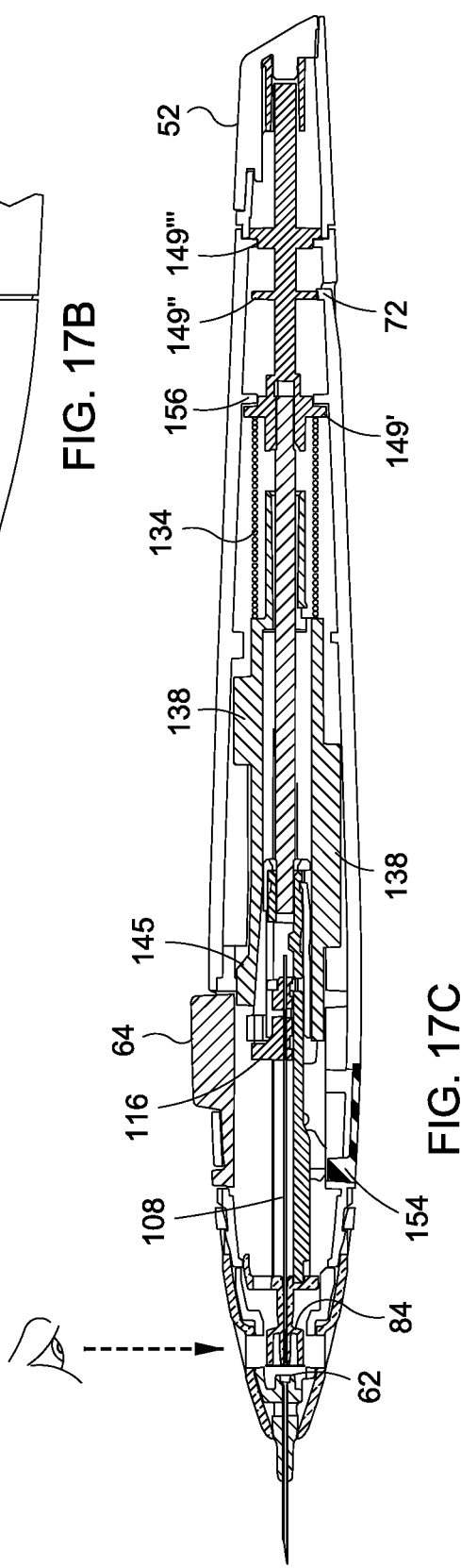
FIG. 17A  FIG. 17B  FIG. 17C

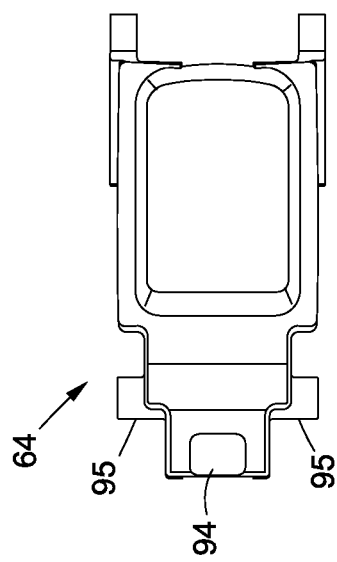
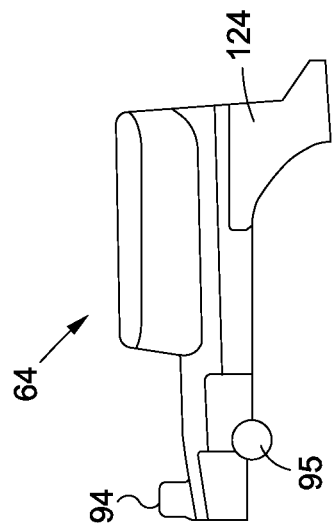
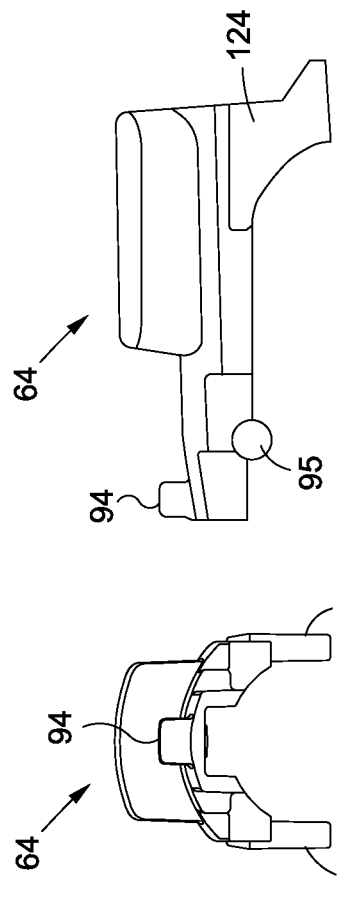
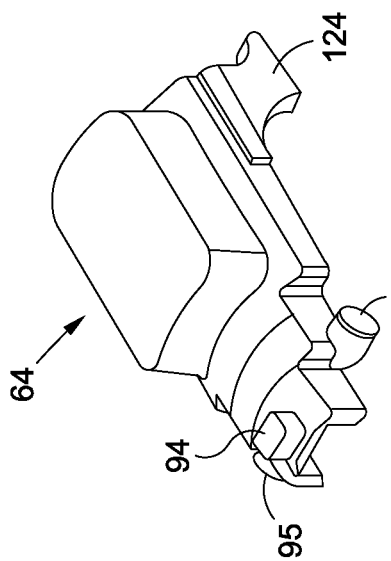
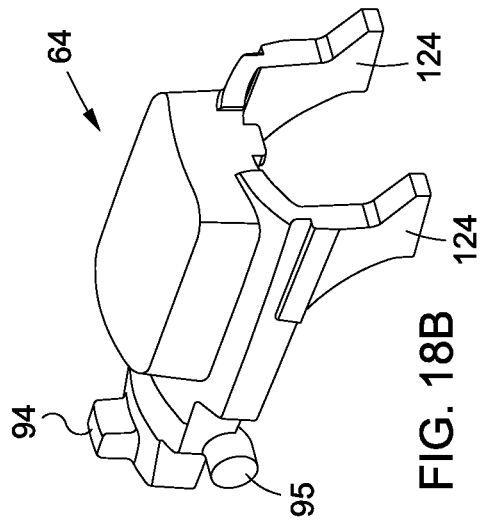

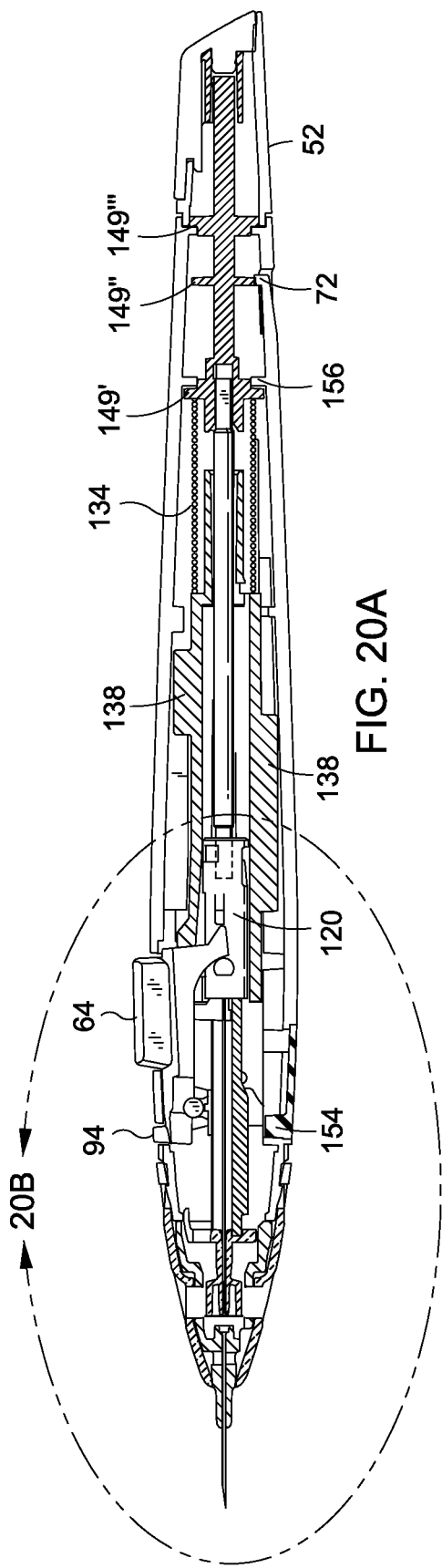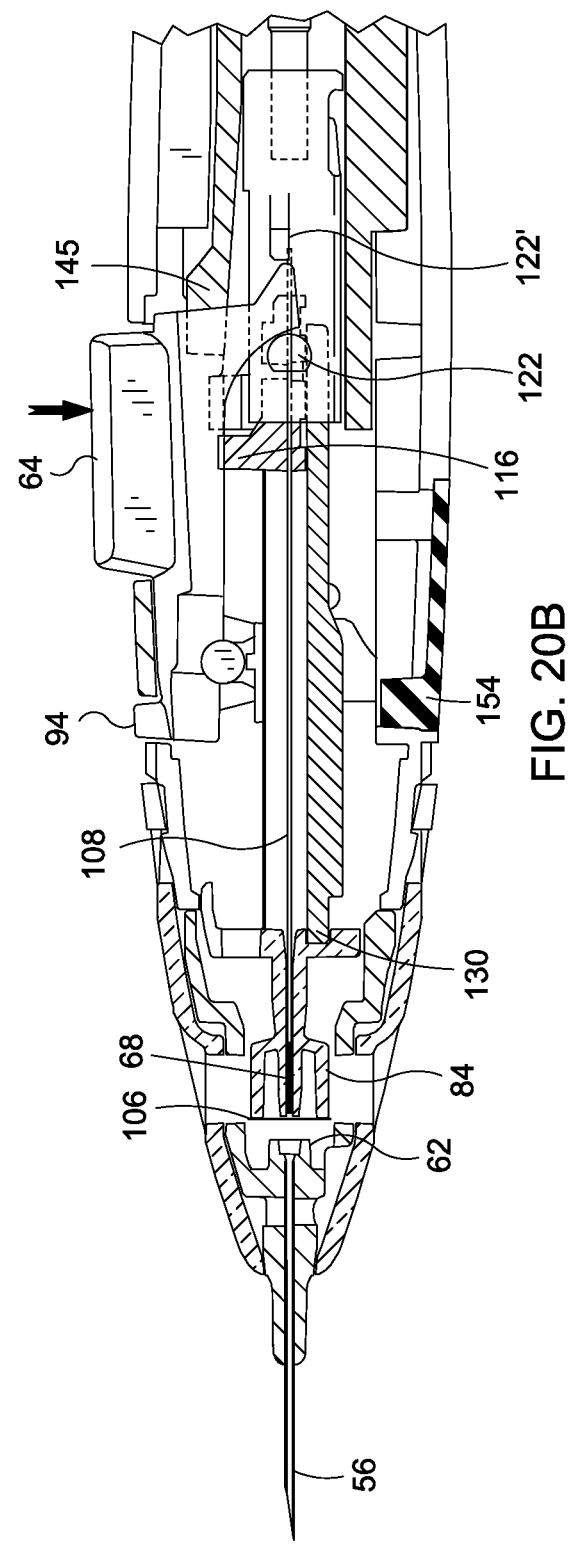
FIG. 20A
FIG. 20B

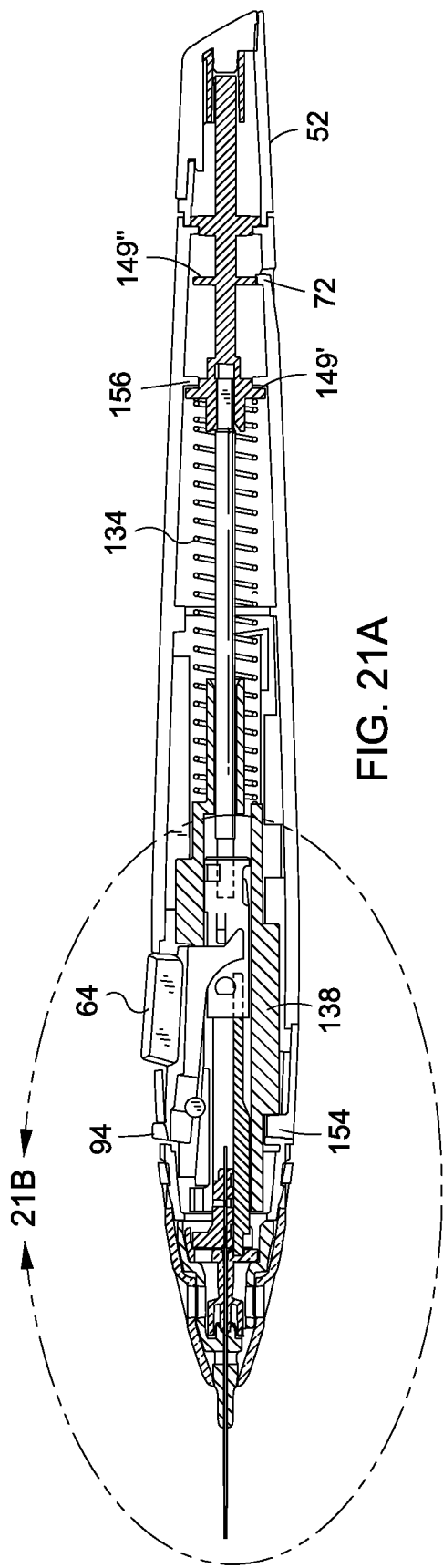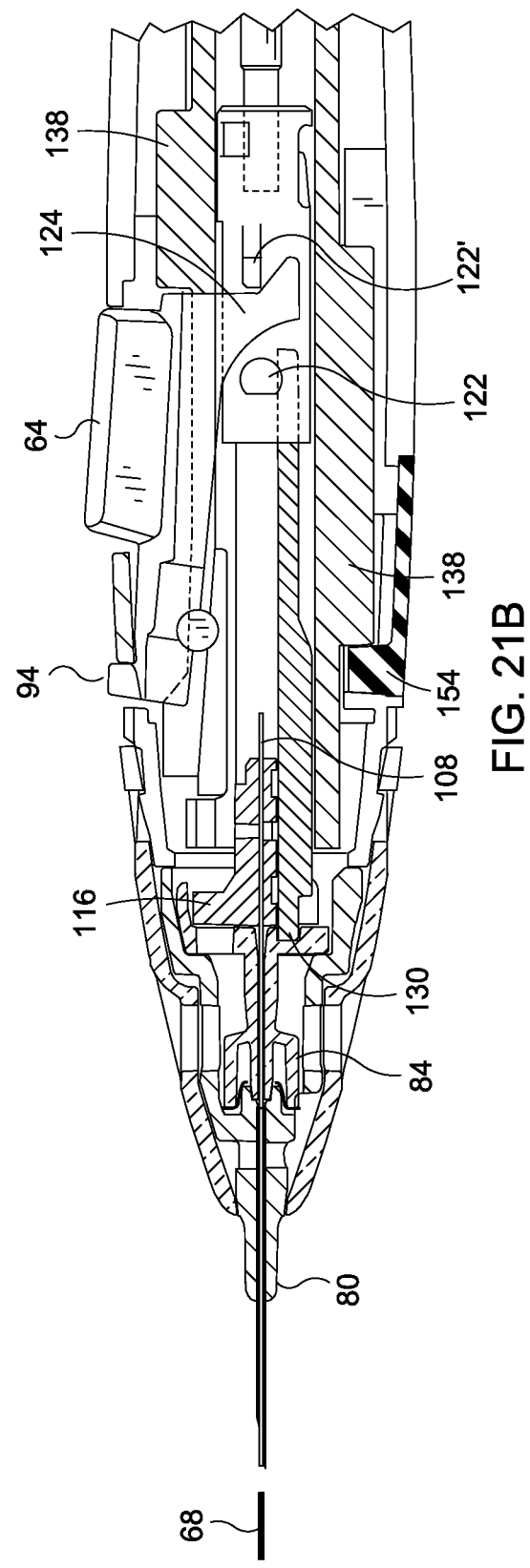
FIG. 21A
FIG. 21B

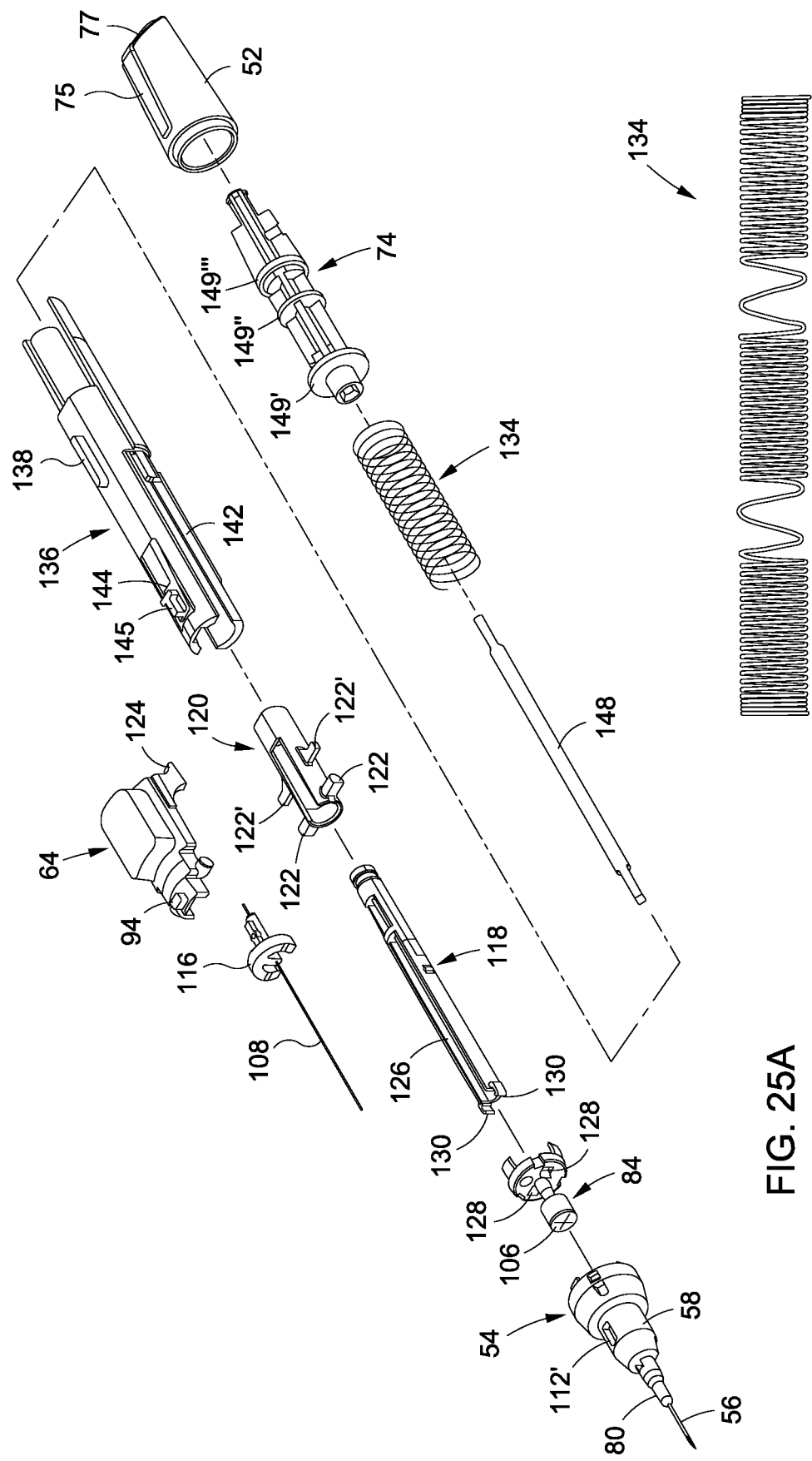

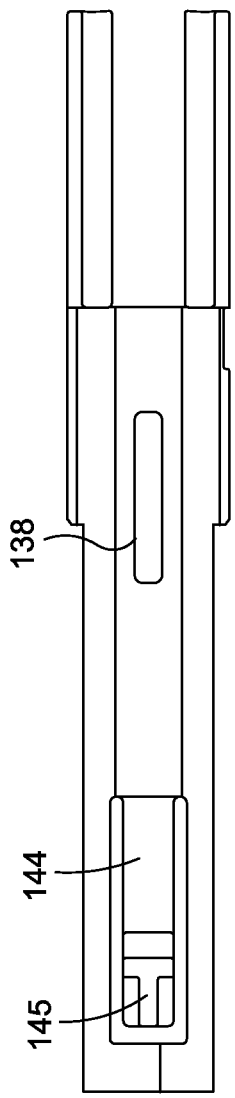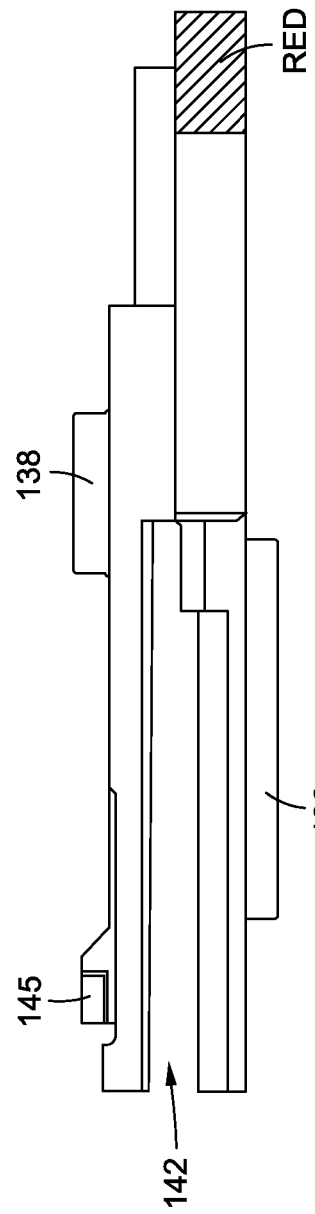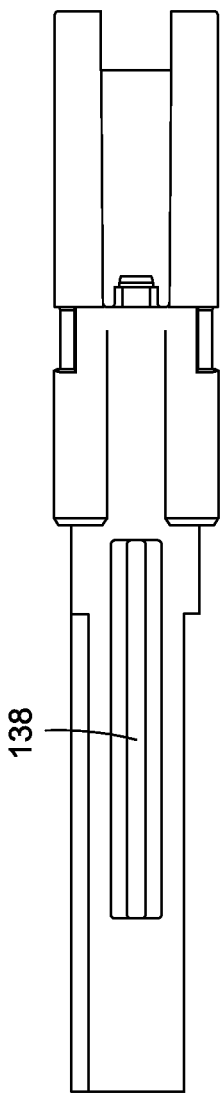
FIG. 26A
FIG. 26B
FIG. 26C

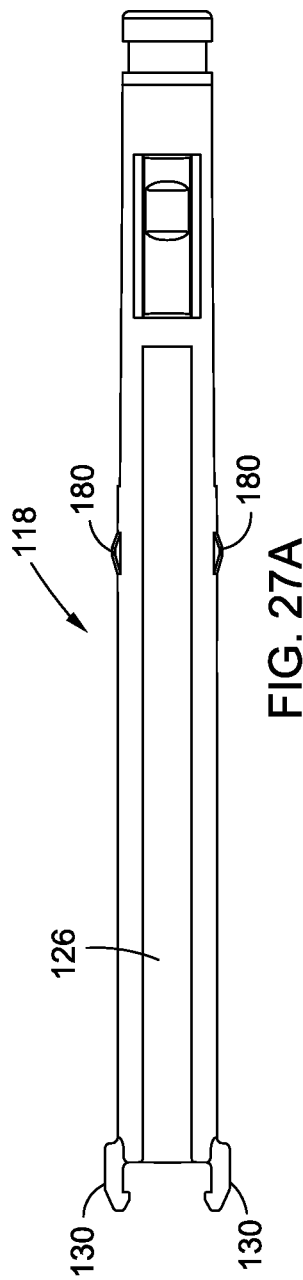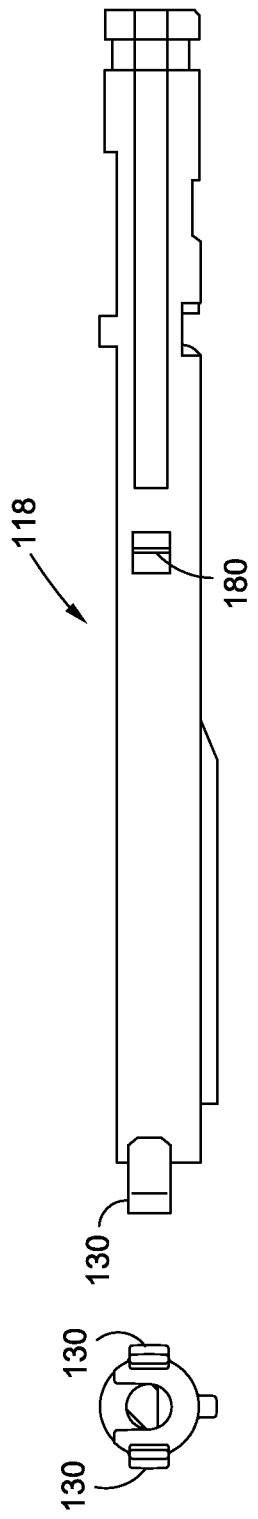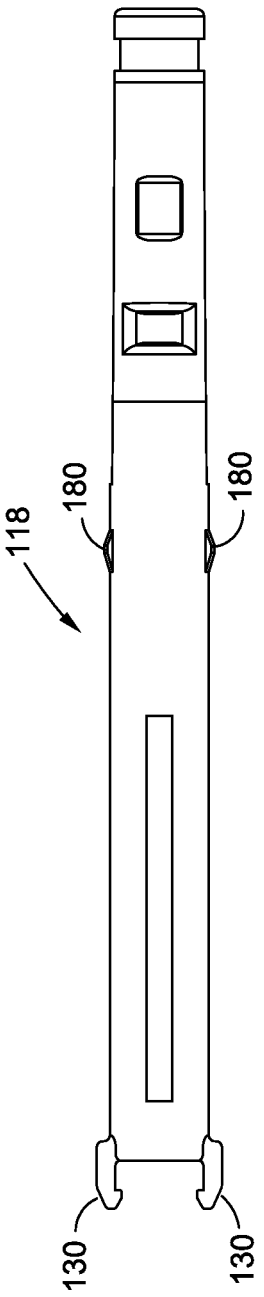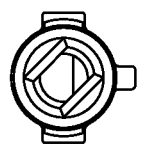
FIG. 27A
FIG. 27B
FIG. 27C
FIG. 27D
FIG. 27E

# INTRAOCULAR IMPLANT DELIVERY APPARATUS AND METHODS OF USE THEREOF

CROSS-REFERENCE TO RELATED APPLICATIONS

The present application claims priority to U.S. Provisional Patent Application No. 61/944,840, filed on Feb. 26, 2014, the entire content of which is incorporated herein by reference.

FIELD

The present invention relates to methods and apparatus for introducing a solid or semi-solid intraocular drug-containing implant into the anterior chamber of an eye to thereby treat an ocular condition, such as ocular hypertension or glaucoma.

BACKGROUND

Extended-release drug delivery systems in the form of biodegradable intraocular implants, such as extruded implants, can provide an effective means for delivering therapeutically effective levels of a drug to the eye of patient suffering from an ocular condition. Various sites exist in the eye for implantation of a drug delivery system, including the vitreous, anterior and posterior chambers, as well as the intraretinal, subretinal, intrachoroidal, suprachoroidal, intrascleral, episcleral, subconjunctival, subtenon, intracorneal and epicorneal spaces. The particular site chosen for the drug implant may depend on the ocular condition and the region of the eye affected by the condition, and/or on the drug to be delivered. An ocular region of particular interest in some patients, such as those suffering from glaucoma and/or ocular hypertension, is the fluid-filled space in the eye known as the anterior chamber. Located between the iris and the innermost corneal surface or corneal endothelium, the anterior chamber contains structures such as the trabecular meshwork that regulate the drainage of aqueous humor. The balanced flow of aqueous humor from the ciliary processes in the posterior chamber, where it is produced, through the anterior chamber is essential for normal maintenance of intraocular pressure (IOP) in the eye.

Physical or biochemical factors that impair drainage of aqueous humor from the anterior chamber of the eye may lead to elevated intraocular pressure, or ocular hypertension, which may increase the risk for developing glaucoma. Therefore, a clinical goal in the treatment of glaucoma can be to reduce intraocular pressure. Conventional treatments for the reduction of IOP typically involve topical application of an IOP-lowering drug, which may act on tissues in the anterior chamber of the eye to promote the drainage of aqueous humor. Biodegradable, sustained-release drug delivery systems that can continuously deliver a therapeutically effective amount of an anti-hypertensive drug into the anterior chamber of the eye may be a useful and welcome alternative for some patients that rely on the regular daily instillation of ocular anti-hypertensives or other anti-glaucoma medications to control intraocular pressure and manage symptoms associated with glaucoma.

Intraocular drug delivery systems in the form of extruded implants for the sustained delivery of an IOP-lowering drug to the eye and methods and apparatus for administering a biodegradable drug delivery system into the vitreous body of an eye have been described. See, for example, U.S. Pat. No. 7,799,336, describing biocompatible intraocular implants containing a prostamide component and a biodegradable polymer for treating an ocular condition such as glaucoma, and U.S. Pat. No. 6,899,717, describing methods and apparatus for delivering bioerodible implants into various locations within the eye, particularly the vitreous of the eye, the entirety of both U.S. Patents are herein incorporated by reference.

However, the design of these and other intraocular implant delivery apparatus may be less than optimal for the large-scale manufacture of a sterile, pre-loaded, ready-to-use device that can be used safely and reliably to introduce an implant into the eye. In some cases, assembly of the apparatus may require a number of separate manufacturing and handling steps, from producing the separate housing components, to loading the implant, to final assembly of the device. Altogether, these steps can lengthen the time and increase the cost of production. Quality assurance also plays a large role in the cost and ease of manufacturing an implant delivery apparatus. Because of the small size and fragility of ocular implants, the means used for securely retaining an implant in the device during and after assembly is a key concern. In this regard, some apparatus may require intermediate checks and additional steps during and just prior to final assembly to ensure there is no loss of the implant during manufacture, which, while effective, are generally inefficient for the large-scale production of such devices. It would be preferable to have a device that permitted rapid visualization of the ocular implant within the device following assembly and prior to packaging and sterilization, as well as just prior to use to confirm the readiness of the device prior to shipping and use. An implant inspection window, for example, if available, would potentially not only increase the confidence in the batch-to-batch quality of the ocular implant delivery apparatus, but might substantially reduce the cost and boost the speed of manufacturing.

The apparatus described here meets these and other needs and is specifically designed for administration of a solid rod-shaped or filamentous intraocular implant into the anterior chamber of an eye.

SUMMARY

Described herein are methods and apparatus for safely and reliably introducing a solid drug formulation, such as filament or rod-shaped drug-containing implant, into the anterior chamber (or intracameral space) of the eye.

One embodiment provides for an apparatus for injecting an intraocular implant into the anterior chamber of a patient's eye, the apparatus comprising a) an elongate housing having a longitudinal axis and having a proximal end and a distal end; b) an ejector button extending through an opening in the housing and moveable from a first position to a second position in a direction normal (i.e., perpendicular) to the longitudinal axis of the housing; c) a needle having a proximal end and a distal beveled end, the needle extending longitudinally from the distal end of the housing and having a lumen extending through the length of the needle such that an intraocular implant can be received within and translated through the lumen of the needle, wherein the needle is rotatable in clockwise and counter-clockwise directions about its long axis (the imaginary segment containing the center of each end and extending the length of the needle and about which the volume of the needle is symmetrically arranged); and d) an implant holder having a proximal and distal end and a lumen capable of receiving an intraocular implant and holding the implant prior to activation of the apparatus, the implant holder capable of movement, upon activation of the apparatus, from a first position to a second position within the housing along the longitudinal axis of the housing, the lumen of the holder aligned with the lumen of the needle such that an implant can slidably translate from the lumen of the implant holder into the lumen of the needle upon activation of the device, and the implant holder capped at its distal end with a slit, cross-slit, or perforated membrane. The slit, cross-slit, or perforated membrane prevents the implant from prematurely exiting or falling out the distal end of the implant holder during assembly, packaging, sterilization, and shipping of the apparatus and prior to activation of the apparatus and thereby blocks translational movement of the implant from the implant holder to the lumen of the needle prior to activation of the device. However, the slit, cross-slit, or perforated membrane opens upon activation of the device to permit passage of the implant from the implant holder to the needle upon activation of the device. The slit(s) and/or cross-slits or perforation(s) are included in the membrane to allow for separation of sections of the membrane surrounding and covering the lumen opening at the distal end of the implant holder. The central section of the membrane covering the distal end of the implant holder lumen can open, or fold back and away from the distal end of the implant holder when the membrane is moved against a forward element of the apparatus (e.g., the needle hub), as occurs upon activation of the apparatus. The implant holder is located adjacent to the proximal end of the needle and the lumen of the implant holder is aligned with the lumen of the needle so as to permit an intraocular implant in the holder to slidably translate from the holder into the lumen of the needle. The device can be activated, and an implant held by the device can be ejected, by manually pressing the ejector button.

A push rod is provided for driving an implant out of the implant holder and through the lumen of the needle and, ultimately, out the distal end of the needle. The distal end of the needle is beveled so it can easily pierce the cornea of the eye with minimal trauma. The push rod is disposed longitudinally in the housing and is receivable within the lumen of the implant holder and is capable of translational movement along the longitudinal axis of the housing from a first position within the lumen of the implant holder to a second position within and through the needle lumen. In the pre-activation state of the apparatus, the distal end of the push rod is located in the lumen of the implant holder.

A spring-driven assembly, consisting of or comprising a spring and a release lever, is included, and is located inside the housing in the proximal half of the apparatus, to force the push rod forward along the longitudinal axis of the housing toward the distal end of the apparatus. Accordingly, the spring generates a force that is aligned with the longitudinal axis of the housing. In some embodiments, the force with which the implant is driven out of the implant delivery device by the spring-driven assembly does not depend on the pressure applied to the ejector button.

In some embodiments, externally located needle-rotation knob is positioned at the proximal end of the housing. The knob is operably connected to the needle at the distal end of the apparatus by a metal connecting rod. The knob can be twisted in a clockwise or counter-clockwise direction, relative to the longitudinal axis of the housing, to rotate the needle in a corresponding clockwise and counterclockwise direction, as desired.

The housing can comprise a cover top, a cover bottom, and a nose cone. The nose cone is located at the distal end of the housing. A needle bevel orientation assembly (also referred to as the needle rotation assembly) is located at the proximal end of the housing. The needle bevel orientation assembly includes the needle-rotation knob and is for manually rotating the needle, and therefore the needle bevel, in a clockwise or counter-clockwise direction relative to the long axis of the device prior to use and activation of the device. The housing can further contain implant inspection windows, which can be located in the nose cone at the distal end of the housing, for viewing the implant within the manufactured and sterilized apparatus. The implant inspection windows can permit visual observation of the implant inside the housing prior to activation of the apparatus. Two implant inspection windows may be present on the nose cone, with one window located on one side of the nose cone and a second window located on the opposing side of the nose cone. In some embodiments, an optical element (for example, a lens) is included in the safety cap or the implant inspection windows or both to magnify the view of the implant inside the apparatus, and specifically, inside the implant holder. This may aid in the detection and visual observation of the implant.

Additionally, according to some embodiments, the apparatus can further comprise an implant delivery feedback window, located on the housing and providing for observation of a visible signal that indicates activation of the apparatus. More specifically, an implant delivery feedback window may be included in the cover bottom or cover top to provide visual signals to the user that the apparatus has been activated (i.e., that the energy stored in the spring-driven assembly inside the housing has been released, as occurs, for example, when the ejector button is depressed). Examples of visual signals can include changes in symbol(s) or letter(s), pattern or color changes, or any combination thereof. According to one embodiment, the housing cover bottom contains two separate delivery feedback windows, located on opposing sides of the cover bottom.

The implant delivery apparatus can comprise a solid, drug-containing intraocular implant such as an extruded biodegradable drug-containing intraocular implant, which is one type of drug delivery system. In the present invention, the implant is entirely contained within (i.e., disposed within) the implant holder prior to activation of the apparatus. The implant does not enter the lumen of the needle until the device is activated. Similarly, the push rod does not enter or translate into the lumen of the needle until the device is activated. The implant can be a rod-shaped, biodegradable implant that releases a drug for an extended period such as, for example, 30 days or more. The implant can comprise a pharmaceutically active agent (drug) effective for treating a medical condition of the eye. In some embodiments, the intraocular implant comprises an intraocular pressure (IOP)-lowering drug such as, for example, bimatoprost or other prostamide (Woodward et al. (2008) "Prostamides (prostaglandin-ethanolamides) and their pharmacology"*British Journal of Pharmacology* 153 (3):410-19). Examples include, but are not limited to, the prostamides described in U.S. Pat. No. 7,799,336, which is herein incorporated by reference in its entirety. The drug-containing intraocular implant can be sized and configured to be receivable in and deliverable through a 28 gauge or higher gauge needle. One example of an intraocular implant is a rod-shaped biodegradable implant produced by an extrusion process with a diameter and length suitable for delivery through the needle and suitable for placement in the anterior chamber of the eye. Thus, in one embodiment the implant delivery apparatus comprises an intracameral implant. The intraocular or intracameral implant can comprise a biodegradable polymer matrix and a pharmaceutically active agent associated with the biodegradable polymer matrix. The pharmaceutically active agent can be effective for treating a medical condition of the eye, and the implant can be 150 μm to 300 μm in diameter or width, 0.50 mm to 2.5 mm in length, and 20 μg to 120 μg in total weight.

The intraocular implant delivery apparatus with the drug-containing implant may be manufactured in a ready-to-use, sterile form.

The implant delivery apparatus in accordance with this disclosure comprises a beveled needle, extending longitudinally from the distal end of the apparatus. The beveled end of the needle forms a sharp point that can easily penetrate the eye. The needle gauge may range from 22 gauge to 30 gauge. In some embodiments, the beveled needle (i.e., a needle with beveled tip) needle is a 25 gauge, 27 gauge, 28 gauge, or 29 gauge needle. Additionally, the needle can be a thin wall (TW) or ultra-thin wall (UTW) needle. Smaller needles (e.g., 28 gauge or higher gauge needles) can be used for injection of an implant into the anterior chamber of the eye. According to some embodiments, the length of the bevel, from the tip of the needle to the heel of the bevel, is 2 mm in length. However, various bevel lengths are possible with the presently described apparatus. The intraocular implant delivered with the present device should be sized and configured such that it can slidably translate through the lumen (or bore) of the needle. Similarly, the lumen of the implant holder is sized to receive and hold the intraocular implant. Examples include rod-shaped implants having a diameter or width that permits the implant to be received in and delivered through the lumen (or bore) of the needle.

The use of needles with smaller outer diameters and the ability to orient the bevel of the needle with a rotation knob rather than having to alter the grip on the apparatus provides added control for self-sealing methods of implant delivery into the anterior chamber of an eye.

Accordingly, one embodiment is a method for introducing an intraocular implant into the anterior chamber of an eye using the presently disclosed apparatus. The method can comprise providing an intraocular implant delivery apparatus according to the present disclosure having a needle with a proximal end and a distal beveled end and comprising an intracameral implant, penetrating the cornea of the eye with the distal end of the needle and inserting the needle into the anterior chamber of the eye, ejecting the implant from the apparatus into the anterior chamber of the eye, and then removing the needle from the patient's eye. Preferably, the puncture created by the insertion of the needle into the eye is self-sealing upon the removal of the needle. Particular orientations of the needle (e.g., bevel away from the surface of the cornea) during insertion can aid in self-sealing. For example, the penetrating step can comprise inserting the needle into the cornea with the bevel of the needle oriented 180° away from the surface of the eye or cornea. According to one embodiment, the method and apparatus as set forth herein are used to introduce an intraocular implant (or more particularly, an intracameral implant) into the anterior chamber of a patient's eye. The patient can be a human patient in need of treatment for a medical condition of the eye.

The needle tip can further be configured to have particular beveled designs which further aid in the self-sealing method. In some forms of the method, the patient can have glaucoma or ocular hypertension. One or more markings are optionally present on the exterior of the needle as an aid to measure needle advancement into the eye. In one form of the method, the needle is inserted into the anterior chamber of the eye by inserting the needle through the cornea at a point just anterior to the limbus (or corneo-scleral junction, where the cornea joins the sclera and the bulbar conjunctiva attaches to the eyeball). According to some embodiments, the needle is inserted into the anterior chamber to a depth of about 4 mm to about 7.5 mm, as measured from the tip of the needle to the corneal surface where the needle first penetrates the eye. The needle may be pointed toward the inferior anterior chamber angle before ejecting the implant. In one embodiment, the needle is advanced into the eye to a length of about 4 mm, as measured from the tip of the needle to the outer surface of the eye where the needle first penetrates the eye, and the tip of the needle is pointed toward the inferior anterior chamber angle. The ejector button is then depressed to deploy the implant. The method may be effective for treating a medical condition of the eye. For example, the method may be effective for treating glaucoma, ocular hypertension (or elevated intraocular pressure), dry eye, or age-related macular degeneration.

An apparatus according to the present disclosure can include an implant holder for holding and retaining an implant during assembly and prior to activation of the ocular implant apparatus. Unlike some other devices, the implant is not stored in the lumen of the needle but is instead held in the lumen of an implant holder, a separately manufactured element located adjacent to the proximal end of the needle inside the housing. During assembly, the distal end of the push rod is inserted into the lumen of the implant holder and implant loss is prevented during that step by the presence of a foil membrane affixed to the opposite end of the holder. The membrane is opened during activation of the device (as explained in more detail below), but does not open during assembly or storage of the device. The implant holder simplifies the final assembly of the device and renders measures such as notching, crimping or plugging of the needle unnecessary, making possible the use of thinner, higher gauge needles such as 28 gauge, 29 gauge, or 30 gauge or higher gauge needles. According to some embodiments, in the present apparatus the needle is not notched, crimped, or clamped, and an O-ring or the like is not placed on the needle during or after assembly of the apparatus. Moreover in some embodiments, the needle is not plugged or capped with any material to prevent loss of the implant during assembly or storage of the device.

The present apparatus may include implant inspection windows on the nose cone and the needle hub (described in more detail below) so that the manufacturer and physician can verify the presence of an intraocular implant inside the device following assembly and prior to use of the device simply by looking through the window. This, too, can speed the manufacturing process and lower the cost of goods, since it may not only permit quick and easy visual inspection during assembly but may also permit an automated form of implant inspection during the quality assurance stage of manufacture. The implant inspection window also provides for a valuable final check by the end-user, the physician for example, to confirm the readiness of the apparatus.

Additional embodiments provide for safety features which include, among other things, a safety cap that protects the needle and those handling the apparatus during packaging, shipping, and use, and that also blocks the premature, unintended depression of the ejector button at any of these stages. The present apparatus may also include a delivery feedback window on the side of the housing, through which one or more visible signals are communicated to the user that the apparatus has been activated and that an implant has been successfully ejected.

The present apparatus may also employ a system which uses pre-set, fixed-force with which the implant is ejected. In the present apparatus, the force of implant ejection (and thus the distance the implant is ejected away from the tip of the needle in liquid medium such as the anterior chamber of the eye upon activation of the apparatus) is not proportional to and does not depend on the force applied to the ejector button by the user. The spring-driven assembly inside the apparatus generates a force against the push rod that depends on the spring constant and the degree of compression on the spring. Depression of the ejector button unlocks the spring but does not contribute to the force of implant ejection. This design may reduce variability in the implant administration procedure and provides for a more controlled and more reproducible means of delivering implants into the eye. The spring-driven design in the present apparatus is particularly well-suited for injection of an implant into the anterior chamber of the eye (i.e., intracameral administration of an implant) since it helps ensure clean separation of the implant from the apparatus into the fluid-filled environment of the anterior chamber of the eye and a consistent ejection distance within the limited space of the anterior chamber of the eye The intraocular delivery apparatus and its advantages according to this disclosure can be further understood by reference to the following figures and detailed description.

BRIEF DESCRIPTION OF THE DRAWINGS

These and other features will now be described with reference to the drawings summarized below. These drawings and the associated description are provided to illustrate one or more embodiments and not to limit the scope of the invention.

FIG. 1A shows a perspective view of an example embodiment of the assembled apparatus. The Distal and Proximal ends of the apparatus are indicated in the drawing.

FIG. 1B shows a perspective exploded view of the assembled apparatus with the safety cap removed.

FIG. 4 depicts the apparatus in perspective and shows how the user may rotate the needle by twisting knob 52 at the proximal end of the apparatus.

FIG. 7A shows a side cross-sectional view of the nose cone, needle hub assembly (including the needle hub and beveled needle), and implant holder before depression of the ejector button. Also shown is the push rod and implant in the implant holder and the membrane affixed to the distal end of the implant holder.

FIG. 7B shows the side cross-sectional view of FIG. 7A after depression of the ejector button. The view shows how the implant holder membrane may fold back into the empty space in the implant holder when the implant holder is forced against the nipple inside the needle hub. The arrow shown at the right of the figure indicates the direction of movement of the push rod during implant ejection.

FIG. 9A shows a perspective view of the internal assemblies of the apparatus, including the needle rotation assembly 78, the push rod guide and conveyor, as well as the needle hub and beveled needle extending from the distal end of the needle hub. The dotted outline indicates the location of the housing relative to the components. The wide, double-headed arrows show how the various components and assemblies inside the housing rotate in response to the rotation of the needle-rotation knob 52 at the proximal end of the apparatus.

FIG. 9B shows an enlarged perspective view of the beveled needle. The dotted, double-headed arrow indicates how the needle is rotatable in both clockwise and counter-clockwise directions in the assembled apparatus.

FIG. 10A shows a top view of the underside or interior of the housing cover bottom 48.

FIG. 10B shows a side cross-sectional view of the distal end of the housing cover bottom, showing the location of the rubber post 154 at the distal end of the track 140 in the cover bottom.

FIG. 10C shows a perspective view of the inside (interior) of the housing cover bottom.

FIG. 11A shows the underside or interior of the housing cover top 46.

FIG. 11B shows a perspective cross-sectional view of the housing cover top with the ejector button installed.

FIG. 11C shows a perspective view of the interior of the housing cover top.

FIG. 12A shows a perspective view of the needle hub assembly, including the beveled needle and the needle hub. The needle is overmolded with the needle hub and is therefore permanently secured to and rotatable in unison with the needle hub.

FIG. 12B shows a top view of the needle hub assembly.

FIG. 12C shows a side view of the needle hub assembly.

FIG. 12D shows an end view of the needle hub assembly, showing the interior of the needle hub, the nipple 62 located inside the needle hub, and the inner passageway 59 inside the nipple leading to the lumen of the needle. The ribs 100 inside the needle hub that grab or engage with implant holder can also be seen in this end-on view.

FIG. 12E shows a perspective view of the needle hub assembly and the interior of the needle hub in perspective.

FIG. 13 shows an exploded perspective view of the safety cap, nose cone, needle and needle hub (needle hub assembly), membrane, and implant holder.

FIGS. 14A and B show perspective views of the release lever.

FIG. 16A shows a perspective view of the nose cone.

FIG. 16B shows a top view of the nose cone.

FIG. 16C shows a side view of the nose cone.

FIG. 16D shows a bottom view of the nose cone.

FIG. 16E shows an end view of the nose cone, showing the interior of the nose cone.

FIG. 17A shows a side view of the apparatus prior to activation of the apparatus (i.e., prior to depression of the ejector button). The spring is shown compressed against the distal end of the knob shaft. The housing of the apparatus is shown in cross-section.

FIG. 17B shows a top view of the distal end of the apparatus, with the safety cap removed, and prior to ejection of the implant (i.e., prior to activation of the apparatus). Shown is the needle extending from the nose 80 of the needle hub 58 and the nose cone in connection with the cover top. The intraocular implant 68 can be seen through the implant inspection window 112 in the nose cone. The boss section 94 of the ejector button extending up through the cover top can also be seen.

FIG. 17C shows a cross-sectional side view of the apparatus, with the safety cap removed, and prior to activation of the apparatus. The spring 134 is shown compressed against the knob shaft.

FIG. 18A shows a perspective view of the ejector button.

FIG. 18B shows perspective view of the ejector button.

FIG. 18C shows a front (distal) end view of the ejector button.

FIG. 18D shows a top view of the ejector button.

FIG. 18E shows a side view of the ejector button.

FIG. 20A shows a side view of the apparatus in section prior to depression of the ejector button and, thus, prior to activation of the apparatus. Compare with post-activation view shown in FIG. 21A.

FIG. 20B shows a side view of the distal half of the apparatus in section prior to activation of the apparatus. The black single-headed arrow over the ejector button indicates the direction the button moves (i.e., downward, or in a direction normal to the longitudinal axis of the housing) when depressed by the user. Compare with post-activation cross-sectional view shown in FIG. 21B.

FIG. 21A shows a side view of the apparatus in section after depression of the ejector button and, thus, after activation of the apparatus.

FIG. 21B shows an enlarged side view of the distal half of the apparatus in section after activation of the apparatus.

FIG. 25A shows a perspective view of the individual components of the apparatus and the connections therebetween.

FIG. 25B depicts a helical or coiled progressive spring.

FIG. 26A shows a top view of the release lever.

FIG. 26B shows a side view of the release lever.

FIG. 26C shows a bottom view of the release lever.

FIG. 27A shows a top view of the push rod guide.

FIG. 27B shows a side view of the push rod guide.

FIG. 27C shows an enlarged bottom view of the push rod guide.

FIG. 27D shows the distal end of the push rod guide.

FIG. 27E shows the proximal end of the push rod guide, which is configured to receive the distal end of the metal connecting rod 148.

DETAILED DESCRIPTION

Definitions

Figure 1C:
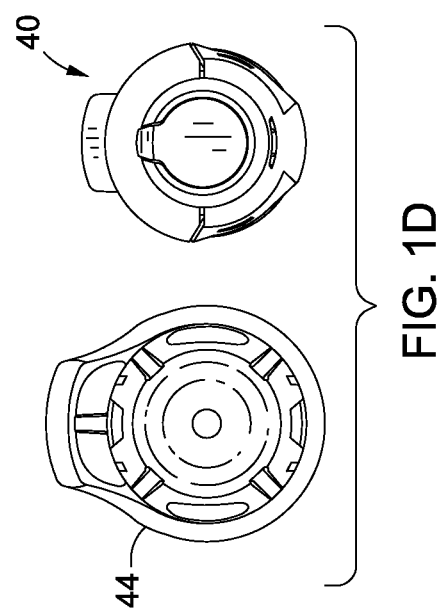
FIG. 1C shows a front view of the safety cap (left) and a front view of the implant delivery apparatus (right) with the safety cap removed.
Figure 1D:
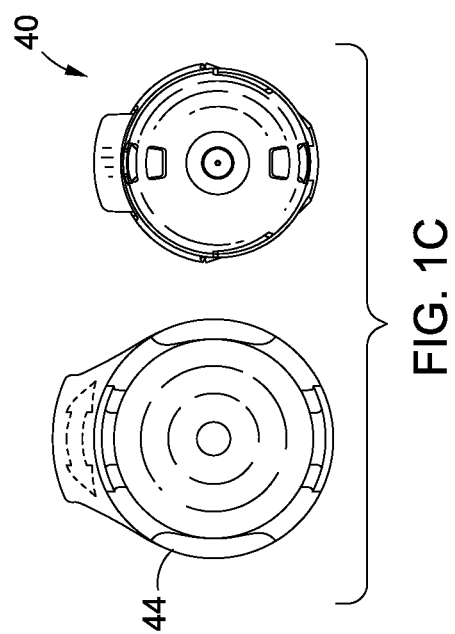
FIG. 1D shows an end view of the safety cap (left) and an end view of the implant delivery apparatus (right) with the safety cap removed.

The term "plurality" means two or more.

The term "patient" means a human or non-human mammal in need of treatment for a medical condition of the eye.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of ocular regions in the eye include the anterior chamber, the posterior chamber, the vitreous cavity, the vitreous body, the choroid, the suprachoroidal space, the conjunctiva, the subconjunctival space, the sub-tenon space, the episcleral space, the intracorneal space, the epicorneal space, the sclera, the pars plana, surgically-induced avascular regions, the macula, and the retina.

An "intraocular implant" refers to a solid or semi-solid drug delivery system or element that is sized and configured to be placed in an ocular region of the eye, including, for example, the anterior chamber. Other ocular regions of the eye into which an intraocular implant can be placed include the vitreous body, subconjunctival space, and subtenon space. Intraocular implants may be placed in an eye without significantly disrupting vision of the eye. Examples of an intraocular implant include extruded biodegradable filaments, such as a rod-shaped implant produced by a hot-melt extrusion process, comprising a biodegradable polymer matrix and a pharmaceutically active agent, associated with the polymer matrix, and cut to a length suitable for placement in an eye. Intraocular implants are biocompatible with the physiological conditions of an eye and do not cause adverse reactions in the eye. In certain forms of the present invention, an intraocular implant may be configured for placement in the anterior chamber, posterior chamber, subconjunctival space, or vitreous body of the eye. Intraocular implants can be biodegradable and may be configured in the form of a cylindrical or non-cylindrical rod produced by an extrusion process. According to some embodiments, the intraocular implant may comprise an active agent effective for treating a medical condition of the eye.

An "intracameral" implant is an intraocular implant that is sized and configured for placement in the anterior chamber of the eye. The anterior chamber refers to the space inside the eye between the iris and the innermost corneal surface (endothelium). An intracameral implant is also an intraocular implant that can fit into the anterior chamber angle (iridocorneal angle) of the eye without contacting the corneal endothelium and thereby without causing corneal trauma, inflammation, or edema, or iris chaffing. One example of an intracameral implant is a hot-melt extruded, biodegradable, rod-shaped filament comprising or consisting of a biodegradable polymer matrix and an active agent associated with the polymer matrix and cut to a length suitable for placement in the anterior chamber of a mammalian eye (for example, a human eye). A rod-shaped intracameral implant can be 0.5 mm to 3 mm in length and 0.05 mm to 0.5 mm in diameter or maximum width in the case of non-cylindrical rods. An intracameral implant is usually between 20 μg and 150 μg in total weight and can fit into the anterior chamber angle (iridocorneal angle) of the eye without contacting the corneal endothelium and thereby without causing corneal trauma, inflammation, or edema, or iris chaffing. For example, the intracameral implant delivered with the present apparatus into the anterior chamber of a mammalian eye, such as a human eye, can be 0.5 mm to 2.5 mm in length, 0.15 mm to 0.3 mm in diameter, and 20 μg to 120 μg in total weight.

The intracameral implant is preferably deliverable through a 27 gauge, 28 gauge, 29 gauge, or 30 gauge needle. The inner diameter of the needle may vary, depending on whether the needle is a standard or ultra (or extra) thin-wall needle. The diameter, width, or cross-sectional area of the implant should be receivable in the lumen of the needle so that the implant can slidably translate through the lumen of the needle.

An "intravitreal" implant is an intraocular implant that is sized and configured for placement in the vitreous body of the eye. The vitreous body of the eye may accommodate implants larger than those used for the anterior chamber.

The terms "device" and "apparatus" are synonymous and used interchangeably herein to refer to the present intraocular implant delivery apparatus (device), depicted in the attached drawings.

The term "about" means that the number, range, value, or parameter so qualified encompasses ten percent more and ten percent less of the number, range, value, or parameter.

The term "biocompatible" means compatible with living tissue or a living system. Biocompatible implants and polymers produce few or no toxic effects, are not injurious, or physiologically reactive and do not cause an immunological reaction.

The terms "ocular condition" and "medical condition of the eye" are synonymous and used interchangeably herein and refer to a disease, ailment, or condition which affects or involves the eye or one of the parts or regions of the eye, including the anterior or posterior regions of the eye. The eye is the sense organ for sight. Broadly speaking the eye includes the eyeball and the tissues and fluids which constitute the eyeball, the periocular muscles (such as the oblique and rectus muscles) and the portion of the optic nerve which is within or adjacent to the eyeball. Non-limiting examples of a medical condition of the eye (i.e., ocular condition) within the scope of the present disclosure include ocular hypertension (or elevated intraocular pressure), glaucoma, dry eye, and age-related macular degeneration. Glaucoma in a patient may be further classified as open-angle glaucoma or angle-closure glaucoma. In one possible method, the patient receiving an intracameral drug-containing implant using an apparatus according to this disclosure may have or be specifically diagnosed with primary open-angle glaucoma. A given patient having open-angle glaucoma may have low, normal, or elevated intraocular pressure. Other forms of glaucoma within the present disclosure include pseudoexfoliative glaucoma, developmental glaucoma, and pigmentary glaucoma.

"Associated with a biodegradable polymer matrix" means mixed with, dissolved and/or dispersed within, encapsulated by, surrounded and/or covered by, or coupled to.

The term "biodegradable," as in "biodegradable polymer" or "biodegradable implant," refers to an element, implant, or a polymer or polymers which degrade in vivo, and wherein degradation of the implant, polymer or polymers over time occurs concurrent with or subsequent to release of the therapeutic agent. A biodegradable polymer may be a homopolymer, a copolymer, or a polymer comprising more than two different structural repeating units. The terms biodegradable and bioerodible are equivalent and are used interchangeably herein.

"Active agent," "drug," "therapeutic agent," "therapeutically active agent," and "pharmaceutically active agent" are used interchangeably herein to refer to the chemical compound, molecule, or substance that produces a therapeutic effect in the patient (human or non-human mammal in need of treatment) to which it is administered and that is effective for treating a medical condition of the eye.

The term "patient" can refer to a human or non-human mammal in need of treatment of a medical condition of the eye.

The term "treat", "treating", or "treatment" as used herein, refers to reduction, resolution, or prevention of an ocular condition, ocular injury or damage, or to promote healing of injured or damaged ocular tissue. A treatment is usually effective to reduce at least one sign or symptom of the ocular condition or risk factor associated with an ocular condition.

For purposes of describing the present apparatus, the term "proximal" refers to the end of the apparatus or apparatus component that is closest to the needle-rotation knob 52 and that is farthest from the patient when the apparatus is in use with the needle in contact with the patient's eye.

The term "distal" refers to the end of the device or device component that is closest to the patient when the device is in use, with the needle in contact with the patient's eye. For example, the beveled tip (or sharp end) of the needle is located at the distal end of the needle and at the distal end of the implant delivery device. The farthest distal end of the device may be referred to as the distal sharp end of the device, since the needle extends or projects from the distal end of the device. The needle-rotation knob 52 is at the proximal end of the implant delivery device. In this context, the orientation and connections between components within the device may be described herein by reference to the distal and proximal ends of the various components. The distal end being the end of the component that is located closest to the distal end of the housing or device and the proximal end being the end located closest to the proximal end of the housing or device in the assembled device.

As used herein, "self-sealing" methods of delivering intraocular implants into the eye refers to methods of introducing implants through a needle and into desired locations of a patient's eye without the need for a suture, or other like closure means, at the needle puncture site. Such "self-sealing" methods do not require that the puncture site (where the needle penetrates the eye) completely seal immediately upon withdrawal of the needle, but rather that any initial leakage is minimum and dissipates in short order such that a surgeon or another equally skilled in the art, in his or her good clinical judgment, would not be compelled to suture or otherwise provide other like closure means to the puncture site.

Figure 2:
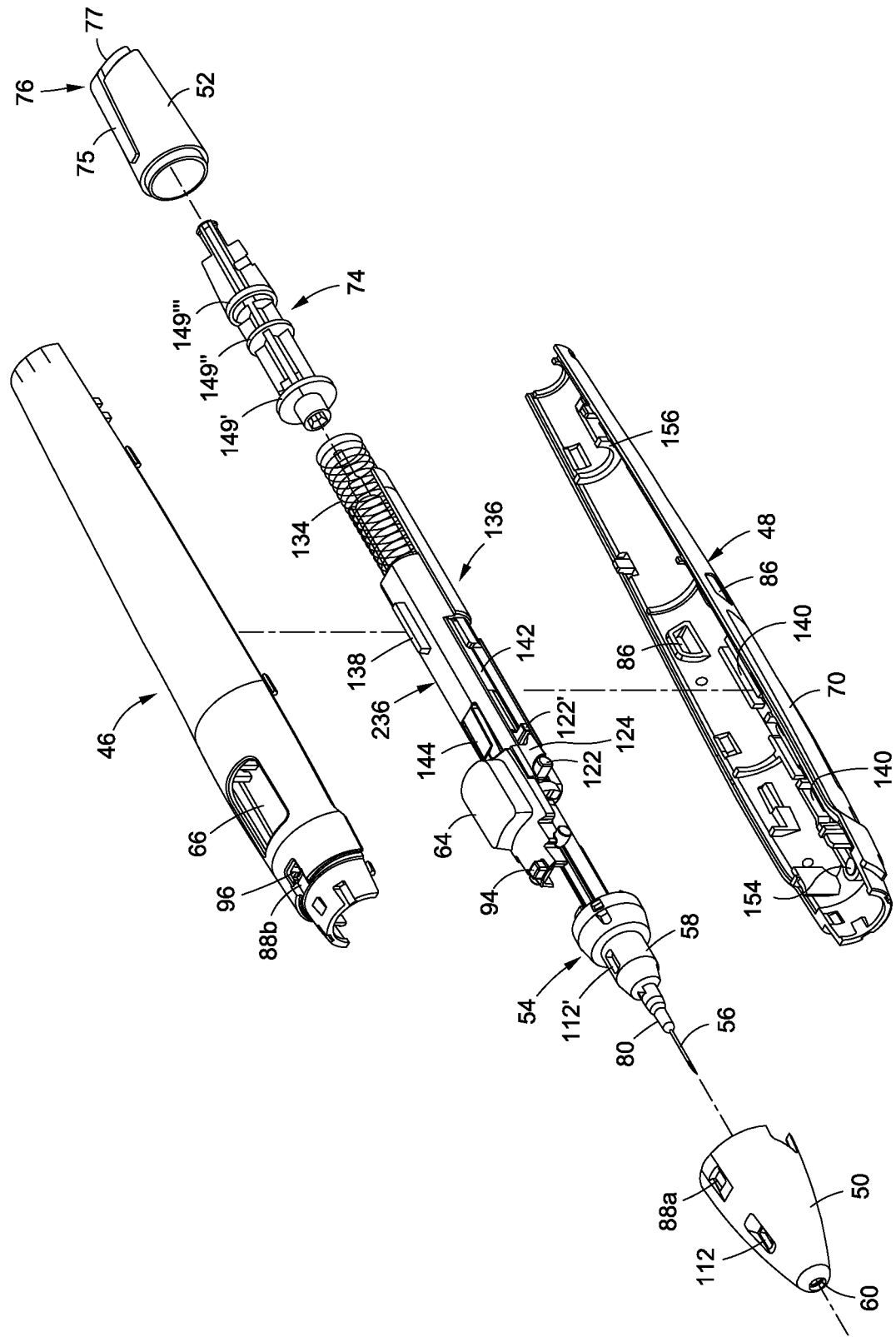
FIG. 2 shows a perspective exploded view of the implant delivery apparatus.

An embodiment of an intracameral implant delivery apparatus according to this disclosure is depicted in FIGS. 1A-D. As shown in FIGS. 1A-1D, the intraocular implant delivery apparatus 40 is ergonomically configured for easy gripping and manipulation and has the general overall shape of a pen or other writing instrument. From FIGS. 1A-1D it can be seen that the apparatus includes an external housing 42 and a safety cap 44, which attaches to the distal end of the housing. Referring to FIG. 2, it can be seen that housing 42 is formed of a cover top 46, a cover bottom 48, and a nose cone 50. These sections may be manufactured as separate pieces and then secured or snapped together. The sections are preferably configured to snap-fit together, although other known methods of attachment are contemplated, including, e.g., gluing, welding, fusing, etc. Cover top 46 snaps onto cover bottom 48 and nose cone 50 is configured for receipt over and attachment to (e.g., snaps onto) cover top 46 and cover bottom 48, as is apparent from FIGS. 2 and 3. A needle-rotation knob 52, which allows the user to rotate the needle 56 as shown in FIG. 4, extends from the proximal end of the housing.

Figure 3:
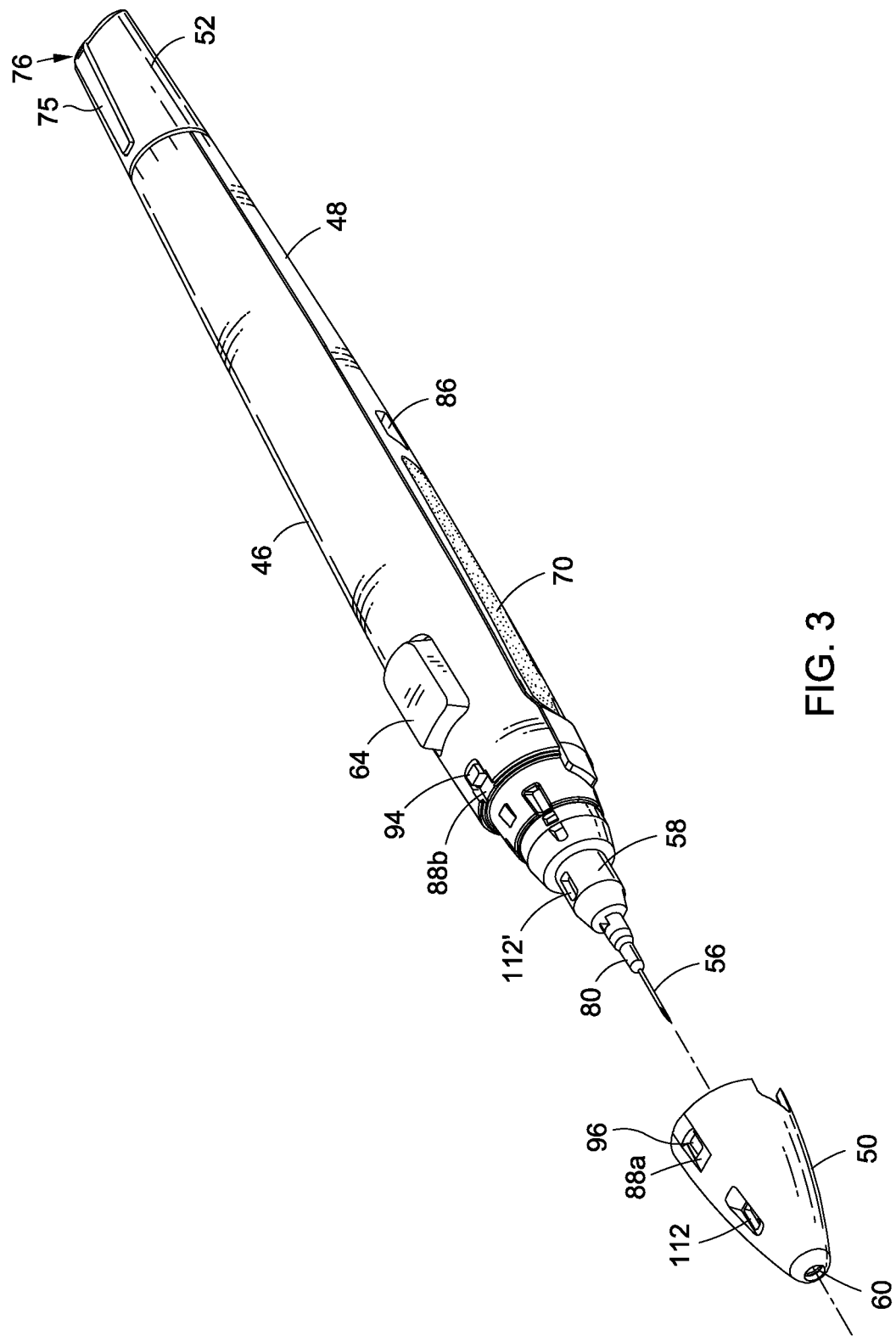
FIG. 3 shows a perspective exploded view of the apparatus with the nose cone removed.
Figure 5A:
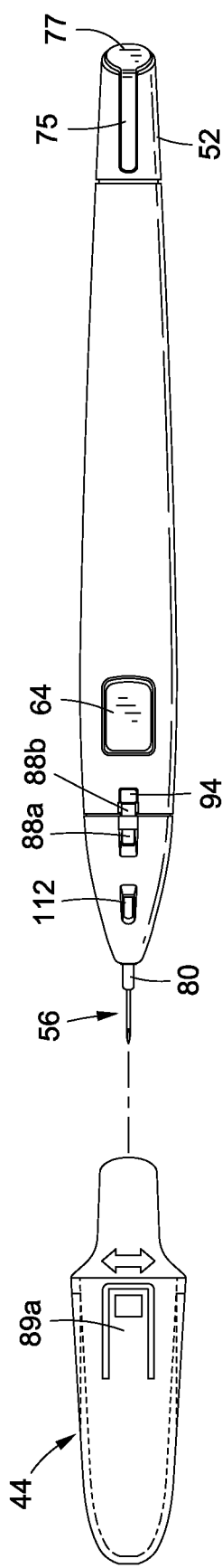
FIG. 5A shows a top view of the apparatus with the safety cap removed.
Figure 5B:
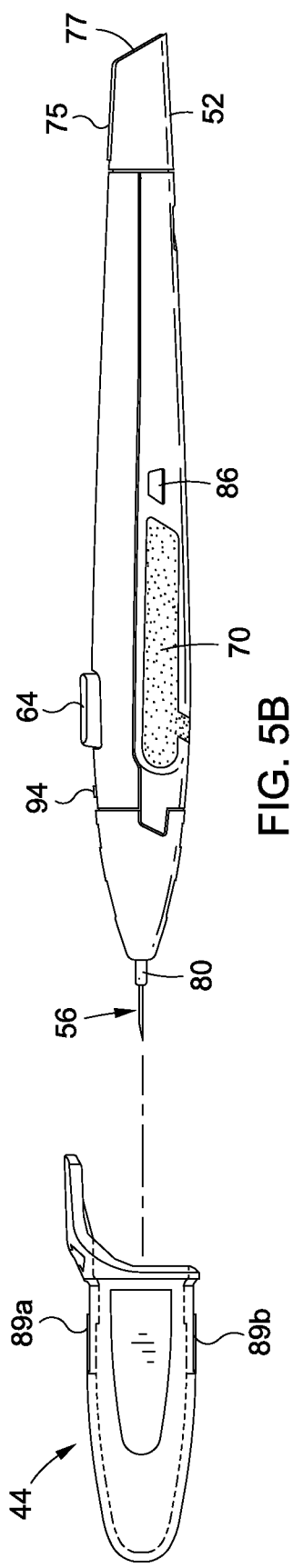
FIG. 5B shows a side view of the apparatus with the safety cap removed.
Figure 5C:
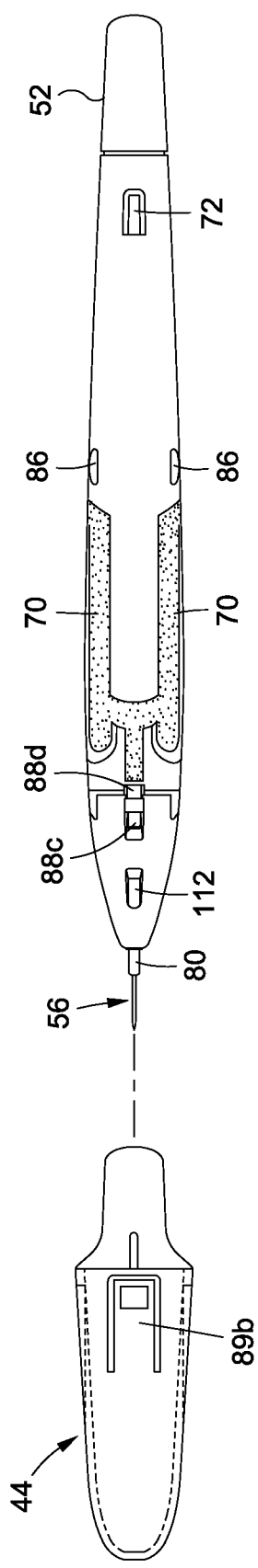
FIG. 5C shows a bottom view of the apparatus with the safety cap removed.
Figure 6:
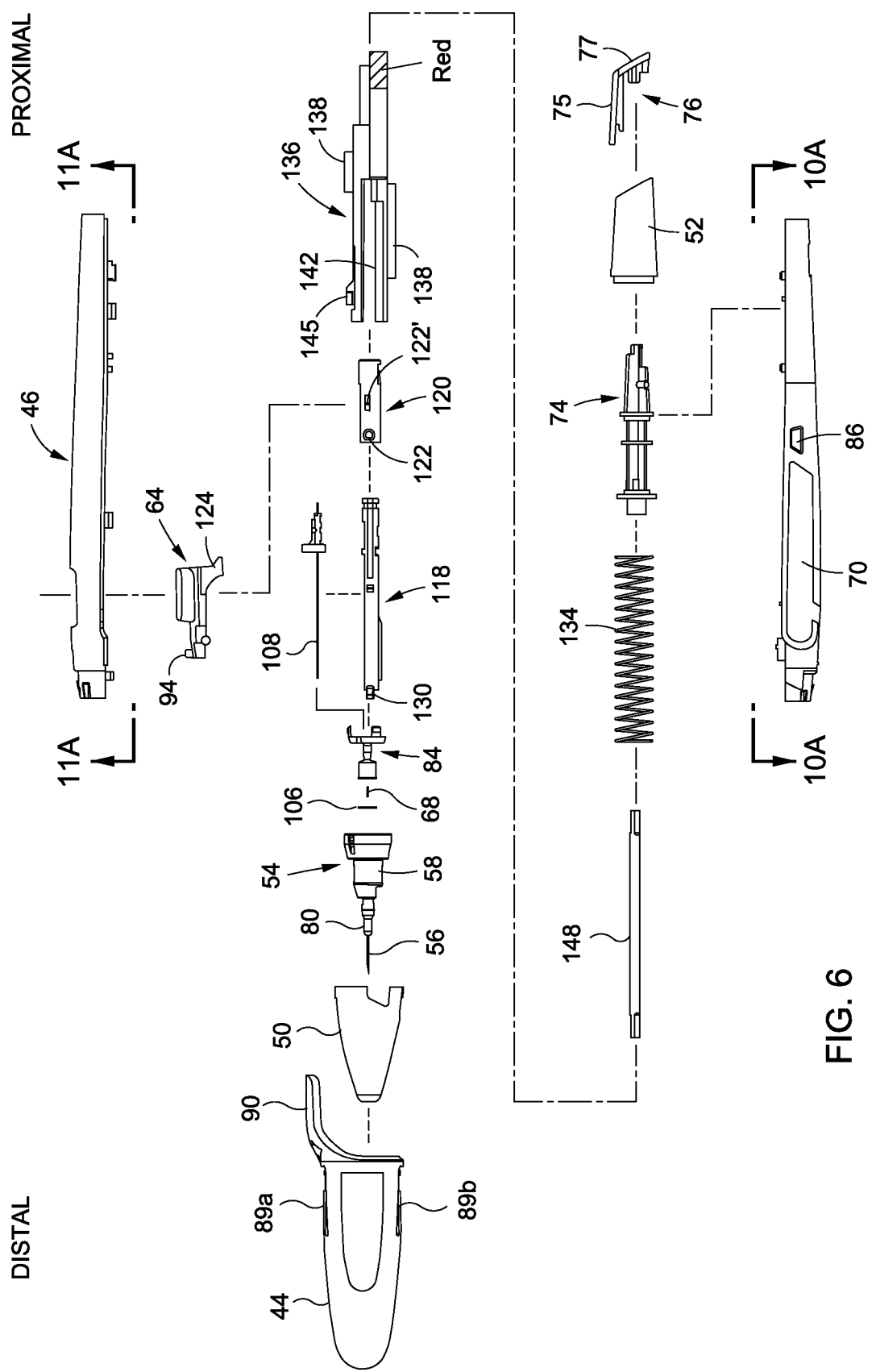
FIG. 6 shows a side exploded view of the apparatus, showing a side view of each of the individual parts of the apparatus.

As seen in FIGS. 1A-5C, nose cone 50 forms the distal end of the housing 42. As seen in FIGS. 2, 3, and 6, nose cone 50 receives needle hub assembly 54, which can include i) a needle 56 having a beveled tip 57, also referred to herein as beveled needle 56 or rotatable needle 56, and ii) a needle hub 58. As can be seen in FIGS. 1A-1D, 2, 3, 6, and 7A-7B, needle 56 is attached to and extends from needle hub 58, which is receivable in nose cone 50. In one embodiment, needle 56 is overmolded with or bonded to needle hub 58. Needle hub 58 is configured for receipt within nose cone 50, with beveled needle 56 extending through an opening 60 in nose cone 50 (FIG. 3). As shown in the enlarged, cross-section views of FIGS. 7A-7B, the lumen of beveled needle 56 is in communication with a cone-shaped inner passageway 59 in nipple 62 present within needle hub 58, such that a rod-shaped intracameral implant 68 may slidably translate into nipple 62 and through passage 59 into the lumen of needle 56. Needle hub 58 is rotatable in clockwise and counterclockwise directions (relative to the longitudinal axis of the housing) inside nose cone 50. Accordingly, beveled needle 56, extending through nose cone opening 60, is rotatable in the same directions since needle 56 is bonded to or otherwise fixedly secured to needle hub 58.

As can be seen in FIGS. 1A-6, an ejector button 64 extends through an opening 66 in the housing. More specifically, ejector button 64 extends through an opening 66 in cover top 46.

The apparatus 40 can contain an intracameral implant 68 and may be used to introduce the implant into the anterior chamber of a patient's eye. Depression of ejector button 64 activates the apparatus, thereby causing ejection of the implant from the apparatus. The implant exits through the needle of the apparatus.

Figure 8A:
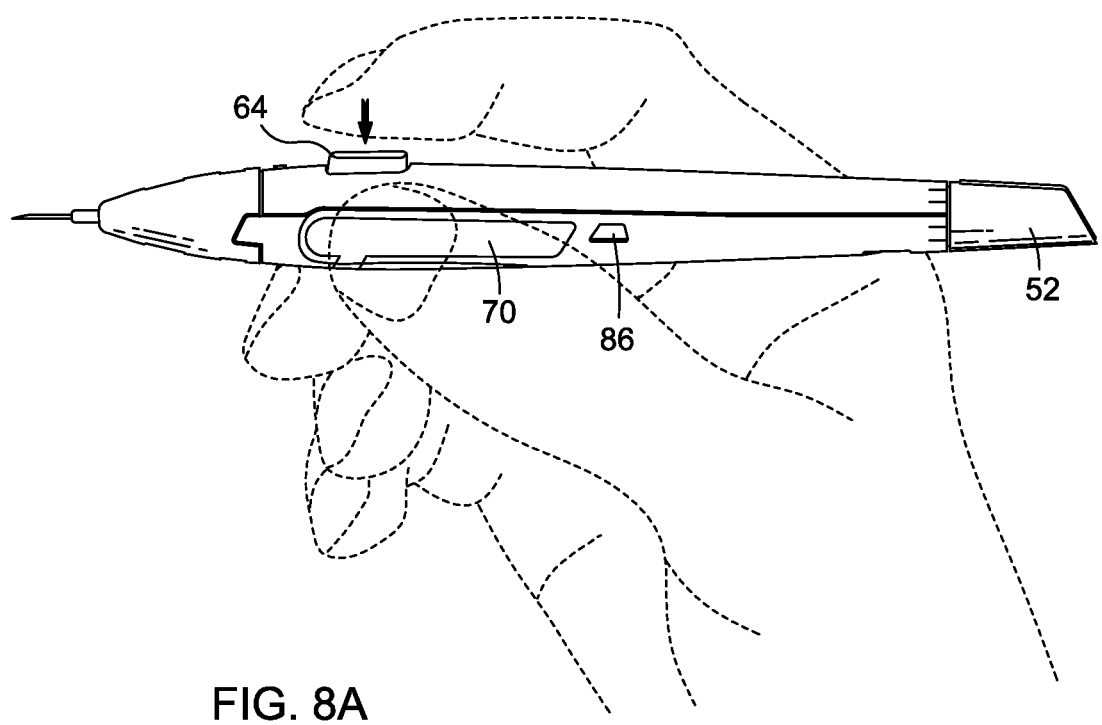
FIGS. 8A and 8B show examples of how the apparatus may be held and activated by the user during use of the apparatus to deliver an implant into the eye of a patient.
Figure 8B:
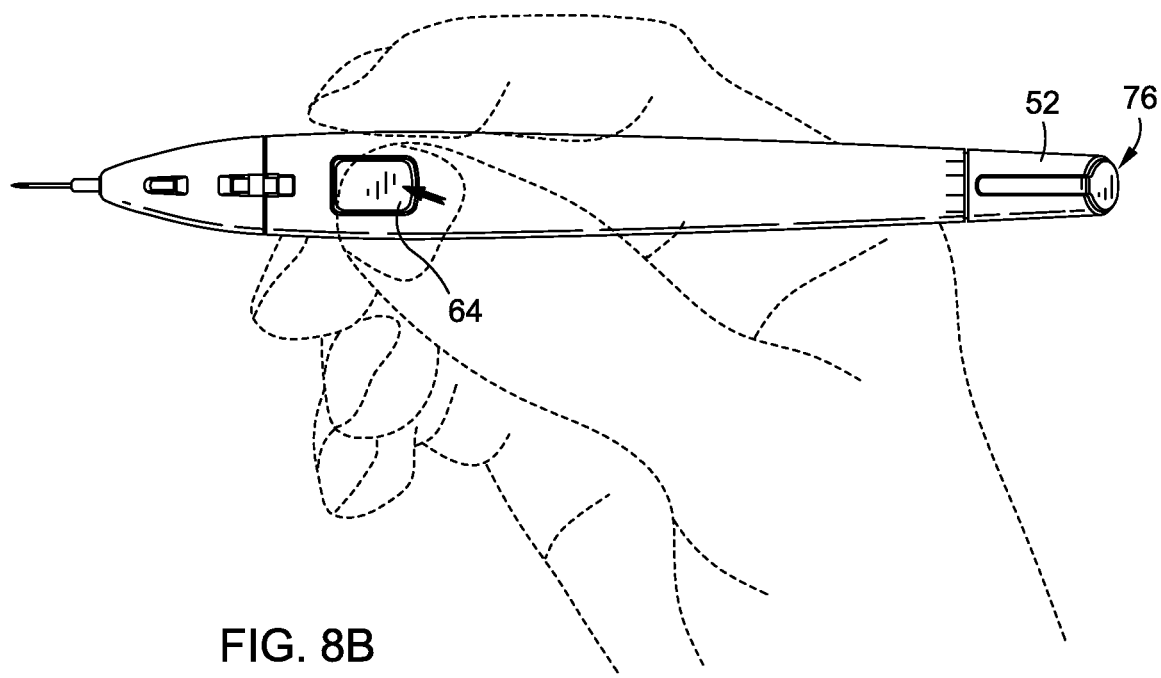
Figure 15B:
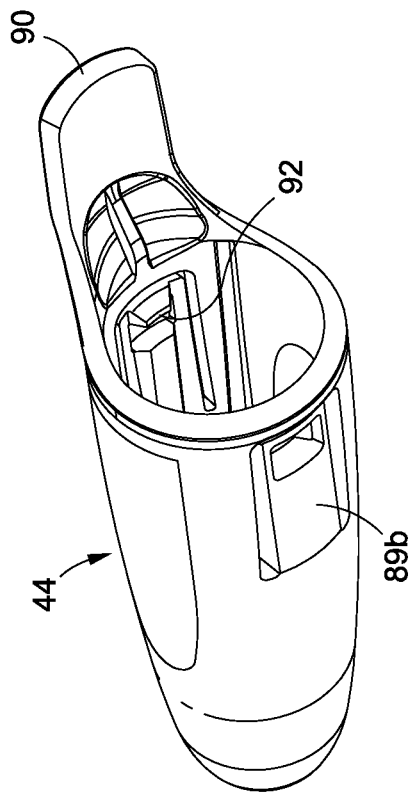
FIG. 15B shows a perspective view of the safety cap with the interior of the cap shown.
Figure 15A:
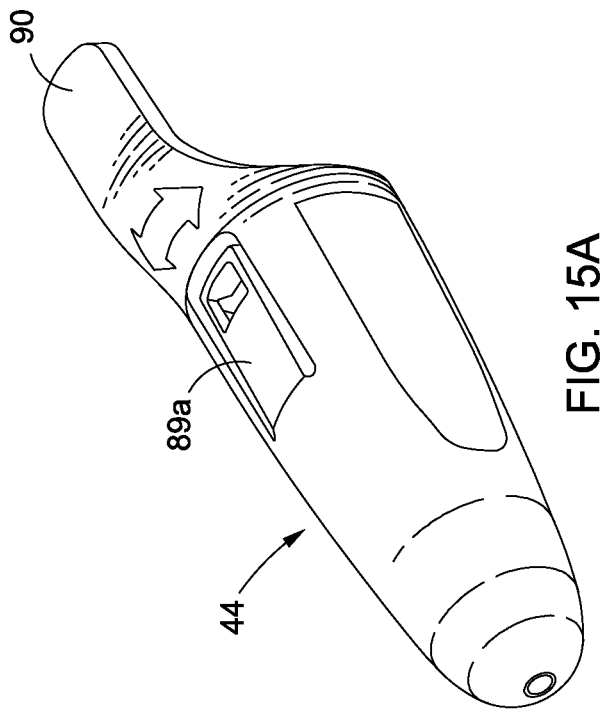
FIG. 15A shows a perspective view of the safety cap.
Figure 15D:
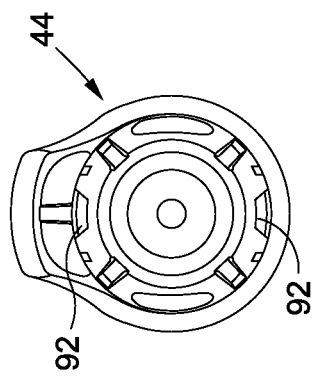
FIG. 15D shows an end view of the safety cap, showing the interior of the cap.
Figure 15C:
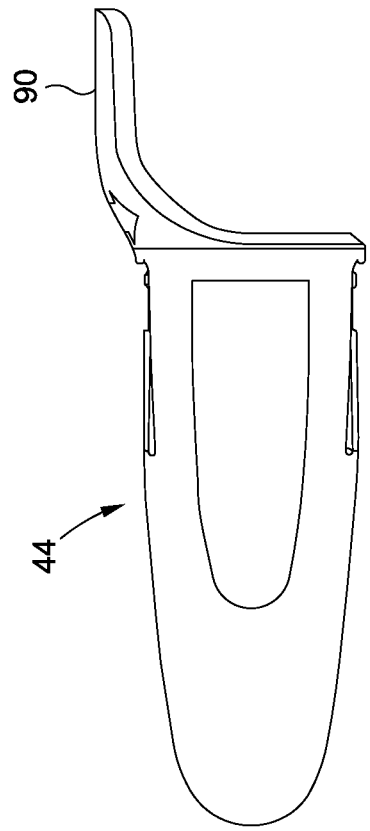
FIG. 15C shows a side view of the safety cap.

As shown in FIGS. 1A-5C, the presently described implant delivery apparatus 40, though tubular in shape, comprises two flat rubber-coated surfaces 70 on opposite sides of the exterior of cover bottom 48 to provide non-slip surfaces by which to firmly grip and hold the device. As shown in FIGS. 8A-8B, the flat rubberized surfaces 70 located on the housing (and specifically on cover bottom 48) facilitate alternative grips on the apparatus and permit the user to use either a thumb or a finger, as desired, to press ejector button 64. The provision of a rotatable needle 56 further facilitates alternative grips on the device since the user can orient the bevel of the needle toward or away from the surface of the eye by twisting needle-rotation knob 52, as shown in FIG. 4, irrespective of the user's grip on the device (FIGS. 8A-8B).

As can be understood from FIG. 4 and as shown in FIGS. 9A-9B, needle-rotation knob 52 at the proximal end of the housing is operably connected to needle 56 and can be used to rotate the needle in a clockwise or counter-clockwise direction (relative to the longitudinal axis of the housing), thereby allowing one to orient the bevel of needle 56, as desired, in relation to the surface of the eye. For example, the bevel can be oriented such that it faces away from the surface of the cornea as the needle is brought into contact with the eye and is inserted into the anterior chamber. Full 0° to 360° rotation of the needle bevel is possible as well as any incremental degree of rotation therebetween. Accordingly, needle bevel 57 may be oriented in any direction relative to the surface of the eye regardless of whether the apparatus is gripped with the left or right hand and regardless of whether the user is approaching the patient from the nasal, temporal, or superotemporal position, and irrespective of whether the user is activating the device with their index finger or thumb. Needle-rotation knob 52 may be snugly fitted against the housing to maintain the bevel in a given orientation once selected, and/or a frictional stop 72, in the form of a bendable or flexible tab that presses in on a portion of knob shaft 74 (which connects to the knob) inside the housing, is included in either the cover top 46 or cover bottom 48 or both to serve as resistance to the unintentional rotation of knob 52 (FIGS. 5A-5C and 10A-10C). Frictional stop 72 and its action on the knob shaft 74 are described in greater detail below.

As shown in the several views of the apparatus, including FIGS. 1A-6 and 9A-9B, needle-rotation knob 52 contains a shaded marking or coding element 76 on its surface to prominently indicate the orientation of the needle bevel. As shown in FIG. 6, coding element 76 is configured to snap onto the end of knob 52 and is a single piece including i) a slender rectangular, finger-like, projection 75 that extends lengthwise (and in a direction along the longitudinal axis of the housing) along the outer surface of knob 52, and ii) a slanted back surface 77 designed to represent the bevel of the needle 56, located at the opposite (distal) end of the apparatus. As noted above, projection 75 and slanted back surface 77 of coding element 76 can be shaded (e.g., in gray or black) so as to stand out from the base color of knob 52. As is apparent from FIGS. 9A-9B, the finger-like projection 75 may be elevated or raised above the surface of the needle-rotation knob.

In the fully assembled apparatus, finger-like projection 75 and slanted back surface 77 of coding element 76 are aligned with the bevel of the needle to provide the user with a clear visual indication of the orientation of needle bevel 57 relative to any reference point on the apparatus (see FIGS. 1A-1D, 3, 4, 5A-5C, and 9, for example). The user simply notes the location of the shaded marking 75 on the surface of the knob or the orientation of the slanted surface 77 at the end of knob 52. In this way, even with the extremely thin, high gauge needles for which the bevel may be difficult to see with the unaided eye, the user can quickly rotate the beveled portion of the needle to the degree desired and will immediately know, by looking at the coding element, in which direction the bevel is facing relative to the patient's eye. Needle-rotation knob 52 with coding element 76 is part of a needle rotation assembly 78, described in more detail below.

Overall the ability to freely orient the bevel of the needle relative to the surface of the eye, as shown in FIG. 4, can be a significant advantage. It is envisioned that the present device can be used in an outpatient setting wherein the patient is in the sitting or supine position in conjunction with a slit lamp or other illumination tool. As shown in FIGS. 8A-8B, the flat, rubber-coated surfaces 70 located on the exterior of housing 42, e.g., on cover bottom 48, facilitate alternative grips by the user. The physician can grip the device with the left or right hand in a manner that will allow the user to use either their thumb or index finger to press the ejector button 64. At the same time and without changing their grip, the user can use their other hand to independently orient the bevel away from or toward the eye, by rotating knob 52. Alternatively, the physician can, if necessary, first orient the needle bevel using the needle-rotation knob, and then grip the device in the preferred manner to inject the implant into the patient's eye. Orienting the bevel away from the surface of the eye may minimize trauma to the eye and promote the formation of a self-sealing wound, and may also permit the user to have a clear view of the implant as it exits and separates from the needle and enters the anterior chamber of the eye.

The intraocular implant delivery apparatus according to this disclosure can comprise, for example, a 22 gauge, 23 gauge, 24 gauge, 25 gauge, 26 gauge, 27 gauge, 28 gauge, 29 gauge, or 30 gauge needle. The needle can further be a thin-wall or ultra thin-wall needle. Finer, higher gauge needles, such as 28 gauge, 29 gauge, or 30 gauge needles, may be preferable for injections into the anterior chamber of the eye to create a small, self-sealing wound and to avoid fluid leakage from the eye. The distal end of the needle (i.e., the end that extends longitudinally from the distal end of the apparatus housing) is preferably beveled to create a sharp pointed tip that may easily penetrate the tissue of the eye. The intraocular implant delivered by the device should be receivable in and deliverable through the lumen of the needle. In one embodiment, the apparatus comprises a 28 gauge needle. In a more specific embodiment the apparatus comprises a 28 gauge needle with a wall that is 0.0015 inches to 0.0035 inches thick (i.e., about 0.038 mm-0.089 mm thick). In one embodiment the implant delivery apparatus comprises a 28 gauge needle with a wall that is 0.0015 inches to 0.00225 inches thick (i.e., about 0.038 mm-0.057 mm thick). In one embodiment the 28 gauge needle has a wall that is 0.0020 inches to 0.0030 inches thick (i.e., about 0.051 mm-0.076 mm thick). In one embodiment the 28 gauge needle has a wall that is 0.0020 inches to 0.00225 inches thick (i.e., about 0.051 mm-0.057 mm thick). In one embodiment the apparatus comprises a 28 gauge needle with a wall thickness of about 0.0020 inches. In other embodiments, the apparatus comprises a 27 gauge needle with a wall that is 0.0015 inches to 0.0040 inches thick (i.e., about 0.038 mm-0.102 mm thick), or more specifically, that is about 0.0025 inches thick. Another embodiment provides for an apparatus according to this disclosure comprising a 29 gauge needle, wherein the needle wall is 0.0015 inches to 0.0030 inches thick (i.e., about 0.038 mm-0.076 mm thick), or more specifically, about 0.0020 inches to about 0.0025 inches thick. A 30 gauge needle may have a wall that is 0.0020 inches to 0.0025 inches thick.

In other embodiments, the apparatus comprises a 22 gauge, 23 gauge, 24 gauge, or 25 gauge needle. As may be appreciated by one of skill in the art, the diameter of the implant may be increased or decreased (e.g. during production) in correspondence with the inner diameter of the needle that is present on the implant delivery device to produce an implant that can be received in and slidably translated through the lumen of the needle.

One example of an intraocular implant suitable to be received in and delivered by the present apparatus is a rod-shaped, biodegradable, drug-containing implant formed by an extrusion process having a diameter and a length that is suitable for delivery through the needle and suitable for placement in the anterior chamber of the eye. Such implants may be referred to as intracameral implants. According to some embodiments, the rod-shaped intracameral implant contained by the apparatus is 0.5 mm to 3 mm in length and 0.05 mm to 0.3 mm in diameter (or maximum width in the case of non-cylindrical rods). In one embodiment, the intracameral implant is 0.5 mm to 2 mm in length and 0.05 mm to 0.25 mm in diameter. For example, the intracameral implant can be 100 µm to 200 µm (±10 µm) in diameter.

As shown in FIGS. 12A-12E, 13 as well as other figures such as FIGS. 1A-1D, 2, 3, 6, and 7A-7B, needle 56 is attached to and extends from needle hub 58, which is receivable in nose cone 50. In one embodiment, needle 56 is overmolded with or bonded to needle hub 58. As shown in FIGS. 12A-12E, needle hub 58 comprises a blunt ended nose 80 through which needle 56 extends. As can be seen in FIGS. 1A-3, needle hub nose 80 extends through opening 60 in nose cone 50. The length of exposed needle extending from needle hub nose 80 is fixed and governs the maximum distance the needle may be advanced into an eye. In the current device, this length, from the distal end of nose 80 to needle tip 82 (FIGS. 9A-9B and 12A-12E), is set to a length optimal for delivery of an implant into the anterior chamber of the eye (e.g., the human eye). In addition, the outer surface of the needle may optionally contain one or more marks as guides to the practitioner by which to know the length of the needle advanced into the eye prior to activation of the device; however, needle hub nose 80 acts as an additional "safety stop" and thereby an additional safety feature, preventing further advancement into the eye, helping prevent injuries that might otherwise occur if the needle were inadvertently advanced too far into the anterior chamber.

According to one embodiment, the length of the needle, from the distal end of needle hub nose 80 to needle tip 82, is 4 mm to 8 mm. According to another embodiment, the length of exposed needle from hub nose 80 to needle tip 82 is 4 mm to 6 mm. The needle can be fixed to the needle hub in a manner to provide for devices with various needle lengths, as desired. For example, the needle length from needle hub nose 82 to needle tip 82 can be from 4 mm to 6 mm or from 4 mm to 5 mm. In some embodiments, the length of the needle is 5 mm or 7.5 mm. As shown in FIG. 13, needle hub 58 is configured to receive and engage with an implant holder 84, further described below. Thus, implant holder 84 is received within needle hub 58.

An implant delivery feedback window 86, can be located on bottom cover 48, as shown in FIGS. 1A-6 and 10A-10C. In general, two delivery feedback windows 86 are provided, each being located on opposing sides of bottom cover 48 so that a window 86 be viewed by the user regardless of whether the apparatus is held by the left or right hand and regardless of which side of the apparatus is facing the user. The delivery feedback window 86 lets the user know that the implant delivery apparatus has been activated (i.e., that the spring has been released and the release lever, and therefore the push rod, has been driven forward along the longitudinal axis of the housing toward the distal end of the apparatus. This provides the user with evidence not only with regard to the readiness of the device prior to insertion into an eye, but also with regard to the successful activation of the spring-driven mechanism of the device during use in a patient's eye.

Activation of the device is indicated by a color or pattern change or by a texted or graphic signal or any combination thereof that can be observed by the user through the delivery feedback window 86. For example, the color shown in the window may change from red to green, or green to red, and, to aid those with difficulty in distinguishing colors, the pattern shown in the window may change from a first pattern to second pattern distinct from the first, or, in addition to or instead of a color change, the user may receive texted confirmation of implant ejection by observing a change from one symbol such as "Ø" to another symbol such as "OK", or vice versa, after ejector button 64 has been pressed, i.e., after activation of the device. These color, pattern, graphic, and texted changes can be communicated to the user by imprinting one or more colors or adding one or more labels onto the side(s) of the release lever 136 (described in greater detail below), as shown in FIGS. 6 and 14A-14B. See also FIGS. 26A-26C. For example, a region at the proximal end of the release lever can be colored red or any other distinguishable color (e.g., black, blue, purple, orange, and the like), as depicted in FIGS. 6 and 14A-14B, and other accompanying figures (see section of release lever 136 labeled "Red"). Because the release lever 136 must slidably translate forward, along the longitudinal axis of the housing, toward the distal end of the apparatus under the action of the spring when the ejector button is depressed, the forward movement of the release lever indicates activation of the device. Thus, activation of the apparatus can be clearly communicated to the user by providing a window into the housing (a delivery feedback window) to view the change in location of the release lever from a first position to a second position. For this purpose, two discrete sections along the lateral edge of release lever 136 can be labeled with two different colors, patterns, and/or text symbols. A first color, pattern, or text symbol will show in and be visible through the delivery feedback window prior to activation, but will slide out of view as a second different color, pattern, or text symbol slides into view as the release lever is forced forward along the longitudinal axis of the housing toward the distal end of the apparatus by the spring following activation of the device. In one embodiment, the release lever as a whole is green (e.g., the release lever may be cast of a green-colored plastic) and a single region at the proximal end of the release lever is painted or differently colored (e.g., red) (See FIGS. 6 and 14A-14B) and may, optionally, be further labeled with text to clearly indicate when this region of the release lever slides into view of the delivery feedback window following activation of the apparatus.

As previously stated and as shown in FIGS. 1A-1D, 5A-5C, 6, and 13 the intracameral implant delivery apparatus 40 can further comprise a safety cap 44. As shown in FIGS. 1A-1D, safety cap 44 is designed to both guard the needle and to prevent premature or unintentional activation of the device during shipping and handling. Safety cap 44 snaps and/or twists onto the distal end of the housing 42. Specifically, safety cap 44 includes flexible or bendable tabs 89a and 89b located on opposing, upper and lower sides of cap 44 (FIGS. 1A-1D, 5A-5C, and 13). Each tab 89a and 89b comprises bosses (or projections) 92 that are configured to snap-fit into recesses 88a-d, respectively, present on the upper and lower surfaces of nose cone 50 and on cover bottom 46 and cover bottom 48 (FIGS. 1A-3 and 5A-5C). As can be seen in FIGS. 1A-1D, 6, and 13, safety cap 44 is designed to receive nose cone 50 and, is of sufficient length and volume to guard and prevent damage to needle 56 extending out through the opening in the nose cone 50. The safety cap further guards the user against injury by the needle during handling.

As seen in FIGS. 1A-1D and 15A-15D, safety cap 44 comprises a finger 90 that projects over ejector button 64 when the cap is snapped into position on nose cone 50. In this manner, finger 90 guards ejector button 64, preventing unintentional depression of button 64 and activation of the device. Additionally, as shown in FIGS. 13 and 15A-15D, boss-like projections 92 are present on each flexible tab 89. These are specifically located at the far bendable end of each tab. Bosses 92 are received into recesses 88a-d on the housing. On the bottom of the housing, these projections 92 click into recesses 88c and d present on nose cone 50 and cover bottom 48, respectively. See also FIGS. 16A-16E. On the top of the housing, projections 92 of the upper tab 89a click into recesses 88a and 88b present on nose cone 50 and cover top 46, respectively. When clicked into recesses 88a and 88b, one projection 92 comes to rest against a boss section 94 present on ejector button 64. See FIGS. 18A-18E. As may be understood by reference to FIGS. 2, 5A-5C, 11A-11C and 17A-17C, boss section 94 of ejector button 64 extends up through an opening 96 in cover top 46. Activation of the device requires that ejector button 64 be pressed down in a direction perpendicular (i.e., normal) to the longitudinal axis of the housing, which in turn requires that the front section of the button 64, containing the boss 94, move an upward direction away from the device. See FIGS. 18A-18E, showing enlarged views of button 64, boss 94, and the cylindrical posts 95 about which the button 64 pivots when present in the assembled apparatus. As may be appreciated by reference to FIGS. 19A-19D, 20A-20B, and 21A-21B, ejector button 64 pivots about cylindrical posts 95, projecting laterally from each side of button 64, in a see-saw fashion so that, as one end of the button is pressed down, the other end (containing boss 94) goes up. Cylindrical posts 95 clip into U-shaped jaws 47 present on the underside of cover top 46, as shown in FIGS. 11B and C. The jaws secure the button 64 to the cover top but permit rotational movement of the posts 95 within the jaws. Thus, button 64 is able to move in see-saw fashion when clipped into the jaws 47. Projection 92 on the inner surface of flexible tab 89a of safety cap 44 blocks the upward movement of boss 94 present on the front section of ejector button 64, which together with finger 90, which projects out over the button, prevents the unintentional depression of the ejector button 64 and inadvertent activation of the intraocular implant delivery device 40 during manufacture, packaging, shipping, and routine handling.

Safety cap 44 can be designed in a manner so that it is removed from the apparatus by either pulling it off the apparatus in one motion or in a manner that requires it first be twisted clockwise or counterclockwise (see wide arrow on cap in FIGS. 1A-1D) before it can be pulled off the apparatus.

Turning now to needle hub 58, it can be seen from the several views of the apparatus accompanying this description, including FIGS. 2, 3, 6, 7A-7B, 12A-12E, and 13 that beveled needle 56 extends from the distal end of needle hub 58. The needle hub has an interior configured with i) a membrane-opening nipple 62 and ii) a plurality of ribs 100 or other elements configured for catching, grabbing, or engaging recesses or indentations 102 in the proximal end of implant holder 84, such that rotation of implant holder 84 in a clockwise or counterclockwise direction causes rotation of needle hub 58 and needle 56, fixed to needle hub 58, in the same clockwise or counterclockwise direction to the same degree (FIGS. 12A-12E, 13, 19A-19D). The externally located knob 52 at the proximal end of the housing (see FIGS. 1A-5C) allows the user to rotate implant holder 84 and thereby needle 56 prior to delivery of the implant, as described in more detail below. Needle hub 58 is receivable within the interior of nose cone 50 such that the needle extending from the distal end of the needle hub (and specifically from the needle hub nose 80) will thereby extend through opening 60 in nose cone 50.

Prior to ejection from the apparatus, the drug-containing intracameral implant is held within the apparatus in implant holder 84, as depicted in FIGS. 7A-7B and 20A-20B. Enlarged views of implant holder 84 are shown in FIGS. 19A-19D. As may be understood from the description above and the attached figures, implant holder 84 is receivable in needle hub 58 and is further configured for snap-fit attachment to push rod guide 118. More specifically, the proximal end of implant holder 84 fixedly attaches to the distal end of push rod guide 118.

Figure 19D:
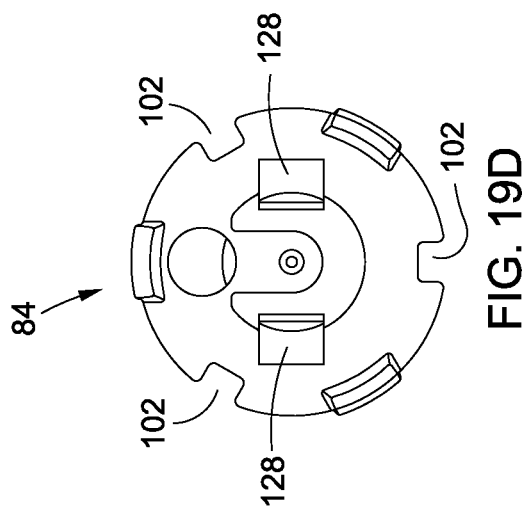
FIG. 19D shows a back (proximal) end view of the implant holder.
Figure 19B:
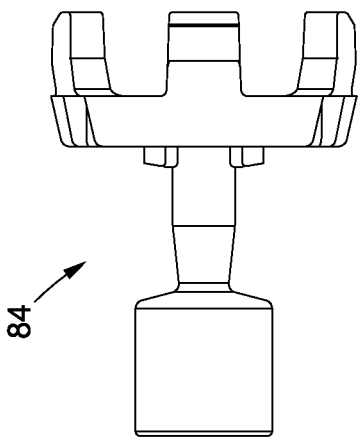
FIGS. 19B and C show side views of the implant holder with membrane 106.
Figure 19C:
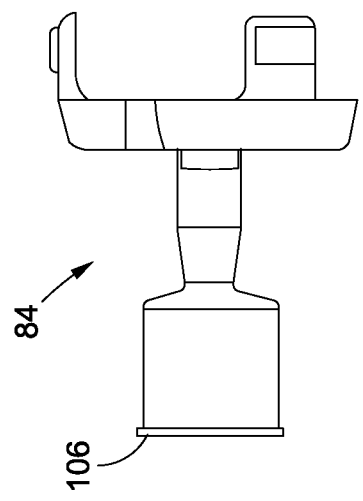
FIG. 19A shows a perspective view of the implant holder with membrane 106.
Figure 19A:
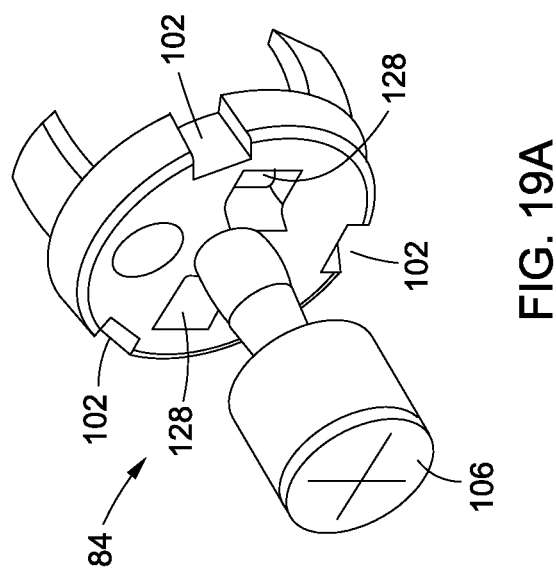

As shown in FIG. 7A, prior to activation of the apparatus, the intraocular implant 68 is secured in the implant holder by means of a membrane 106 at one end (the distal end of the implant holder) and a push rod 108 at the other end (the proximal end of the implant holder). The implant holder contains a bore or lumen. The implant is loaded and held within the lumen of the implant holder. The push rod 108 is generally cylindrical and can be made of a metal or metal alloy. The diameter of the push rod should be such that the push rod is freely receivable within the lumen of the implant holder and within the lumen of the needle used with the apparatus. In one aspect, and as can be seen in FIG. 19A, the membrane 106 is cross-slit to allow for transfer of the implant 68 from the implant holder 84 to the needle 56 upon activation of the device. According to some embodiments, other slits in addition to the cross-slit may be included in the membrane. Membrane 106 may be made of a metal-based foil such as an aluminum foil or other suitable material that provides a suitable barrier to the implant during storage of the device but that can be slit, partially slit, or perforated or folded back when forced against nipple 62 inside the needle hub 58 upon activation, as schematically depicted in FIGS. 7A and 7B. According to some embodiments, membrane 106 is an aluminum foil membrane that is 10 µm to 60 µm thick. As previously discussed, the inclusion of slits or cross-slits or both can facilitate the separation of sections of the membrane and promote clearance of the membrane away from the distal end of the implant holder to allow for translation of the implant from the holder to the lumen of the needle during activation of the device. As shown in FIGS. 7A-7B, nipple 62 inside needle hub 58 has a cone-shaped passageway 59 that leads into the lumen of needle 56 and, which, because of its cone shape, helps guide the implant into the lumen of the needle 56 when the implant is driven forward by push rod 108.

The implant holder 84 is made of a transparent material, such as a clear plastic (e.g., a polycarbonate), such that the implant 68 can be seen within the holder. According to one embodiment, the implant holder is designed for use with cylindrical or non-cylindrical rod-shaped implants that have a diameter and are cut to a length suitable for placement in the anterior chamber of an eye. As shown in FIGS. 1A-5C, 9A-9B, 12A-12E, and 13, implant inspection windows 112 and 112' (112 prime), are incorporated into nose cone 50 and needle hub 58, respectively. As may be appreciated from FIGS. 12A-12E and 16A-16E, two inspection windows 112 and two inspection windows 112' are present on the nose cone and needle hub, respectively. The two windows on the nose cone (and implant holder) are separated from one another by about 180°, being located on opposing sides of the nose cone (and implant holder). In the fully assembled apparatus, the windows 112 on the nose cone can be aligned with windows 112' on the implant holder by twisting needle-rotation knob 52, such that in the fully assembled apparatus the two windows 112 can be aligned immediately above and below windows 112' on the implant holder (located inside the device) so that a beam of light can pass through all four windows and the presence of an implant in the apparatus (and implant holder 84) can be visually confirmed by looking through either of the inspection windows 112 in nose cone 50 (FIGS. 16A-16E), as depicted in FIGS. 17B and C. For example, an implant inspection window 112 is located on the top and bottom surfaces of nose cone 50, which is connected to (and snaps onto) both the cover top 46 and cover bottom 48. Needle hub 58 located inside nose cone 50 contains matching windows 112' aligned with windows 112 in nose cone 50 so that one may visualize the intracameral implant 68 in the implant holder within the needle hub. The implant inspection windows provide a useful quality control feature, enabling one to confirm the presence of the implant in the device prior to packaging, prior to sterilizing, and prior to actual use in any eye. To further facilitate visual inspection and verification of the implant in the assembled apparatus, one embodiment provides for implant inspection windows 112 in the nose cone that comprise or that are in the form of a magnifying element, lens, or other optical element that enlarges or magnifies the view of the implant inside the implant holder. An optical element may also be included in the safety cap to magnify the implant image and the safety cap may be made of clear plastic material that permits one to easily see the intraocular implant inside the housing of the assembled apparatus.

Membrane 106 can be affixed, glued, welded (sealed onto the holder by heat), or bonded to the distal end of implant holder 84. The membrane 106 affixed to the distal end of the implant holder 84 is preferably a thin pliable material that can bend, fold back, or otherwise open when forced against the membrane-opening nipple 62 inside needle hub 58. In some embodiments, the membrane is a thin metal or metal- or metal-alloy based foil. In one embodiment the membrane is made of an aluminum foil and is cross-slit (e.g., in the shape of an "X") so that it may fold back when it is forced against the nipple 62 inside needle hub 58 (FIGS. 7A-7B, 20A-20B, and 21A-21B). In addition to the first cross-slit, second slits may be added to the membrane, such as at the periphery of the cross-slit, to further promote clearance of the membrane material upon contact with the nipple 62.

Implant holder 84 is moveable in a direction along the axis of the housing from a first position to a second position against nipple 62 inside needle hub 58. Movement of the implant holder from a first position to a second position against nipple 62 inside the needle hub occurs upon depression of ejector button 64. When membrane 106 at the distal end of the implant holder is forced forward against nipple 62, nipple 62 forces membrane 106 open, by, for example, causing cross-slit sections of the metal-foil membrane to fold back, allowing for unrestricted passage of the implant 68 from the lumen of implant holder 84 into the lumen of needle 56 (compare FIGS. 20A-20B and 21A-21B and see FIGS. 7A-7B). Passage of the implant from the implant holder 84 to the needle is driven by push rod 108, as described below.

According to one embodiment, the implant holder is loaded with a single, rod-shaped, intraocular implant. However, other embodiments provide for a method of introducing two or more solid, rod-shaped implants into an ocular region of the eye (e.g., the anterior chamber or vitreous), using the present apparatus. Delivery of two small implants, instead of one large implant, may be one means for delivering a larger dose of active agent into the eye. Thus, in some embodiments the implant holder is loaded with two or more rod-shaped, drug-containing, intraocular implants.

Figure 22:
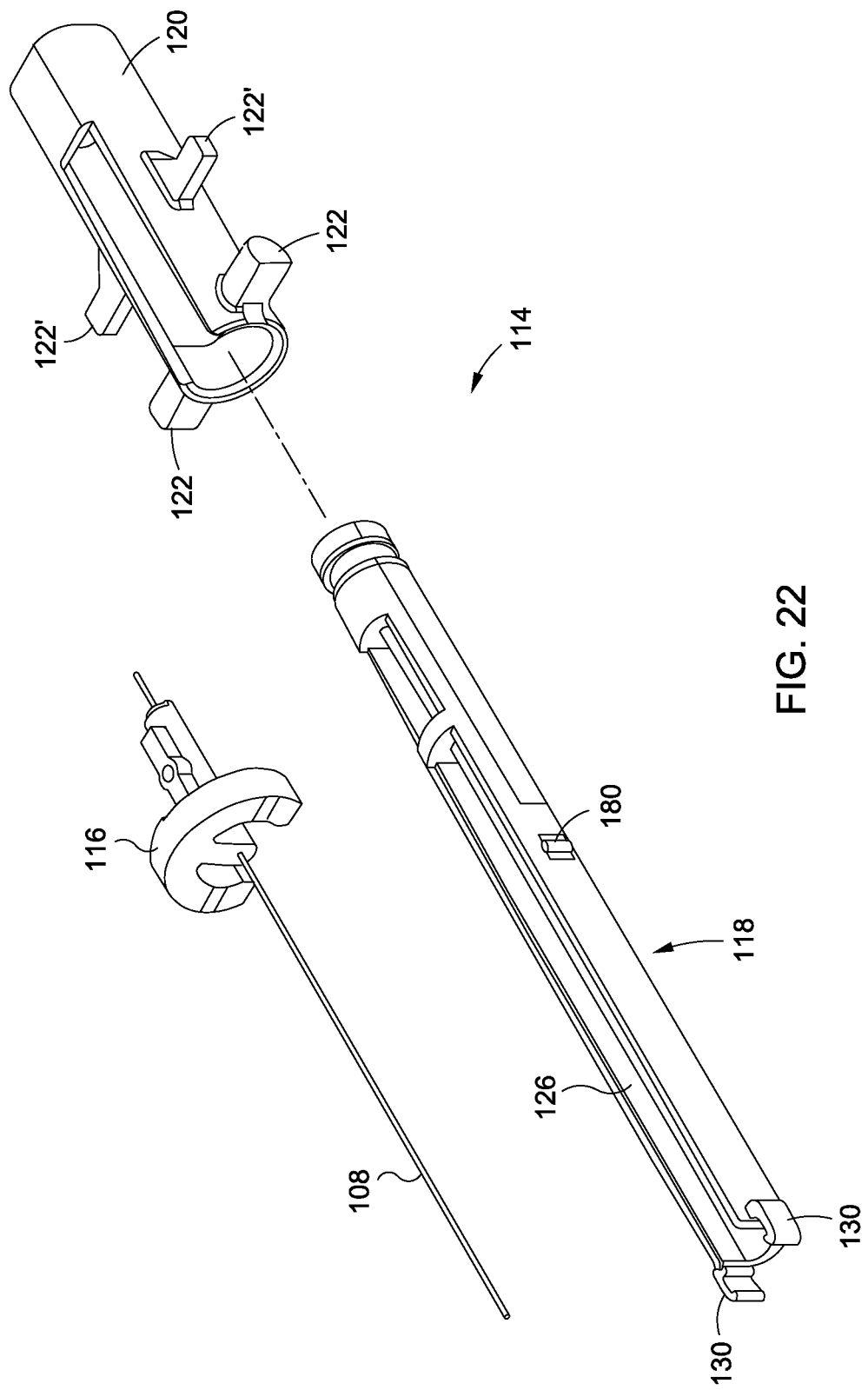
FIG. 22 shows an enlarged perspective view of the push rod conveyor 116, the push rod 108, the push rod guide 118, and the push rod assembly sleeve 120, which together form the push rod assembly. As shown in the figure, the push rod conveyor is overmolded with or fixed to the proximal end of the push rod and is configured for receipt in channel 126 in the push rod guide 118.
Figure 23:
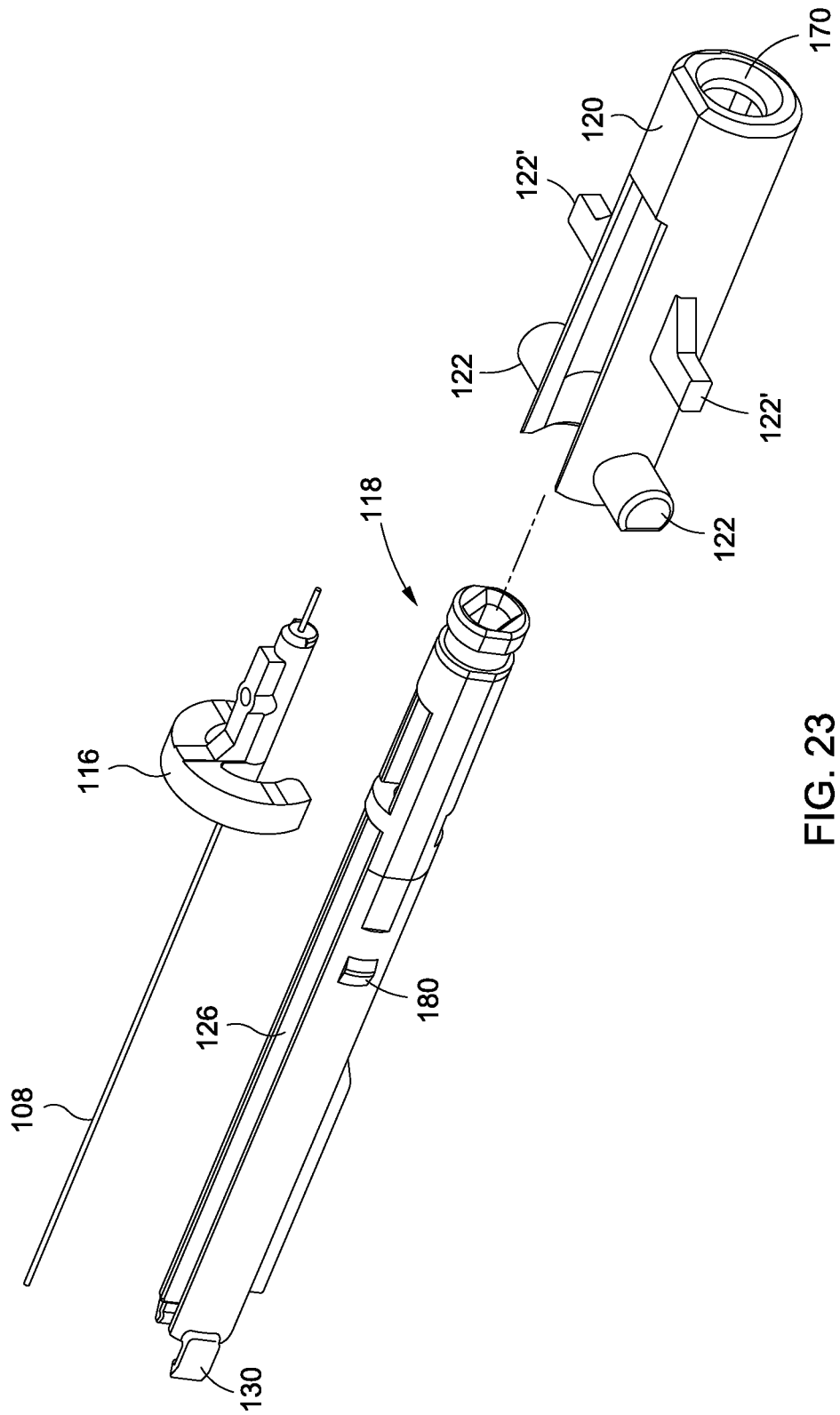
FIG. 23 shows an additional perspective view of the push rod assembly components (see brief description of FIG. 22). This view shows the proximal end of the push rod guide, having a square or rectangular-shaped opening which can receive the distal end of the metal connecting rod such that when the metal connecting rod is connected to the push rod guide and is rotated clockwise or counterclockwise it will, in turn, rotate the push rod guide in identical fashion. The narrowed or restricted opening 170 at the proximal end of the push rod assembly sleeve 120 can also be seen in this perspective view.
Figure 24:
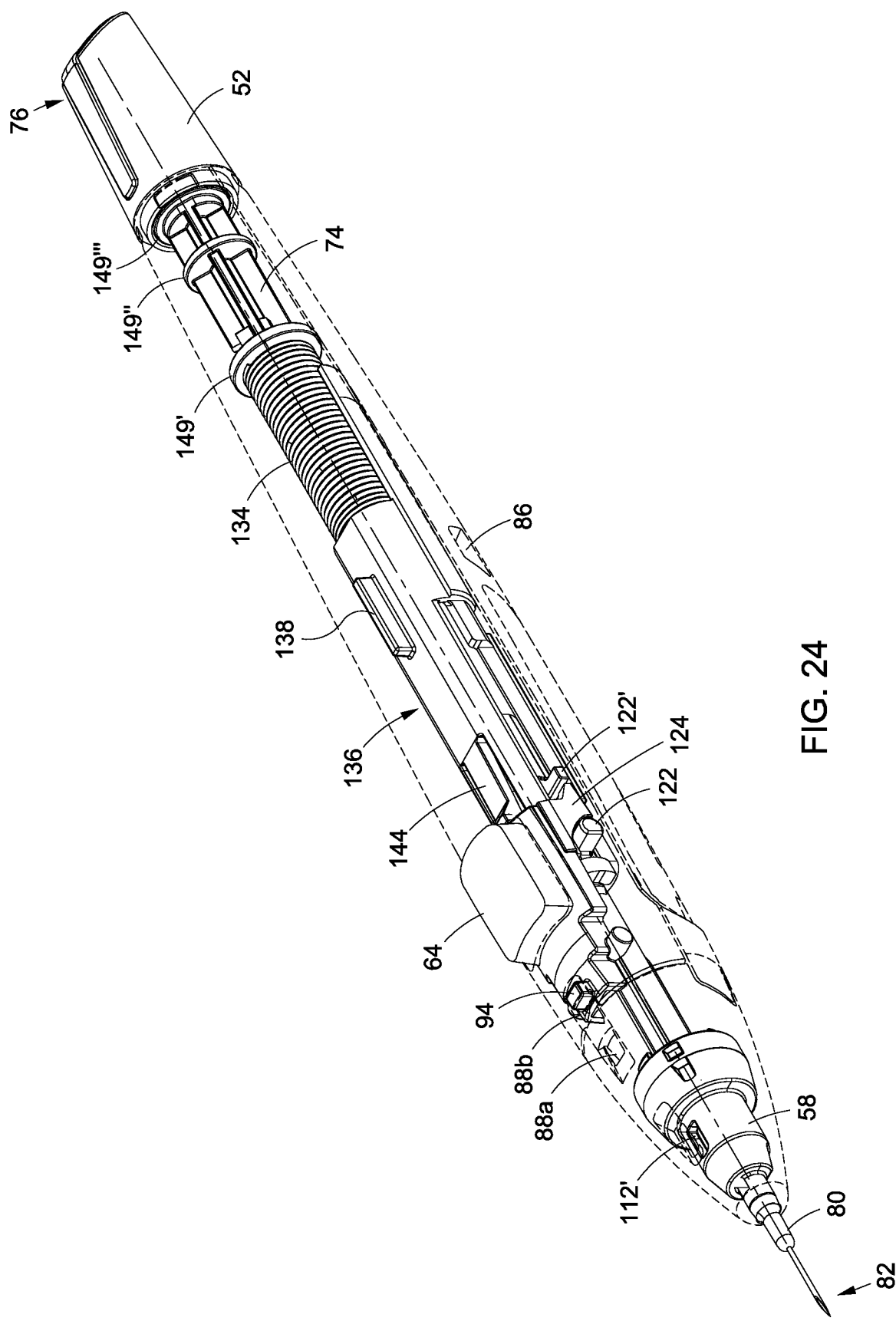
FIG. 24 shows a perspective view of the internal assembly of the apparatus prior to activation. The housing is shown in dotted outline. The various components of the apparatus are shown in perspective in relation to one another in the fully assembled apparatus. Prior to activation, the spring is compressed between the proximal end of the release lever and the distal end of the knob shaft, as shown.

Accordingly, the intracameral implant delivery device can further include a push rod assembly 114 (shown in FIGS. 22 and 23) including i) a push rod 108, ii) a push rod conveyor 116, iii) a push rod guide 118, and iv) a sleeve 120, wherein sleeve 120 is engaged with ejector button 64 such that downward movement (e.g., depression) of ejector button 64 causes (i.e., is translated into) forward movement of sleeve 120 and, thereby, forward movement of push rod assembly 114 along the longitudinal axis of the housing toward (i.e., in the direction of) the distal end of the device, as shown schematically in FIGS. 20A-20B and 21A-21B. Push rod 108 and push rod guide 118 each have proximal and distal ends. As can be seen in FIG. 22, sleeve 120 is configured as a hollow cylinder with an inner diameter sufficient to slide over and receive the proximal end of push rod guide 118. As shown in FIG. 23, sleeve 120 has a restrictor 170 at one end (i.e., the opening at one end of the sleeve (the proximal end) is narrower than the other end) to prevent the sleeve from sliding over the entire length of push rod guide 118. As shown in FIGS. 22 and 23, the sleeve 120 further comprises forward and rearward guide posts 122 and 122 (122 prime), respectively, on opposing sides (two posts on each side) of its exterior for engaging with wings 124 that are present on each side of ejector button 64. The forward posts 122 correspond to those at the distal end of the sleeve. As shown in the several views of the apparatus, including FIGS. 2, 17A, 20A-20B, 21A-21B, and 24, the wings of the ejector button fit between the forward and rearward guide posts. Wings 124 of ejector button 64 curve forward such that depression of the button causes the wings 124 to sweep sleeve 120 forward toward the distal end of the apparatus. This occurs because, as button 64 is depressed, it pivots about the cylindrical posts 95 that are clipped into cover top 46. At the same time, as button 64 pivots about posts 95, the curvature of the wings 124 maintains a constant frictional force against the forward posts 122 on the sleeve 120. Thus, because the opening in sleeve 120 is sufficiently narrow at its proximal end such that the sleeve cannot slide over the proximal end of push rod guide 118, sleeve 120 converts downward force on ejector button 64 (i.e., the force applied to depress button 64) into forward longitudinal movement of push rod guide 118 toward the distal end of the apparatus. Because implant holder 84 is fixedly secured to the distal end of push rod guide 118 (as may be apparent from FIGS. 6, 20A-20B, 21A-21B, and 25A-25B, and as discussed below), longitudinal movement of push rod guide 118 toward the distal sharp end of the apparatus results in longitudinal movement of the implant holder 84 toward nipple 62 within needle hub 58, ultimately causing implant holder membrane 106 to be forced against nipple 62 inside needle hub 58 (see FIGS. 7A-7B, 20A-20B, and 21A-21B, for example). Nipple 62 thereby forces open membrane 106, by, for example, forcing the cross-slit sections of membrane 106 to fold back. Communication between the lumen of the implant holder and the lumen of needle 56 is thereby established such that the implant can slidably translate from the lumen of the implant holder into the lumen of the needle upon movement of the push rod 108. As can also be understood from the several views of the apparatus in the attached figures, because the wings 124 of ejector button 64 are disposed between forward and rearward guide posts, designated as 122 and 122' (122 prime), respectively, on either side of ejector button 64, these posts further serve to prevent the sleeve from inadvertently falling out of position during assembly of the apparatus.

As shown in FIGS. 7A and 20A-20B, in the pre-activation state of the device 40, a portion of the distal end of push rod 108 resides in implant holder 84 and is in contact with, is adjacent to, or abuts the intraocular or intracameral implant 68, thereby preventing backward movement of and inadvertent, unintentional loss of the implant from the implant holder during assembly and prior to activation of the apparatus. Thus, prior to activation of the apparatus and prior to deployment of the implant in the eye, the intraocular implant 68 is secured within implant holder 84 by membrane 106 at one end (the distal end) of the implant holder 84 and push rod 108 at the other end (proximal end) of the implant holder 84. As discussed above, the intraocular implant can be an intracameral implant.

As shown in FIGS. 9A-9B, 22 and 23, push rod conveyor 116 is configured to be received within a groove or channel 126 present in push rod guide 118. The push rod 108 is overmolded with or bonded to the push rod conveyor 116, which as shown in FIGS. 22 and 23, is a semi-circular, "U" shaped element having a tongue that fits into the groove 126 in the push rod guide 118 and having flanking members that curve around the outside of push rod guide 118. With its U-shaped structure, push rod conveyor 116, and therefore the push rod 108 to which it is bonded or fixed, can slide forward along the longitudinal axis of the housing within the channel 126 present in push rod guide 118, toward the distal end of the device, from a first position to a second position along the longitudinal axis of the housing. As shown in FIGS. 22, 23, and 27A-27E side bumps 180 are provided on each side of push rod guide 188 to keep the push rod conveyor and associated push rod from prematurely sliding through channel 126 prior to activation of the spring. The stroke length of channel 126 (the distance conveyor 116 can travel in channel 126) in push rod guide 118 can vary, but may be from 10 mm to 50 mm, for example.

As discussed above, push rod 108 is configured for slidable receipt within the lumen of implant holder 84 and the lumen of the needle 56 extending from the needle hub 58. Push rod 108 is of sufficient length to displace an implant loaded in the implant holder from the holder into the needle lumen and through the length of the needle to thereby eject the implant from the distal end of the needle (or needle tip). The push rod can be a metal or metal alloy cylindrical rod 10 mm to 50 mm long, although the length of the push rod can be varied. The diameter of the push rod can vary, but should be sized so that the push rod is slidably receivable within the lumen of the implant holder and the lumen of the needle attached to the needle hub.

Implant holder 84 locks or snaps onto or is fixedly secured to the distal end of push rod guide 118. In one form of the device, the implant holder has two or holes 128 that can receive and cling to two or more prongs or snap hooks 130 present on the distal end of the push rod guide 118 (FIGS. 19A-19D, 22, 23, 25A-25B, and 27A-27E). Enlarged views of push rod guide 118 are shown in FIGS. 27A-27E. In this manner, the push rod guide and implant holder are interlocked and can be rotated in unison as a single assembly.

As may be understood from the several figures (e.g., FIGS. 2, 9A, and 24) and preceding disclosure, the intracameral implant delivery apparatus can further comprise a spring-driven assembly for ejection of the intracameral drug-containing implant from the device and a needle rotation assembly 78 for rotating the beveled needle 56 attached to needle hub 58 and extending from the distal end of the apparatus. The spring-driven assembly is engageable with the push rod (and specifically with the push rod conveyor) and forces the push rod through the lumen of the implant holder and the lumen of the needle following activation of the apparatus.

The spring-driven assembly comprises or consists of i) a spring 134, and ii) a release lever 136 for ejection of the implant from the device (see, for example, FIGS. 24, 25A-25B, and 26A-26C). In the present apparatus, the distance the implant 68 is driven away from the tip of the device by the spring-driven assembly depends, in part, on the spring used in the device (e.g., the spring constant and the potential energy stored in the spring in its compressed state) and is independent of and not proportional to the force applied to the button by the user. According to one embodiment, the present apparatus comprises a helical or coiled spring. The helical spring may be characterized according to the formula $F=kx$, where F is the force needed to extend or compress the spring by some distance x, and where k is a constant factor characteristic of the spring. For example, k may be considered to be a measure of the "stiffness" of the spring. Accordingly, the force F with which an implant is ejected from the current apparatus (expressed in Newtons, for example) is proportional to the spring constant k and the displacement x of the free end of the spring relative to its position in the relaxed state. In one embodiment, the apparatus contains a helical spring, as seen in FIG. 25A. In a more specific embodiment the helical spring is a progressive helical spring as shown in FIG. 25B.

According to one method for using the present apparatus to deliver an implant into the anterior chamber of any eye, the needle is inserted into the anterior chamber of an eye to a depth of about 5 mm, as measured from the tip 82 of the needle inside the eye to the surface of the cornea where the needle first penetrates the eye, and the implant is ejected a distance of at least 2 mm to 4 mm, but not more than 5 mm or 6 mm, away from the tip 82 of the needle 56, as measured from the back end of the implant to the tip of the needle, following activation of the apparatus. Preferably, the implant delivery apparatus ejects the intracameral implant into the anterior chamber of the eye with a force that is sufficient to drive the implant away from the tip of the needle so that it does not adhere to the needle as the needle is withdrawn from the eye, but insufficient to cause the implant to strike or ricochet off the iris or tissues on the other side of the anterior chamber. An implant that adheres to the needle tip as the needle is withdrawn from the eye may become lodged in the cornea as the needle is withdrawn, possibly leading to undesirable effects such as corneal edema and inflammation. On the other hand, implants that are ejected too forcefully may strike the iris or side of the anterior chamber, which may cause hemorrhages. Ejection distances can be experimentally measured in vitro by ejection into, for example, a balanced salt solution (BSS) at 25° C. to 37° C. In some embodiments the apparatus ejects the intraocular implant a distance of 2 mm to 4 mm away from the tip of the needle in a liquid medium, such as BSS at a temperature of 25° C. to 37° C. The measurement may be taken, for example, from the back end of the implant to the tip of the needle.

Release lever 136 is positioned in the apparatus for slidable movement along the longitudinal axis of the housing axis and toward the distal, needle-tipped end of the device. As shown in FIGS. 6, 10A-10C, 14A-14B, 25A-25B, and 26A-26C, release lever 136 is a hollow cylindrically shaped member having proximal and distal ends and capable of receiving and sliding over push rod assembly sleeve 120. On opposing sides of its exterior, the release lever contains rails 138 (or raised contoured surfaces) extending along the longitudinal length of the release lever. Rails 138 are configured for receipt in and are slidable within tracks 140 located inside the housing on the underside of cover top 46 and interior surface of cover bottom 48. Tracks 140 are aligned with the longitudinal axis of the housing and extend along the length of cover top 46 and cover bottom 48. Consequently, due to receipt of rails 138 in tracks 140, the release lever is not rotatable within the housing but is slidable within the housing along tracks 140 in a forward direction toward the distal end of the device. As shown in FIGS. 6, 14A-14B, 25A, and 26B, and as may be understood from FIGS. 2, 17A-17C, and 24A-24B, the release lever 136 is also configured with slots 142 through which guide posts 122 and 122' on push rod assembly sleeve 120 can be received and slidably translate. The diameter of the distal end of the release lever, however, is too small to receive and therefore cannot slide over push rod conveyor 116. In the pre-activation state of the apparatus, push rod conveyor 116 is positioned against the distal end of release lever 136 and conveyor 116 is sufficiently large (e.g., has a sufficient diameter or width) such that it cannot be received within release lever 136. Accordingly, forward translation of release lever 136 along the longitudinal axis of the housing (toward the distal end of the device) results in forward longitudinal movement of push rod conveyor 116 and, consequently, forward movement of push rod 108. Since the distal end of release lever 136 is sized so that it cannot slide over push rod conveyor 116, it must instead push against conveyor 116 when the release lever is forced forward, toward the distal end of the apparatus, by spring 134.

As can be understood from FIGS. 2, 6, 17A-17C, 24, and 25A-25B, the proximal end of release lever 136 is in contact with spring 134. In the pre-activation state of the implant delivery device, release lever 136 compresses spring 134 against the distal end of knob shaft 74, and keeps the spring in a compressed state until the ejector button is depressed. This is made possible by a flexible tab 144 present on the release lever (seen in FIGS. 2, 14A-14B, 24, 25A, and 26A). Tab 144 is configured with a T-shaped protuberance 145 (FIGS. 14A-14B) that is too wide to pass through the gap between gate posts 147 present in track 140 on the interior of cover top 46 (FIGS. 11A-11C). As can be seen in FIGS. 11A-11C, track 140 in cover top 46 includes two gate posts 147 just proximal to the ejector button 64 inside cover top 46. In the pre-activation state of the apparatus, the two posts 147 prevent forward movement of the release lever (i.e., movement along the longitudinal axis of the housing in a direction toward the distal end of the device) due to the presence of the T-shaped protuberance 145 that catches on the gate posts 147. However, depression of ejector button 64 bends tab 144 down, which in turn allows protuberance 145 to pass over the gate posts. With its forward movement no longer blocked, the release lever 136 is driven forward by the spring toward the distal end of the apparatus (see beforeand after-activation views in FIGS. 20A-20B and 21A-21B). Forward movement means translation along the longitudinal axis of the housing toward the distal end of the apparatus.

Thus, as can be understood from the foregoing discussion and the attached figures, manual depression of ejector button 64 results in i) forward movement of push rod assembly sleeve 120 (and thereby forward movement of the entire push rod assembly 114 and implant holder 84, which is attached to the push rod assembly) along the longitudinal axis of the housing, and ii) detachment of release lever 136 from housing cover top 46, which thereby releases the mechanical energy stored in the compressed spring, thereby driving the release lever forward. As it is driven forward by the spring 134, the release lever 136, in turn, drives the push rod conveyor 116 forward through channel 126 present in push rod guide 118. Because the push rod and push rod conveyor are fixedly secured to one another, forward movement of push rod conveyor 116 drives push rod 108 forward through the lumen of the implant holder and the lumen of the needle, thereby causing ejection of the intracameral implant out the distal, beveled end of needle 56.

Referring to FIGS. 9A-9B and 25A-25B, the needle rotation assembly 78 comprises or consists of i) a needle-rotation knob 52 and the associated coding element 76, which shows the orientation of the needle bevel, ii) a knob shaft 74, and iii) a metal connecting rod 148. The metal connecting rod 148 operably links needle-rotation knob 52 at the proximal end of the device with push rod guide 118. As schematically shown by the arrows in FIGS. 4 and 9A-9B, metal connecting rod 148 transmits rotation of needle-rotation knob 52 by the user into rotary motion of push rod guide 118 and, thereby, into rotary motion of needle 56 at the distal end of the implant delivery apparatus. For this purpose, the distal and proximal ends of the metal connecting rod may be shaped to fit or mate with cavities present on the distal end of knob shaft 74 (described below) and at the proximal end of push rod guide 118. As is clear from FIGS. 2, 9A-9B, and 25A-25B as well the other views of the apparatus, knob 52 is configured to receive and operably engage with the proximal end of shaft 74. Thus, by rotating knob 52, torque can be applied to the metal connecting rod, the push rod guide, the implant holder, and the needle hub.

As explained above, needle-rotation knob 52 is operably connected to metal connecting rod 148 by way of a knob shaft 74. As shown in FIGS. 25A-25B, for example, knob shaft 74 is a cylindrically shaped element having distal and proximal ends, wherein the proximal end is configured to be received in and gripped by knob 52 inside the housing, and wherein the distal end comprises a recess configured to mate with the proximal end of metal connecting rod 148. As can be further seen in FIGS. 2, 6, 9A-9B, 24, and 25A-25B, Knob shaft 74, is configured with first, second, and third coaxial disks spaced at intervals along the axis of shaft 74: the first disk (149') (149 prime), acts as a backstop to spring 134, the second disk (149") (149 double prime) provides frictional resistance to the rotation of the shaft (by contact with tab 72 on cover bottom 48), and the third disk (149') (149 triple prime) provides flush contact with and receipt in knob 52. As may be apparent, Knob shaft 74 with the three coaxial disks can be manufactured as a single moldable plastic element. Referring to FIGS. 17A-17C, 20A-20B, 21A-21B, the second disk 149" of knob shaft 74 can be positioned in frictional contact with tab 72 on cover bottom 48. In this way, a small frictional force produced by tab 72 pressing against shaft 74 (via disk 149") acts as resistance to the rotation of knob 52. This friction force helps maintain the orientation of the needle bevel once selected by the user and helps prevent unintentional rotation of the needle during handling. Tab 72 is flexible yet resilient and may be formed of a moldable plastic piece and is formed as part of the cover bottom 48.

Figure 28A:
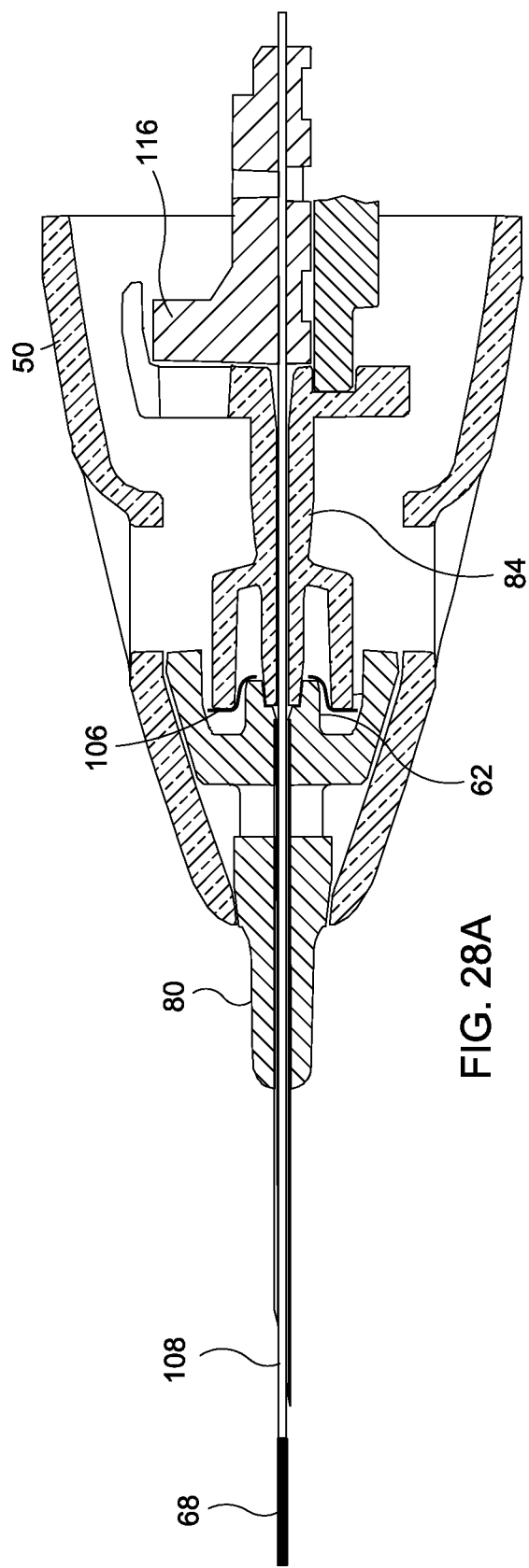
FIGS. 28A and B show enlarged side views of the distal end of the apparatus in section following activation of the apparatus. The implant 68 is shown being ejected from the tip of the needle. The distal end of the push rod 108 can be seen exiting the tip of the needle.

Due to the nature of the spring-driven mechanism, including the length of the push rod, and the particular assembly developed for the apparatus described herein, a portion of the distal end of the push rod 108 may exit the tip of the needle during ejection of the implant, as depicted in FIG. 21B and FIGS. 28A and B. This can happen because the push rod conveyor 116 and the push rod 108, which is associated with the push rod conveyor, are not fixedly attached to the release lever 136, the spring 134, or any other component of the spring-driven assembly. The push rod conveyor 116, is propelled forward, along the longitudinal axis of the housing and toward the distal end of the apparatus, through channel 126 in push rod guide 118 and, thus, push rod 108 is propelled through the lumen of the implant holder and the lumen of the needle, as a consequence of the release lever striking push rod conveyor 116. For most of the length of channel 126 in guide 118, push rod conveyor 116 is actively driven forward (i.e., is driven from a proximal position to a more distal position along the length of the housing) through the push rod guide toward the distal end of the apparatus by the release lever 136, which, in turn, is driven forward by the spring 134. However, as can be seen in the post-activation view depicted in FIGS. 21A-21B, and comparing to the pre-activation view depicted in FIGS. 17A-17C and 20A-20B, forward movement of the release lever is, eventually, abruptly halted by a rubber post 154 present distally in track 140 of cover bottom 48 (see also FIGS. 2 and 10A-10C). Specifically, forward procession of the release lever is blocked when lower rail 138 of the release lever makes contact with rubber post 154 in track 140 of the cover bottom. Rubber post 154 is an extension of the rubber-coated surface 70 or grip that is part of cover bottom 48 (see FIG. 5C). Thus, rubberized surface 70, which can be affixed, glued, or bonded to cover bottom 48, extends into the interior of cover bottom 48. The rubber post can serve to dampen the motion of the spring mechanism or spring-driven assembly, and because it is rubber, may also have the added effect of reducing the noise associated with activation of the device. As may also be appreciated, the position and variations in the position of the rubber post in track 140 in the cover bottom may influence the distance of an implant is ejected from the tip of the apparatus.

Figure 28B:
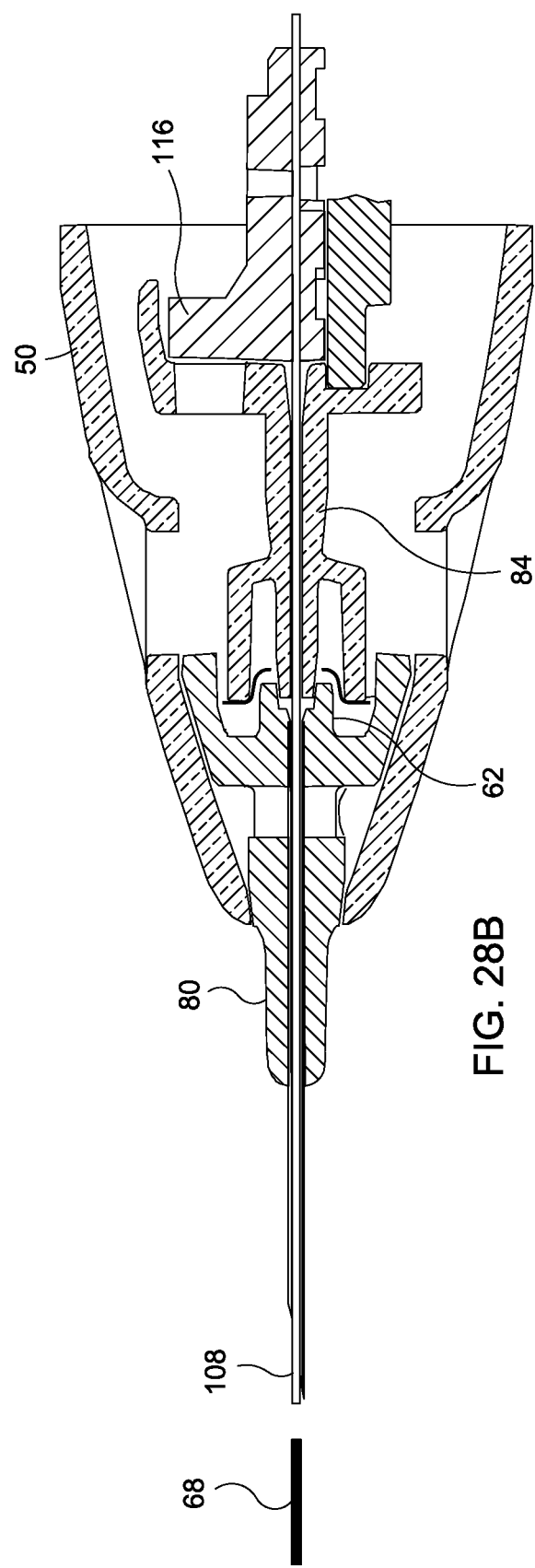

Though forward movement of release lever is suddenly stopped by rubber post 154, the stroke length of channel 126 in push rod guide 118 is such that there remains about 1-2 mm of additional channel 126 through which the push rod conveyor 116 may continue to travel before reaching the end of its path through the channel. Thus, for the last 1-2 mm of forward movement, the conveyor 116 and push rod 108 are no longer being actively pushed from behind by the release lever but instead travel freely in push rod guide 118. Upon hitting the end of the guide 118, the conveyor 116 and push rod 108, which is attached to the conveyor, are propelled or bounced backward in the opposite direction toward the proximal end of the device. The length of the push rod may be such that the tip of the push rod may momentarily exit out the end of the needle tip (as depicted in FIGS. 28A-28B) and then quickly retract when the push rod conveyor strikes the end of track or channel 126 in push rod guide 118.

This ejection-retraction action of the push rod upon activation of the device, wherein the distal end of the push rod momentarily exits the tip of the needle before retracting back inside the lumen of the needle, can be beneficial because it may help drive the implant away from the tip of the needle and into the fluid-filled medium of the anterior chamber. This may be a further advantage of the device because it may reduce and may eliminate the chance that the implant may adhere to the needle following ejection. Small air pockets that can form near and around the implant during assembly of an ocular implant delivery device are often released with the implant during ejection. In a fluid-filled environment such as the anterior chamber, these air pockets can manifest in the form of a small air bubble or air bubbles, which may adhere to both the implant and the needle tip, possibly tethering the implant to the needle or needle after ejection. Withdrawing the needle from the eye while the implant remains adhered to the needle can lead to complications for the patient. With the present device, however, a portion of the push rod exits out of the needle tip and then quickly retracts back inside the device. This exit and retraction action of the push rod may help break the surface tension of any air bubbles that attach to the implant and the tip of the needle when the implant is pushed out of the needle and may help drive the implant away from the device into the intracameral space (anterior chamber) of the eye.

As stated above and as shown in FIGS. 7A-7B and 20B, prior to activation of the apparatus, push rod 108 is positioned such that the intracameral implant is retained and secured in implant holder 84 by means of the membrane 106 at the distal end of the holder 84 and the push rod 108 at the proximal end of the holder 84. The membrane may be circular or non-circular and is sized to fully cover or block the distal end of the implant holder and is partially cut. For example, the membrane may be slit, cross-slit, or perforated, and made of such material that movement of the implant holder from a first position to a second position (in a direction away from the proximal end of the apparatus and toward the distal end of the apparatus (i.e., toward the needle) forces the membrane open or folds the membrane back and away from the lumen of the implant holder to allow for transfer of the implant from the lumen in the implant holder to the lumen of the needle. The opening or folding back of the membrane 106 upon activation of the apparatus (i.e., upon depression of the ejector button) is schematically depicted in FIGS. 7A-7B and 28A-28B and 20A-21B. As can be seen in the FIGS. 7A-7B, the distal end of the implant holder is fashioned such that it contains an inner smaller cylinder within a larger outer cylinder (the smaller cylinder constituting the lumen and containing the intraocular implant 68). As can be further understood by reference to FIGS. 7A and 7B, there is a void between the inner and outer cylinders into which the membrane 106 may be stuffed or folded as the implant holder 84 is driven forward against nipple 62.

As previously discussed, engaged with the proximal end of push rod 108 via push rod conveyor 116 is a compressed spring-driven assembly (including the release lever 136 and the spring 134), which, when triggered, is capable of forcing push rod 108 forward through the implant holder and into and through the lumen of the needle 56 attached to the needle hub 58, thereby driving the implant out of the holder 84, through the needle, and ultimately out the distal end of the needle into the external environment, such as, for example the anterior chamber of a patient's eye. Accordingly, the push rod 108, capable of being driven forward by the spring 134, is the means for ejecting the implant from the apparatus following activation of the apparatus.

The choice of spring type and spring constant may be used to tune the ejection force and ejection distance (the distance the implant is ejected away from the tip of the needle upon activation of the apparatus). According to some embodiments, the present apparatus may comprise a linear helical or a progressive helical spring. For example, the spring can be a coiled progressive compression spring as depicted in FIG. 25B. As can be appreciated, the force of ejection, which contributes to the distance the implant is ejected away from the tip of the needle (the ejection distance), will depend in part on the number of active or compressible coils, the "stiffness" of the spring, and the degree to which the spring is compressed inside the housing prior to activation. According to some embodiments the apparatus preferably ejects the intraocular implant a distance of 2-4 mm away from the tip of the needle in a liquid medium.

The spring-driven assembly (including the release lever and spring) is kept in a locked, ready-for-deployment position by the release lever due to a flexible yet resilient tab 144 and its associated T-shaped protuberance 145 located at the distal end of release lever 136, as seen in FIGS. 14A-14B. In the locked and ready position, prior to activation of the apparatus, the T-shaped protuberance 145 on tab 144 catches on the two gate posts 147 positioned at the distal end of track 140 of the cover top 46. It can be seen in FIGS. 11A-11C that one gate post 147 is positioned on each side of the track 140, much as sentries, to form a narrow gap through which the T-shaped protuberance 145 cannot pass. Thus, protuberance 145, being an integral part of release lever 136, holds release lever 136 in place, even under the rearward pressure emanating from a compressed spring 134 (spring 134 is compressed between the proximal end of release lever 136 and the back stop (disk 149) on knob shaft 74). From FIGS. 17A-17C and 20A-20B, it can be seen that protuberance 145 and thus tab 144 of the release lever is in contact with the underside of ejector button 64 extending inside the housing through opening 66 in cover top 46. The energy stored in the compressed spring is released, and the spring-driven assembly is thereby translated forward (i.e., along the length of the housing and toward the distal end of the apparatus) under pressure from the spring, when tab 144 on release lever 136 is forced down, out of its locked position, by manual depression of ejector button 64. Tab 144 can be of a moldable plastic and integrally formed with the release lever.

It will be understood from the many views of the apparatus provided with this description that the underside of the ejector button is also operably connected with push rod guide 118 and implant holder 84 by way of the push rod assembly sleeve 120. The user transmits force to the sleeve through the underside of the button by manually depressing the button. As seen in FIGS. 2, 20A-20B, 21A-21B, and 24, curved flanks (or wings) 124 present on the portion of the ejector button that extends inside the housing are disposed between posts 122 and 122'. When ejector button 64 is depressed, wings 124 on button 64 slide against posts 122 that extend laterally from each side of the sleeve 120. In this way, the wings on ejector button 64 serve to nudge sleeve 120 forward, in a direction along the longitudinal axis of the housing, toward the distal end of the apparatus. Accordingly, force applied to ejector button 64 in a direction normal to the longitudinal axis of the housing by the user is converted into a longitudinal force (a force aligned with the longitudinal axis of the housing) on sleeve 120 and, thereby, the push rod guide 118 and, in turn, the implant holder 84, which is attached to the distal end of guide 118. The longitudinal force on the sleeve and therefore push rod guide causes the push rod guide to translate forward along the longitudinal axis of the housing and in a direction toward the distal end of the apparatus. This forward motion of the push rod guide, in turn, causes the implant holder to translate forward against nipple 62 inside needle hub 58. When forced against the membrane, nipple 62 forces open membrane 106 affixed to the distal end of the implant holder, as, for example, by causing the membrane or sections of the membrane to fold back, providing for unimpeded passage of the implant from the lumen of the implant holder into the lumen of the needle 56. See FIGS. 7A-7B.

Thus, manual depression of the ejector button (activation of the apparatus) simultaneously opens the membrane and triggers ejection of the implant from the device.

The present apparatus provides a significant advantage in that the user has no influence on the ejection force (and therefore ejection distance) of the implant. The user activates the ejection mechanism by depressing ejection button 64 but does not control the force by which the push rod moves through the implant holder or needle. This is entirely a function of the spring type, and potentially, by dampening features, if any. The depression of the ejector button moves the implant holder 84 against the nipple 62 forcing open the membrane, which previously closed communication between the implant holder and the needle, and concurrently forces the tab 144 on the release lever 136 down and the protuberance 145 out of its locked position by pushing it over the posts 147 that previously blocked its path. However, after this sequence is complete, the user no longer influences the moving parts. Once the release lever is forced out of its locked position by depression of button 64, the stored energy in spring 134 is released and transmitted to the push rod 108, causing the push rod 108 to move through the implant holder 84 and the needle lumen with a force that is determined entirely by the spring present inside the housing. The membrane also prevents the implant from prematurely falling out the distal end of the implant holder during assembly, storage, and handling of the apparatus.

The movement of push rod 108 by spring 134 thereby forces the implant out of the holder 84, through the needle lumen, and eventually out of the needle and into the eye. The distance the implant is ejected away from the tip of the needle and into the intracameral space of the eye can, therefore, be pre-set by the spring set up (e.g., spring type, spring constant, and degree of compression). Additional rubber or plastic components may be optionally included inside the housing, if desired, to dampen the force generated by the spring, to fine tune the ejection distance of the implant, or to further minimize the noise associated with the activation of the apparatus and ejection of the implant. For example, rubber components can be added between the implant holder and the needle hub where contact may occur and where a "click" sound might be heard. Thus, the force applied to the ejector button is not proportional to and does not influence the force by which the implant is ejected. This design provides for consistent, user-independent performance, whereby the ejection force of the implant is a product of the internal spring-driven assembly of the apparatus and not the user.

In addition, the activation path (the distance the ejector button must travel to trigger ejection of the implant) in the present apparatus may be shorter than some other implant delivery devices. For example, in the present apparatus the activation path can be about 1 mm to 2 mm, whereas some devices may require that the button be depressed by up to about 5 mm or more before activation (actuation) takes place. The longer the activation path the greater the possibility for shaking of the apparatus and, possibly, moving the tip of the needle while in the eye. The shorter activation path of the present apparatus is expected to result in a more comfortable and more controlled, less shaky implant delivery procedure for patient and doctor.

It is desirable to use a high gauge (e.g., 27 gauge to 30 gauge) needle. The distal end of the needle is preferably beveled to facilitate penetration of the eye, such as the cornea, sclera, and vitreous cavity. Accordingly, the needle may correspond to a 27 gauge, 28 gauge, 29 gauge, or 30 gauge needle. Smaller (higher gauge) needles are preferred for injection into the eye to minimize trauma and fluid leakage. The needle may be cylindrical or non-cylindrical, and may therefore have a circular or non-circular cross-sectional area. In either form, the needle is preferably able to receive a fiber-, filament-, tubular-, or rod-shaped intraocular implant within its lumen.

Because the present apparatus provides a means for rotating the needle, the bevel may be rotated clockwise or counter-clockwise to suit the user's preference. Thus, the bevel may be oriented toward or away from the globe of the eye, depending on the needs or preference of the user. This enables the user to grasp the apparatus with either hand in the manner desired with fore-, index-, or ring-finger or thumb on the ejector button and to then approach either the right or left eye at the angle necessary and with the bevel up or down or in any other desired orientation to deliver the implant into the eye (including the anterior chamber or vitreous body of the eye). See FIGS. 8A-8B, for example.

The means used to rotate the needle can be understood by reference to FIG. 4. The needle is rotated using the needle (or bevel) rotation knob 52 located at the proximal end of the housing 40. As can be seen in FIGS. 1A-3, 5A-5C, 6, 8A-8B, and 9A-9B, the knob itself (in association with the coding element 76) is beveled to match the needle bevel. As discussed previously, the coding element is component that is attached to the end of the needle-rotation knob that serves to indicate the position of the needle bevel. It is a single moldable piece having a finger-like projection 75 that runs longitudinally along the surface of the knob and a beveled back surface 77 that attaches flush to the proximal end of the needle-rotation knob. Thus, when connected to the coding element the needle-rotation knob has a beveled end similar to the needle. The bevel of the knob and the finger-like projection 75 running lengthwise along the outer surface of the knob are aligned with the bevel of the needle to clearly and unambiguously indicate the orientation of the needle bevel. A rubber or plastic material may be positioned between the bevel rotation knob and the housing, or the knob may be simply snugly fit to the housing to provide frictional resistance to the rotation of the knob, securing the knob once the user has rotated it to the desired location. Alternatively, or in addition, the top or bottom cover of the housing may be configured with a flexible tab, such as tab 72 previously discussed, that tends to flex against a portion of shaft 74 connected to knob 52 in the interior of the housing. This applies a frictional force to the shaft 74 that resists free, unintended movement of the needle rotation knob 52 and thereby ensures that the needle stays in position, initially selected by the user, during use of the apparatus.

As can be understood from FIGS. 2, 6, 9A-9B, and 25A-25B, knob 52 is operably connected to metal connecting rod 148 inside the housing via shaft 74. Metal connecting rod 148 is fixedly mated with knob shaft 74 inside the housing and to push rod guide 118. As can be understood from FIGS. 2, 6, 21A-21B, and 25A-25B, metal rod 148 extends through the center of spring 134. Metal connecting rod 148 transmits the rotary motion applied to knob 52 by the user into rotary motion of push rod guide 118 through to implant holder 84 and needle hub 58 at the distal end of the device. In this way, by twisting knob 52 the user can twist or rotate needle 56 and thereby orient the bevel of needle 56 relative to the surface of the eye. Thus, needle rotation knob 52 may also be referred to as a bevel rotation knob As previously discussed, the presently described intraocular implant delivery apparatus may further include features such as implant inspection windows 112 and 112' located in the nose cone 50 and needle hub 58, respectively, to facilitate visual or automated inspection of the intraocular or intracameral implant 68 in the device following assembly, a delivery feedback window 86 to confirm successful activation of the apparatus, and rubberized grips 70 on the exterior of the housing (e.g., the cover bottom) along with a triangular shape or triangular rounded shape or grip to improve the handling, manipulation, and control of the apparatus by the physician. See FIGS. 1A-5C and 17A-17C, as well the other figures accompanying this disclosure. In its final assembled form, the apparatus also includes a removable safety cap 44, fitted and locked into place over the nose cone 50. The safety cap not only covers and guards the needle but also blocks depression of the ejector button during shipping and handling. Safety cap is configured with a bendable Tab 89a that clicks into recesses (88a-d, for example) located on nose cone 50, cover top 46, and cover bottom 48 and in doing so places a projection 92 against a boss section 94 on ejector button 64 (FIGS. 1A-1D, 5A-5C, and 17A-17C). This interaction prevents premature activation of the device by blocking the upward movement of boss 94, which, as evident from the configuration and see-saw pivot axis 95 of ejector button 64, (FIGS. 18A-18E and 20A-20B), must occur when the ejector button is depressed. In one embodiment, the safety cap is removed and the safety lock is freed, by rotating the cap and pulling the cap from the apparatus.

As described above, the present apparatus is particularly well suited for delivering a rod-shaped intracameral implant into the anterior chamber of a patient's eye. In other embodiment, the apparatus is used in a method for introducing a rod-shaped biodegradable drug-containing implant into an ocular region of the eye such as, for example, the subconjunctival space, subtenon space, or vitreous body of the eye to treat a medical condition of the eye. The method can comprise the steps of inserting the needle of the apparatus into the subconjunctival space, subtenon space, or vitreous body of an eye (for example, the patient's eye), ejecting the implant from the apparatus into the subconjunctival space, subtenon space, or vitreous body of the eye and removing the needle from the eye. According to some embodiments, the apparatus is used to deliver two or more rod-shaped intraocular drug-containing implants into the anterior chamber, subconjunctival space, subtenon space, or vitreous body of the eye to treat a medical condition of the eye. The patient can be a human or non-human mammal in need of treatment for a medical condition of the eye (an ocular condition), such as for example glaucoma or ocular hypertension. Delivery of an implant into the anterior chamber of the eye will generally comprise inserting the needle through clear cornea into the intracameral space (or anterior chamber). Once the needle is advanced to the desired position the ejector button is depressed.

Because the apparatus can comprise a 28 gauge or higher gauge needle, the procedure may be less traumatic than with larger gauge needles. The length of needle protruding from the stop or nose 80 on needle hub 58 is set to be optimal for insertion into the anterior chamber of the eye. In general, this length can be 4 mm to 8 mm, 4 mm to 7.5 mm, 4 mm to 6 mm, 4 mm to 5 mm, about 5 mm, or about 7.5 mm, as measured from the tip 82 of the needle to the nose 80 of the needle hub. The provision of stop 80 on needle hub 58 reduces the risk of advancing a needle too far into the eye, removing uncertainty, and the user-independent spring-driven ejection mechanism safely and reliably delivers the implant into the anterior chamber with optimum force.

Because the push rod assembly is designed to drive the implant well away from the tip of the needle and into the fluid-filled medium of the anterior chamber, it is expected that the present device may reduce the incidence of implants adhering to the end of the needle and thereby the chance that an implant is dragged out of the eye or becomes lodged in the cornea when the needle is removed. Deposition of the implant in the corneal endothelium may result in adverse complications. Intracameral implants preferably separate from the needle tip immediately after ejection. The present device can provide for clean separation of the implant from the device since the push rod may not only drive the implant through the lumen of the needle but may also drive the implant away from the needle tip, thereby dislodging any air bubbles formed at the needle tip during discharge of the implant.

In one embodiment of the foregoing method, the intracameral implant is biodegradable and is produced by an extrusion process. Extruded implants will generally comprise a biodegradable polymer matrix and a pharmaceutically active agent associated with the polymer matrix. The pharmaceutically active agent can be a chemical compound, protein, or substance effective for treating a medical condition of the eye. Examples of pharmaceutically active agents include, but are not limited to steroids, non-steroidal anti-inflammatory agents, alpha-2 adrenergic receptor agonists, prostamides, tyrosine kinase inhibitors, VEGF inhibitors, cyclosporins (such as, for example, cyclosporin A), and proteins.

Non-limiting examples of steroids that may be effective for treating a medical condition of the eye include dexamethasone, beclomethasone, betamethasone, and triamcinolone, and pharmaceutically acceptable salts thereof.

Non-limiting examples of non-steroidal anti-inflammatory agents that may be effective for treating a medical condition of the eye include aspirin, diclofenac, flurbiprofen, ibuprofen, ketorolac, naproxen, and suprofen, and pharmaceutically acceptable salts thereof.

Non-limiting examples of alpha-2 adrenergic receptor agonists that may be effective for treating a medical condition of the eye include brimonidine freebase and brimonidine tartrate.

Frostamides are potent ocular hypotensive agents useful in the treatment of a number of various ocular hypertensive conditions such as glaucoma, elevated intraocular pressure, and other ocular hypertensive episodes. They belong to an ever-expanding family of prostaglandin $F_{2\alpha}$ C-1 amides. The biosynthesis and pharmacology of prostamides has been extensively described (e.g., Woodward et al. (2004) "Bimatoprost: A novel antiglaucoma agent" *Cardiovascular Drug Reviews* 22(2):103-120). For example, naturally occurring prostamides, such as prostamide $F_{2\alpha}$, are biosynthesized from anandamide by a pathway exclusively involving COX-2. COX-1 is not involved (e.g., Yu et al. (1997) "Synthesis of prostaglandin $E_2$ ethanolamide from anandamide by cyclooxygenase-2" *J. Biol. Chem.* 272(34):21181-21186). One prostamide that has found wide-spread use in ocular therapy is bimatoprost (CAS Registry No. 155206-00-1) (Patil et al., 2009, "Bimatoprost-a review" *Expert Opinion Pharmacother.* 10(16):2759-2768). Like other prostamides, bimatoprost exhibits no meaningful interaction with prostaglandin (PG) sensitive receptors (Schuster et al. (2000)) "Synthetic modification of prostaglandin $F_{2\alpha}$ indicates different structural determinants for binding to the prostaglandin F receptor versus the prostaglandin transporter" *Mol. Pharmacology* 58:1511-1516). Nevertheless, bimatoprost is a potent ocular anti-hypertensive agent and is highly effective for reducing elevated intraocular pressure in patients with open angle glaucoma or ocular hypertension (Coleman et al. (2003) "A 3-Month Randomized Controlled Trial of Bimatoprost (LUMIGAN®) versus Combined Timolol/Dorzolamide (Cosopt®) in Patients with Glaucoma or Ocular Hypertension" *Ophthalmology* 110(12): 2362-8.) Biodegradable implants comprising a prostamide such as bimatoprost for placement in an ocular region of the eye are described in U.S. Pat. No. 7,799,336. In some embodiments, the active agent is homogeneously or substantially uniformly distributed throughout the biodegradable polymer matrix of the implant or may be present in the core or a reservoir within the implant and surrounded by an outer biodegradable or non-biodegradable layer.

As used herein, a "protein" shall have its common meaning as known in the art, and can refer to biological molecules consisting of one or more chains of amino acids. Proteins can perform a vast array of functions within living organisms, including catalyzing metabolic reactions, replicating DNA, responding to stimuli, transporting molecules from one location to another, and acting as signaling molecules, as when they bind to a cell surface receptor. Proteins may be linear, branched, or circular and may be chemically synthesized or naturally or recombinantly produced. In some embodiments, therapeutic proteins may also include proteins that are modified, such as PEGylated proteins, or post-translationally modified proteins.

Non-limiting examples of proteins that may be effective for treating a medical condition of the eye include proteins that specifically bind vascular endothelial growth factor (VEGF). Proteins that specifically bind VEGF in the eye may be effective for inhibiting, blocking, or reducing VEGF activity in an eye. The protein that specifically binds VEGF can be a monoclonal antibody, DARPin, or anticalin. Anti-VEGF proteins such as these may be effective for reducing, retarding, or inhibiting neovascularization in an eye and for treating macular degeneration.

An intraocular implant, such as an intracameral implant, comprising a pharmaceutically active agent, such as an anti-hypertensive agent, may be effective for reducing intraocular pressure (IOP) in the eye of a patient suffering from glaucoma or ocular hypertension. For example, an intracameral implant can be placed in the anterior chamber of the eye to deliver a therapeutically effective dose of an TOP-lowering drug, such as bimatoprost or other prostamide, for an extended period (e.g., 30 days or more). The anterior chamber refers to the space inside the eye between the iris and the innermost corneal surface (endothelium).

Figure 29:
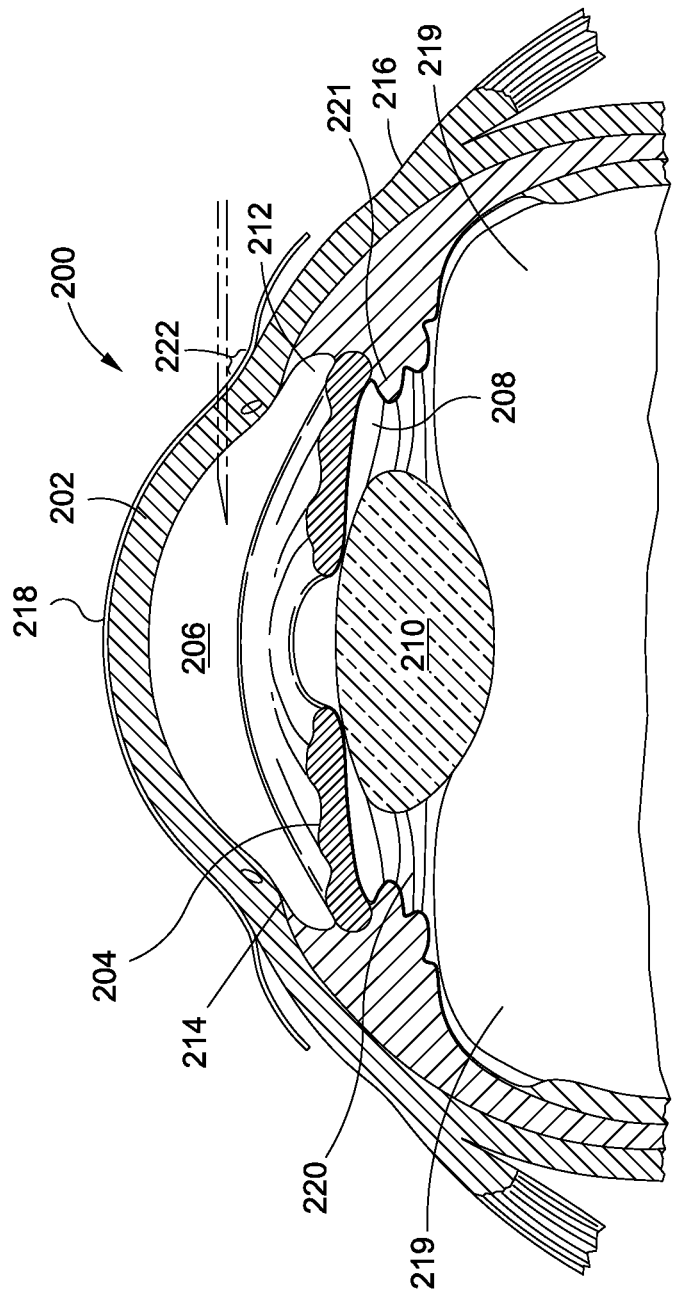
FIG. 29 shows a cross section of the mammalian eye.

While the implant delivery apparatus described in this disclosure is designed for introducing a solid, rod-shaped implant into the anterior chamber of an eye of a human or non-human mammal (such as a dog, monkey, and the like), the apparatus in accordance with this disclosure may find use in a method for introducing an intraocular implant into other locations (or ocular regions) in the eye. Thus, for example, it may be possible to use the present apparatus in a method to deliver a drug-containing intraocular implant into the vitreous body, subconjunctival space, subTenon's space, or posterior chamber of the eye, which is the space inside the eye between the back of the iris and the front face of the vitreous. The posterior chamber includes the space between the lens and the ciliary processes, which produces the aqueous humor that nourishes the cornea, iris, and lens and maintains intraocular pressure. Referring to FIG. 29, these and other ocular regions of the eye (200) are shown in cross-section. Particular regions of the eye (200) include the cornea (202) and iris (204), which surround the anterior chamber (206). Behind the iris (204) is the posterior chamber (208) and lens (210). Within the anterior chamber is the anterior chamber angle (212) and trabecular meshwork (214). Also shown are the corneal epithelium (218), sclera (216), vitreous (219), ciliary zonules (220), and ciliary process (221). Also shown is the limbus (222), which is the transition zone about 1-2 mm wide, where the cornea joins the sclera and the bulbar conjunctiva attaches to the eyeball. The posterior segment of the eye is the rear two-thirds of the eyeball (behind the lens), and includes the vitreous, the retina, and the optic nerve.

To administer an intraocular implant into an ocular region of the eye, such as the anterior chamber, using the intraocular implant delivery apparatus according to the present disclosure, the user can grasp the apparatus 40 between the thumb and middle finger or between index and middle finger along rubber-coated surfaces 70, as shown in FIGS. 8A-8B, and position the apparatus near the desired point of entry into the patient's eye. The device allows one to comfortably use either the thumb or index finger to depress the ejector button. Generally, the needle is inserted into the anterior chamber of an eye by inserting the needle through the cornea at a point just anterior to the limbus (or corneo-scleral junction, where the cornea joins the sclera and the bulbar conjunctiva attaches to the eyeball). The needle is then advanced into the eye to a length of about 4 mm, as measured from the tip 82 of the needle, and the tip of the needle is pointed or aimed toward the inferior anterior chamber angle. The ejector button is then depressed to deploy the implant. The patient typically will be under a topical or local anesthetic. The needle is then withdrawn. Preferably, the resultant puncture site can self-seal upon withdrawal of the needle. Best results may be achieved by orienting the bevel of the needle away from the surface of the eye.

According to some embodiments, an apparatus in accordance with this disclosure is used to delivery an intracameral drug-containing, rod-shaped implant into the anterior chamber of an eye, such as a human eye. Because of the extremely small cross-sectional diameters or areas of intracameral implants, the length of the implant may need to be proportionally larger to provide the desired therapeutic dosages of some active agents. According to some embodiments, an intracameral implant is a cylindrical or non-cylindrical rod-shaped implant that is 0.5 mm to 2.0 mm, 0.5 mm to 2.5 mm, or 0.5 mm to 2.7 mm in length and from 150 µm to 250 µm or 150 µm to 200 µm (±10 µm) in diameter or width. According to some embodiments, the total weight of the intracameral implant is 20 µg to 120 µg or 50 µg to 100 µg (±10 µg). Preferably, the implant does not interfere with a patient's vision or result in other undesirable complications in the eye following placement in the anterior chamber of the eye.

Various methods may be employed to make a biodegradable intracameral implant suitable for delivery with the present apparatus. Useful methods may include hot-melt extrusion methods, compression methods, pellet pressing, solvent casting, print technology, hot embossing, soft lithography molding methods, injection molding methods, heat press methods and the like. The biodegradable intracameral implant for delivery with the present apparatus can be configured as a rod. According to some embodiments, cast films or sheets are ground into microparticles that are then extruded into a rod-shaped filament. Alternatively, polymers and drug are dry mixed and then hot-melt extruded into a rod-shaped filament having a diameter and cut to a length suitable for placement in the anterior chamber of the eye. The intraocular implant may be sized and configured for delivery through a 28 gauge, 29 gauge, or 30 gauge needle and for compatibility with the anterior chamber of the eye, whereby the implant can fit into the anterior chamber angle (212 in FIG. 29) without touching or rubbing against the corneal endothelium, which can cause inflammation in the eye.

Methods for making a biodegradable bimatoprost-containing intraocular implant by an extrusion process are familiar to those of skill in the art. See, for example, U.S. 2008/0145403 and U.S. 2005/0244464, which are herein incorporated by reference. An extruded implant (e.g., an extruded rod) can be made by a single or double extrusion method. The use of extrusion methods may allow for large-scale manufacture of implants and may result in implants with a homogeneous dispersion of the drug within the polymer matrix. These processes may be adapted for use in making other prostamide-containing intraocular implants.

In manufacturing an implant delivery device according to the invention, the device may be pre-loaded with the implant and then sterilized, adding convenience for the user and avoiding unnecessary handling of implants. A suitable dose of radiation for sterilization may be from 20 kGy to 30 kGy.

In manufacturing the present intracameral implant delivery apparatus, needle rotation assembly 78, the spring-driven assembly, and push rod assembly 114 can be pre-assembled separately and the individual assemblies then interconnected. It may be appreciated that several of the components may be formed of moldable plastic configured the features described herein. Push rod 108 and metal connecting rod 148 can be metal or a metal alloy. Alternatively, in some embodiments, the push rod or connecting rod or both can be formed from a plastic or non-metallic material.

When interconnected, the three assemblies align along the longitudinal or long axis of the housing as depicted in FIGS. 9A-9B, 24, and 25A-25B. As can be understood from FIGS. 6 and 25A-25B, and the several other figures accompanying this description, metal connecting rod 148 extends through spring 134, release lever 136, and push rod assembly sleeve 120 and fixedly interconnects to the proximal end of push rod guide 118. The interconnected assemblies, including the sleeve, can be interconnected then be enclosed within the housing formed initially by attachment of cover top 46 (containing ejector button 64 extending through opening 66) to cover bottom 48. Nose cone 50 is attached at a later step, as described below. As will be understood by reference to FIGS. 2, 10A-10C, 11A-11C, 17A-17C, 20A-20B, and 21A-21B, ribs 156 on the interior of cover bottom 48 and cover top 46 at the proximal end of the cover bottom and top come into contact with disk 149' on knob shaft 74, blocking backward movement of the shaft 74 (toward the proximal end of the apparatus). This blocks rearward movement and escape of those members (e.g., push rod guide and implant holder) fixedly secured to the shaft by the metal connecting rod 148. This fixes in place within the housing the knob shaft, the metal connecting rod, and the push rod guide. The blocked rearward movement is important since the knob shaft ultimately serves as the backstop to the spring, which when compressed places pressure against the knob shaft 74. See FIGS. 2, 17A-17C, 20A-20B, and 24. The ribs 156 in the housing cover top and bottom hold the shaft in place during compression of the spring in the assembly process.

In a separate process, an intraocular implant (e.g., a rod-shaped, biodegradable, intracameral implant) can be pre-loaded in implant holder 84 having membrane 106 affixed to its distal end. Membrane 106 can, for example, be heat sealed onto the distal end of the implant holder and the implant can be inserted into the implant holder. The implant holder 84 can then be fixedly attached to the snap hooks 130 at the distal end of plunger guide 118. At this step, push rod 108 is received in the lumen of implant holder 84 where it will serve as a back stop to the implant prior to deployment in the eye. Loss of the implant is prevented at this stage by the presence of the membrane 106.

Before attaching the nose cone to the cover top and bottom (46 and 48) and before the implant holder and push rod guide are connected to the metal connecting rod 148 inside the housing, the spring is "cocked" into the compressed and ready-for-activation position by pushing the release lever back toward the proximal end of the housing. This can be done, for example, by inserting a solid cylindrical rod into the uncapped, open distal end of the apparatus distal and then pushing the release lever back against the spring. In doing so, the user will usually hear an audible click when the T-shaped protuberance 145 on release lever tab 144 flips over the gate posts 147 present at the distal end of track 140 on the underside of cover top 46. At this point the spring driven mechanism is locked and ready for activation.

Next, the push rod guide 118 in association with the push rod 108, conveyor 116, and implant holder 84 is inserted through the uncapped distal end of the apparatus to connect the guide 118 with the metal connecting rod 148. Next, nose cone 50 containing needle hub assembly 54 is snapped onto the proximal ends of cover top 46 and cover bottom 48. Finally, safety cap 44 is secured into place over nose cone 50 to complete the assembly. The apparatus can then be packaged and sterilized.

As can be appreciated, label plates or other locations on the housing can include appropriate information relative to the particular implant loaded (e.g., drug, dosage, implant composition, and the like). Given this interchangeability, unique apparatus for the delivery of selected implants can be easily manufactured.

Accordingly, the assembly of the intraocular implant delivery apparatus according to this disclosure is straight forward and may be amenable to automation. Because the implant holder with implant is a separate, self-contained unit that is attached to the assembly in one quick step without the need for extra steps or parts, such as needle notching, crimping, or use of sleeves, O-rings, or plugs to prevent implant loss during assembly as may be necessary in delivery devices in which the implant is stored in the lumen of the needle or in a passageway just proximal to the lumen, the cost of assembly may be reduced and the efficiency of assembly increased relative to some other devices in which the implant must be retained in the lumen of the needle or cannula prior to use.

What is claimed is:

1. An apparatus for injecting an intraocular implant into the anterior chamber of a patient's eye, the apparatus comprising:

(a) an elongate housing having a longitudinal axis and having a proximal end and a distal end;

(b) an ejector button extending through an opening in the housing and moveable from a first position to a second position in a direction normal to the longitudinal axis of the housing;

(c) a needle having a proximal end and a distal beveled end, the needle extending longitudinally from the distal end of the housing, the needle having a lumen extending through a length of the needle such that an intraocular implant can be received within and translated through the lumen of the needle, the needle rotatable, relative to the elongate housing, in clockwise and counter-clockwise directions about its long axis; and (d) an implant holder having a proximal and a distal end and a lumen capable of receiving and holding an intraocular implant prior to activation of the apparatus, the implant holder located inside the housing, the implant holder further being capable of movement, upon activation of the apparatus, from a first position to a second position within the housing along the longitudinal axis of the housing and in a direction toward a distal end of the apparatus, the lumen of the implant holder aligned with the lumen of the needle such that an implant can slidably translate from the lumen of the implant holder into the lumen of the needle upon activation of the apparatus, the implant holder capped at its distal end with a cross-slit membrane, and;

(e) a needle-rotation knob located at the proximal end of the housing, whereby manual rotation of said knob in a clockwise or counter-clockwise direction relative to the longitudinal axis of the housing is configured to result in a corresponding clockwise or counter-clockwise rotation of the needle along the same longitudinal axis as the elongate housing thereby allowing full 0° to 360° rotation of the distal beveled end of the needle as well as any incremental degree of rotation therebetween;

wherein depression of the ejector button is configured to result in activation of the apparatus and ejection of the implant from the apparatus.

2. The apparatus of claim 1, further comprising an intraocular implant, the intraocular implant located entirely within the implant holder, wherein the intraocular implant is a solid, rod-shaped, biodegradable, intraocular implant comprising a biodegradable polymer matrix and a pharmaceutically active agent associated with the biodegradable polymer matrix, wherein the pharmaceutically active agent is effective for treating a medical condition of the patient's eye, and wherein the intraocular implant is 150 µm to 300 µm in diameter or width, 0.50 mm to 2.5 mm in length, and 20 µg to 120 µg in total weight.

3. The apparatus of claim 2, wherein the length of the needle extending from the distal end of the housing is 4 mm to 8 mm.

4. The apparatus of claim 2, wherein the pharmaceutically active agent is a steroid, a non-steroidal anti-inflammatory agent, an alpha 2 adrenergic receptor agonist, a prostamide, or a protein.

5. A method of introducing an intraocular implant into the anterior chamber of a patient's eye using the apparatus of claim 2, the method comprising:
(a) providing the apparatus according to claim 2;
(b) penetrating the cornea of a patient's eye with the distal beveled end of the needle;
(c) inserting the needle into the anterior chamber of the patient's eye;
(d) ejecting the intraocular implant from the apparatus into the anterior chamber of the patient's eye;
(e) and removing the needle from the patient's eye.

6. The method of claim 5, wherein penetrating the cornea of a patient's eye comprises inserting the needle into the cornea with the bevel of the needle oriented 180° away from the surface of the eye.

7. The method of claim 6, wherein the needle is inserted into the anterior chamber by inserting the needle through the cornea at a point anterior to the limbus.

8. The method of claim 5, wherein the needle is inserted into the anterior chamber to a depth of about 4 mm to about 7.5 mm, as measured from a tip of the needle to the corneal surface where the needle first penetrates the eye, and wherein the needle is pointed toward the inferior anterior chamber angle before ejecting the implant.

9. The method of claim 5, wherein the patient has glaucoma or ocular hypertension.

10. The apparatus of claim 1, further comprising a push rod having a proximal and a distal end, wherein prior to activation of the apparatus the distal end of the push rod is disposed in the lumen of the implant holder at the proximal end of the implant holder, and wherein the push rod is slidably receivable within the lumen of the implant holder and the lumen of the needle, and wherein the push rod is moveable along the longitudinal axis of the housing.

11. The apparatus of claim 10, further comprising a spring-driven assembly engageable with the push rod for forcing the push rod through the implant holder and the lumen of the needle following activation of the apparatus.

12. The apparatus of claim 1 further comprising implant inspection windows located on the distal end of the housing, wherein said implant inspection windows are configured to permit visual observation of an implant inside the housing prior to activation of the apparatus.

13. The apparatus of claim 1, further comprising an implant delivery feedback window located on the housing, wherein said implant delivery feedback window is configured to allow observation of a visible signal that indicates activation of the apparatus.

14. The apparatus of claim 1, wherein said needle is a 28 gauge needle with a wall that is 0.0015 inches to 0.00225 inches thick.

* * * * *